(12) United States Patent
Satoh et al.

(10) Patent No.: US 10,174,025 B2
(45) Date of Patent: Jan. 8, 2019

(54) PYRAZOLE DERIVATIVE MANUFACTURING METHOD

(71) Applicant: MOCHIDA PHARMACEUTICAL CO., LTD., Tokyo (JP)

(72) Inventors: Tsutomu Satoh, Tokyo (JP); Takashi Kudoh, Tokyo (JP); Tetsuo Iwama, Tokyo (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/840,858

(22) Filed: Dec. 13, 2017

(65) Prior Publication Data

US 2018/0099964 A1  Apr. 12, 2018

Related U.S. Application Data

(62) Division of application No. 15/329,447, filed as application No. PCT/JP2015/071536 on Jul. 29, 2015, now Pat. No. 9,879,009.

(30) Foreign Application Priority Data

Jul. 30, 2014  (JP) ................. 2014-155538
Sep. 17, 2014  (JP) ................. 2014-189458

(51) Int. Cl.
C07D 471/04 (2006.01)
C07D 403/04 (2006.01)
C07D 401/14 (2006.01)
C07D 213/73 (2006.01)

(52) U.S. Cl.
CPC ......... C07D 471/04 (2013.01); C07D 213/73 (2013.01); C07D 401/14 (2013.01); C07D 403/04 (2013.01)

(58) Field of Classification Search
CPC ... C07D 471/04; C07D 403/04; C07D 401/14
USPC ....................................... 546/119
See application file for complete search history.

(56) References Cited

U.S. PATENT DOCUMENTS

| | | | |
|---|---|---|---|
| 2,450,386 A * | 9/1948 | Short | C07D 213/78 546/229 |
| 8,980,888 B2 | 3/2015 | Okano et al. | |
| 8,980,889 B2 | 3/2015 | Okano et al. | |
| 9,440,970 B2 | 9/2016 | Okano et al. | |
| 9,453,015 B2 | 9/2016 | Okano et al. | |
| 9,458,157 B2 | 10/2016 | Okano et al. | |
| 2012/0142665 A1 | 6/2012 | Flohr et al. | |
| 2014/0303141 A1 | 10/2014 | Flohr et al. | |
| 2014/0378447 A1 | 12/2014 | Okano et al. | |
| 2015/0132327 A1 | 5/2015 | Okano et al. | |
| 2015/0133448 A1 | 5/2015 | Okano et al. | |
| 2015/0166536 A1 | 6/2015 | Okano et al. | |
| 2016/0347751 A1 | 12/2016 | Okano et al. | |
| 2017/0217958 A1 | 8/2017 | Satoh et al. | |

FOREIGN PATENT DOCUMENTS

| | | |
|---|---|---|
| JP | 2013-544859 A | 12/2013 |
| WO | WO 2012/076430 A1 | 6/2012 |
| WO | WO 2013/041472 A1 | 3/2013 |
| WO | WO 2013/117610 A1 | 8/2013 |
| WO | WO 2014/133046 A1 | 9/2014 |
| WO | WO 2014/177493 A1 | 11/2014 |

OTHER PUBLICATIONS

International Search Report, issued in PCT/JP2015/071536, dated Sep. 8, 2015.
International Search Report, issued in PCT/JP2015/071560, dated Sep. 8, 2015.
Mendiola et al., "Preparation, Use, and Safety of O-Mesitylenesulfonylhydroxylamine", Organic Process Research & Development, 2009, vol. 13, No. 2, pp. 263-267.
Written Opinion of the International Searching Authority (PCT/ISA/237), issued in PCT/JP2015/071536, dated Sep. 8, 2015.
Written Opinion of the International Searching Authority (PCT/ISA/237), issued in PCT/JP2015/071560, dated Sep. 8, 2015.

* cited by examiner

Primary Examiner — Niloofar Rahmani
(74) Attorney, Agent, or Firm — Birch, Stewart, Kolasch & Birch, LLP

(57) ABSTRACT

The present invention provides a method for manufacturing a compound represented by formula (I). With this method, provided are a method for manufacturing a 4-heteroaryl-N-(2-phenyl-[1,2,4]triazolo[1,5-a]pyridin-7-yl)-1H-pyrazole-5-carboxylic acid amide derivative; and an intermediate for this manufacturing method.

[C217]

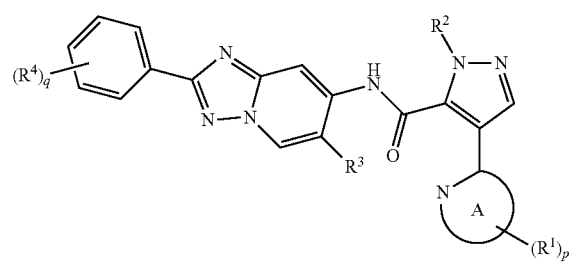

4 Claims, No Drawings

PYRAZOLE DERIVATIVE MANUFACTURING METHOD

CROSS-REFERENCE TO RELATED APPLICATIONS

This application is a Divisional of copending application Ser. No. 15/329,447, filed on Jan. 26, 2017, which is the National Phase under 35 U.S.C. § 371 of International Application No. PCT/JP2015/071536, filed on Jul. 29, 2015, which claims the benefit under 35 U.S.C. § 119(a) to Patent Application No. 2014-155538, filed in Japan on Jul. 30, 2014 and Patent Application No. 2014-189458, filed in Japan on Sep. 17, 2014, all of which are hereby expressly incorporated by reference into the present application.

TECHNICAL FIELD

The present invention relates to a method for manufacturing a 4-heteroaryl-N-(2-phenyl-[1,2,4]triazolo[1,5-a]pyridin-7-yl)-1H-pyrazole-5-carboxylic acid amide derivative represented by formula (I), which exhibits phosphodiesterase 10 (hereinafter shown as "PDE10") inhibitory activity; and an intermediate for this manufacturing method.

BACKGROUND ART

A 4-heteroaryl-N-(2-phenyl-[1,2,4]triazolo[1,5-a]pyridin-7-yl)-1H-pyrazole-5-carboxylic acid amide derivative represented by formula (I) exhibits excellent PDE10 inhibitory activity, is useful for treating and/or preventing a variety of symptoms of mental disorders linked to PDE10 (for example, paranoid type, disorganized type, catatonic type, undifferentiated and residual type schizophrenia, and the like), and has potential as a therapeutic agent having diminished adverse reactions.

As a method for manufacturing an N-([1,2,4]triazolo[1,5-a]pyridin-7-yl)-1H-pyrazole-5-carboxylic acid amide derivative (formula (i)), scheme 1 on page 26 of WO 2012/076430 (PTL 1) discloses a manufacturing method in which a carboxylic acid derivative (formula (ii)) and a 7-amino-[1,2,4]triazolo[1,5-a]pyridine derivative (formula (iii)) are subjected to a condensation reaction.

[C1]

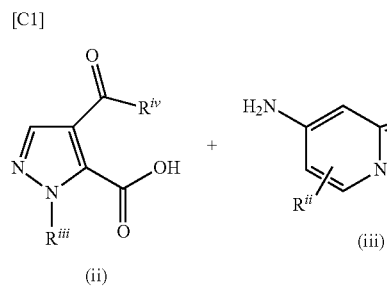

(ii)

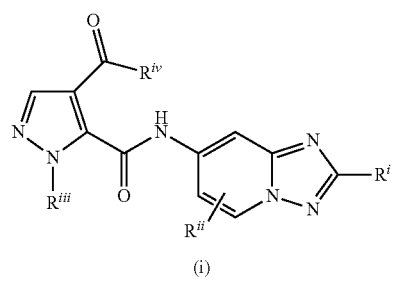

(i)

As a method for manufacturing a 4-heteroaryl-N-(2-phenyl-[1,2,4]triazolo[1,5-a]pyridin-7-yl)-1H-pyrazole-5-carboxylic acid amide derivative (formula (I-a)), page 184 of WO 2014/133046 (PTL 2) discloses a manufacturing method in which a carboxylic acid derivative (formula (CA)) and a 7-amino-[1,2,4]triazolo[1,5-a]pyridine derivative (formula (AM)) are subjected to a condensation reaction.

[C2]

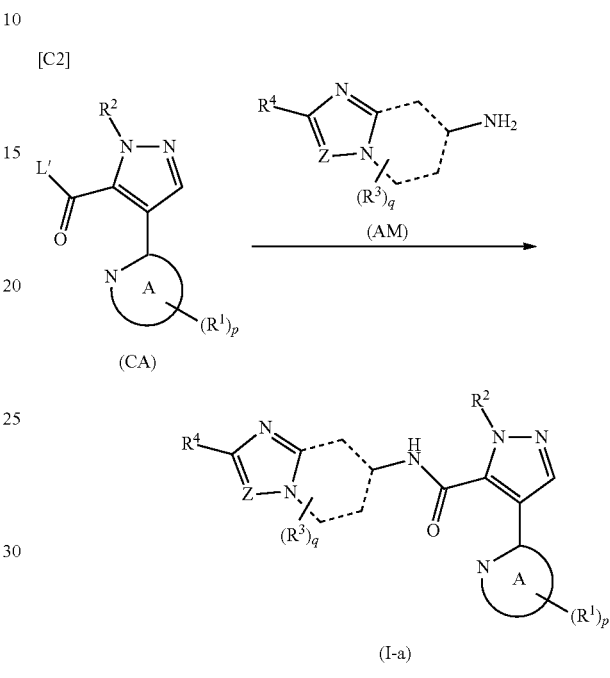

L' = OH, OM (M = Li, Na, K, etc), halogen

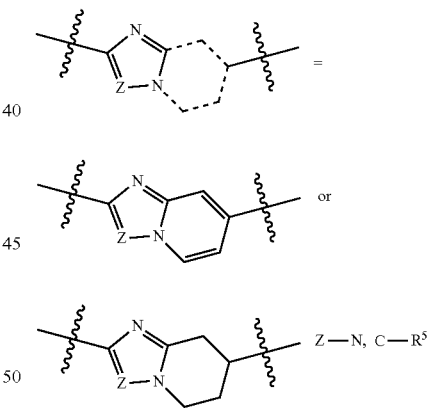

According to PTL 1, a compound represented by formula (iii) is manufactured using O-(mesitylsulfonyl)hydroxylamine (formula (v)).

[C3]

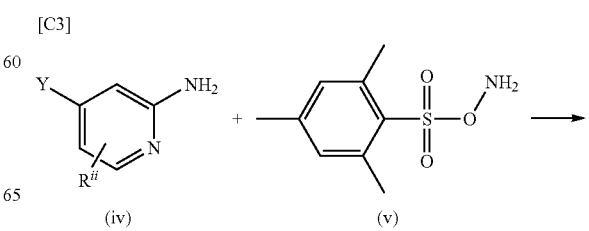

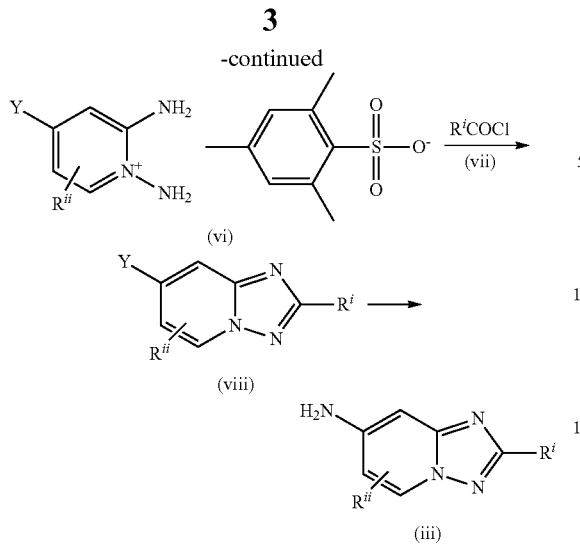

A compound represented by formula (I) in the present invention can be manufactured using a compound represented by formula (iii) disclosed in PTL 1, but in cases where a compound represented by formula (iii) is manufactured according to the manufacturing method disclosed in PTL 1, it is essential to use the compound represented by formula (v). However, it has been pointed out that the compound represented by formula (v) is not suitable for use in large scale synthesis or industrial manufacturing due to problems relating to the stability and safety of the compound (see NPL 1). Therefore, in cases where large scale synthesis or industrial manufacturing of a compound represented by formula (I) is being considered, it is essential to find a novel manufacturing method that is different from the manufacturing method disclosed in PTL 1.

Meanwhile, a method for manufacturing an analogous compound to formula (iii) (formula (iii-1)) is disclosed in WO 2013/117610 (PTL 3). However, the yield of a compound having a $R^v=NH_2$ group is low, at 28%, and there are no synthesis examples of 6,7-2 substituted [1,2,4]triazolo[1,5-a]pyridine derivatives.

[C4]

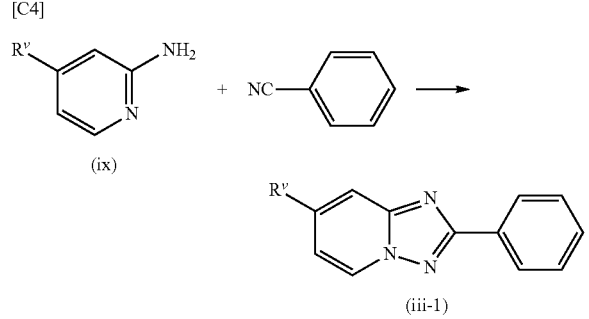

$R^v$ = H, Br, $NH_2$, Cl, I, OBn

In addition, no manufacturing method is known whereby a 6-fluoro-7-amino-4-phenyl-[1,2,4]triazolo[1,5-a]pyridine derivative, which is a partial structure of a 4-heteroaryl-N-(2-phenyl-[1,2,4]triazolo[1,5-a]pyridin-7-yl)-1H-pyrazole-5-carboxylic acid amide derivative represented by formula (I), can be synthesized in large quantities with good efficiency.

Therefore, there is a need to overcome these problems and establish an efficient manufacturing method that is suitable for large scale synthesis or industrial manufacturing of a compound represented by formula (I).

CITATION LIST

Patent Literature

[PTL 1] WO 2012/076430
[PTL 2] WO 2014/133046
[PTL 3] WO 2013/117610

Non Patent Literature

[NPL 1] Organic Process Research & Development, 13, pages 263-267, 2009.

SUMMARY OF INVENTION

Technical Problem

The purpose of the present invention is to provide an efficient manufacturing method that is suitable for large scale synthesis or industrial manufacturing of a 4-heteroaryl-N-(2-phenyl-[1,2,4]triazolo[1,5-a]pyridin-7-yl)-1H-pyrazole-5-carboxylic acid amide derivative represented by formula (I), and especially a novel manufacturing method by which a compound represented by formula (I) is manufactured without using a 7-amino-[1,2,4]triazolo[1,5-a]pyridine derivative represented by formula (iii) when obtaining this derivative in large scale or industrial manufacturing; and an intermediate that is useful for this manufacturing method.

Solution to Problem

The inventors of the present invention have carried out diligent research in order to solve this problem. As a result, the inventors of the present invention found a method for easily manufacturing a 4-heteroaryl-N-(2-phenyl-[1,2,4]triazolo[1,5-a]pyridin-7-yl)-1H-pyrazole-5-carboxylic acid amide derivative represented by formula (I) below in a short process and with a good yield, and thereby completed the present invention on the basis of these findings.

[C5]

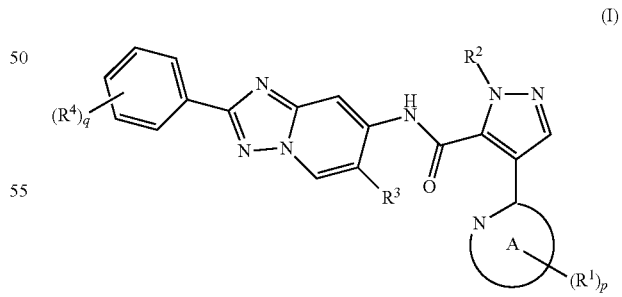

(The definitions of p, q, $R^1$, $R^2$, $R^3$, $R^4$ and ring A group in formula (I) are explained in mode [1] below.)

Advantageous Effects of Invention

The present invention is a method for manufacturing a 4-heteroaryl-N-(2-phenyl-[1,2,4]triazolo[1,5-a]pyridin-7- yl)-1H-pyrazole-5-carboxylic acid amide derivative represented by formula (I) below, which exhibits PDE10 inhibitory activity; and an intermediate that is useful for this manufacturing method. The present invention can provide a manufacturing method which has a good yield and a short process and is simple and industrially advantageous, and is industrially useful.

DESCRIPTION OF EMBODIMENTS

[Modes of the Present Invention]

The present invention is a method for manufacturing a 4-heteroaryl-N-(2-phenyl-[1,2,4]triazolo[1,5-a]pyridin-7-yl)-1H-pyrazole-5-carboxylic acid amide derivative represented by formula (I), which is illustrated in the modes below; and an intermediate that is useful for this manufacturing method, and is described below.

[1] A first mode of the present invention is a method for manufacturing a compound represented by formula (I) below:

[C6]

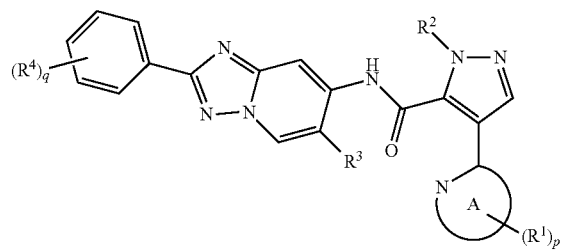
(I)

[in formula (I), p denotes an integer between 0 and 3; q denotes an integer between 0 and 2; $R^1$ s independently denote a group arbitrarily selected from among a halogen atom, a cyano group, a $C_{1-6}$ alkyl group, a halogenated $C_{1-6}$ alkyl group and a $C_{1-6}$ alkoxy group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C7]

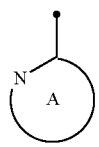
(II)

denotes a monocyclic 5- to 6-membered heteroaryl group arbitrarily selected from among a pyridin-2-yl group, a pyridazin-3-yl group, a pyrimidin-2-yl group, a pyrimidin-4-yl group and a pyrazin-2-yl group], the manufacturing method including stages in which a compound represented by formula (ET-1):

[C8]

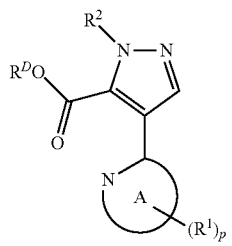
(ET-1)

[in formula (ET-1), p, $R^1$, $R^2$ and ring A group represented by formula (II) are defined in the same way as for formula (I) in mode [1]; $R^D$ denotes a group arbitrarily selected from among a $C_{1-6}$ alkyl group, a $C_{6-14}$ aryl group and a $C_{7-20}$ aralkyl group (a routine method for manufacturing a compound represented by formula (ET-1) is described later)] and an aqueous ammonia solution are reacted with each other at a temperature between 0° C. and a temperature at which the reaction solution refluxes, thereby obtaining a compound represented by formula (AD-1):

[C9]

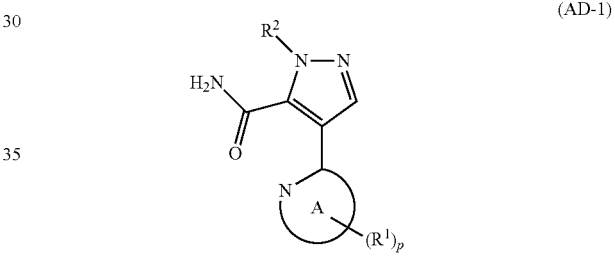
(AD-1)

[in formula (AD-1), p, $R^1$, $R^2$ and ring A group represented by formula (II) are defined in the same way as for formula (I) in mode [1]] (stage [1]-1), the compound represented by formula (AD-1) and a 2-amino-4-iodopyridine derivative represented by formula (PY-1):

[C10]

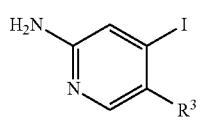
(PY-1)

[in formula (PY-1), $R^3$ denotes a group arbitrarily selected from among a hydrogen atom and a fluorine atom (a routine method for manufacturing a compound represented by formula (PY-1) is described later)] are reacted with each other in the presence of N,N-dimethyl-1,2-ethanediamine, copper iodide and an inorganic base such as potassium carbonate or potassium phosphate using a solvent which does not take part in the reaction, such as 1,4-dioxane, tetrahydrofuran or 1,2-dimethoxyethane, at a temperature between 0° C. and a temperature at which the solvent refluxes, thereby obtaining a compound represented by formula (AD-2):

[C11]

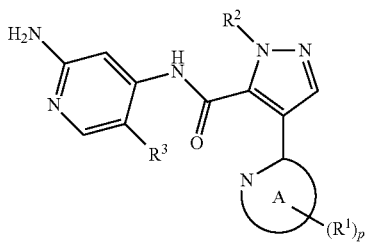

(AD-2)

[in formula (AD-2), p, $R^1$, $R^2$, $R^3$ and ring A group represented by formula (II) are defined in the same way as for formula (I) in mode [1]] (stage [1]-2), the compound represented by formula (AD-2) and a compound represented by formula (IM-1):

[C12]

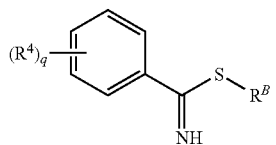

(IM-1)

[in formula (IM-1), q and $R^4$ are defined in the same way as for formula (I) above; and $R^B$ denotes a $C_{1-6}$ alkyl group] or a salt thereof (the compound represented by formula (IM-1) and salt thereof are commercially available compounds or compounds that can be easily obtained from commercially available compounds using manufacturing methods known from literature) are reacted with each other using a solvent which does not take part in the reaction, such as dimethyl sulfoxide or pyridine, at a temperature between 0° C. and a temperature at which the solvent refluxes, thereby obtaining a compound represented by formula (AD-3):

[C13]

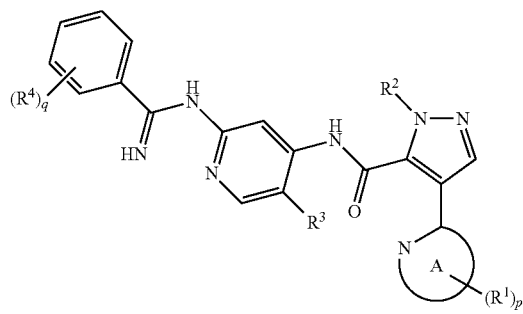

(AD-3)

[in formula (AD-3), p, q, $R^1$, $R^2$, $R^3$, $R^4$ and ring A group represented by formula (II) are defined in the same way as for formula (I) in mode [1]] (stage [1]-3), and the compound represented by formula (AD-3) is subjected to a cyclization reaction in the presence of air using a solvent which does not take part in the reaction, such as dimethyl sulfoxide (DMSO) or N-methylpyrrolidone (NMP), at a temperature between 0° C. and a temperature at which the solvent refluxes in the presence of a copper reagent such as copper iodide (CuI) or copper chloride (CuCl) (stage [1]-4), thereby obtaining the compound represented by formula (I).

[1-1] A preferred aspect of mode [1] is a method in which a compound represented by formula (I) above is manufactured [in formula (I), p, q, $R^3$ and ring A group represented by formula (II) are defined in the same way as for mode [1] above; $R^1$ denotes a group arbitrarily selected from among a fluorine atom, a chlorine atom, a cyano group, a methyl group, a trifluoromethyl group and a methoxy group; $R^2$ denotes a methyl group; and $R^4$ denotes a group arbitrarily selected from among a fluorine atom, a methyl group and a methoxy group], the manufacturing method including stages in which a compound represented by formula (I) is obtained [these stages are the same as (stage [1]-1) to (stage [1]-4) in mode [1] above; the definitions of the substituent groups in the intermediates in (stage [1]-1) to (stage [1]-4) are the same as the definitions in mode [1-1], and $R^B$ in formula (IM-1) is a $C_{1-6}$ alkyl group].

[1-2] A more preferred aspect of mode [1] is a method in which a compound represented by formula (I) above is manufactured [in formula (I), p, $R^1$, $R^2$, $R^4$ and ring A group represented by formula (II) are defined in the same way as for mode [1-1] above; q denotes the integer 0; and $R^3$ denotes a fluorine atom], the manufacturing method including stages in which a compound represented by formula (I) is obtained [these stages are the same as (stage [1]-1) to (stage [1]-4) in mode [1] above; the definitions of the substituent groups in the intermediates in (stage [1]-1) to (stage [1]-4) are the same as the definitions in mode [1-2], and $R^B$ in formula (IM-1) is a $C_{1-6}$ alkyl group].

[1-3] A yet more preferred aspect of mode [1] is a method in which a compound represented by formula (I) above is manufactured [in formula (I), p, q, $R^1$, $R^2$, $R^3$ and $R^4$ are defined in the same way as for mode [1-2] above; ring A group represented by formula (II) is a pyrimidin-4-yl group; and a more specific group obtained by combining the definitions of p, $R^1$ and ring A group represented by formula (II) is a 2,5-dimethylpyrimidin-4-yl group], the manufacturing method including stages in which a compound represented by formula (I) is obtained [these stages are the same as (stage [1]-1) to (stage [1]-4) in mode [1] above; the definitions of the substituent groups in the intermediates in (stage [1]-1) to (stage [1]-4) are the same as the definitions in mode [1-3], and $R^B$ in formula (IM-1) is a $C_{1-6}$ alkyl group].

[1a] Another aspect of the first mode of the present invention is a method for manufacturing a compound represented by formula (I) below:

[C14]

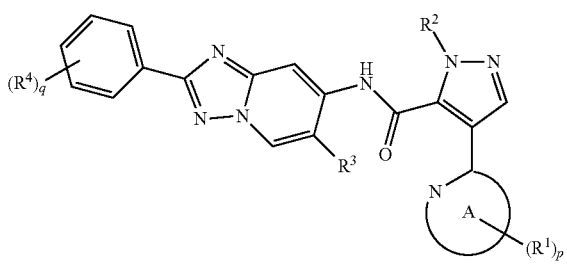

(I)

[in formula (I), p denotes an integer between 0 and 3; q denotes an integer between 0 and 2; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C15]

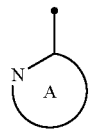

(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], the manufacturing method including stages in which a compound represented by formula (ET-1):

[C16]

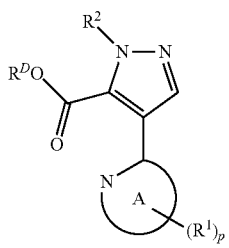

(ET-1)

[in formula (ET-1), p, $R^1$, $R^2$ and ring A group represented by formula (II) are defined in the same way as for formula (I) in mode [1a]; $R^D$ denotes a group arbitrarily selected from among a $C_{1-6}$ alkyl group, a $C_{6-14}$ aryl group and a $C_{7-20}$ aralkyl group (a routine method for manufacturing a compound represented by formula (ET-1) is described later)] and an aqueous ammonia solution are reacted with each other at a temperature between 0° C. and a temperature at which the reaction solution refluxes, thereby obtaining a compound represented by formula (AD-1):

[C17]

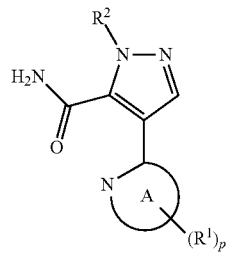

(AD-1)

[in formula (AD-1), p, $R^1$, $R^2$ and ring A group represented by formula (II) are defined in the same way as for formula (I) in mode [1a]] (stage [1a]-1), the compound represented by formula (AD-1) and a 2-amino-4-iodopyridine derivative represented by formula (PY-1):

[C18]

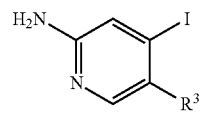

(PY-1)

[in formula (PY-1), $R^3$ denotes a group arbitrarily selected from among a hydrogen atom and a fluorine atom (a routine method for manufacturing a compound represented by formula (PY-1) is described later)] are reacted with each other in the presence of N,N-dimethyl-1,2-ethanediamine, copper iodide (CuI) and an inorganic base such as potassium carbonate or potassium phosphate using a solvent which does not take part in the reaction, such as 1,4-dioxane, tetrahydrofuran or 1,2-dimethoxyethane, at a temperature between 0° C. and a temperature at which the solvent refluxes, thereby obtaining a compound represented by formula (AD-2):

[C19]

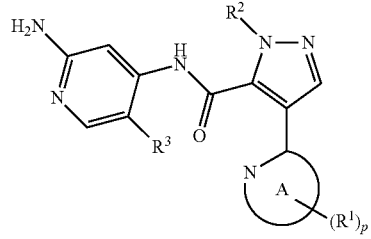

(AD-2)

[in formula (AD-2), p, $R^1$, $R^2$, $R^3$ and ring A group represented by formula (II) are defined in the same way as for formula (I) in mode [1a]] (stage [1a]-2), the compound represented by formula (AD-2) and a compound represented by formula (IM-1):

[C20]

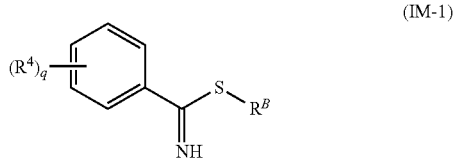

(IM-1)

[in formula (IM-1), q and $R^4$ are defined in the same way as for formula (I) in mode [1a]; and $R^B$ denotes a $C_{1-6}$ alkyl group] or a salt thereof (the compound represented by formula (IM-1) and salt thereof are commercially available compounds or compounds that can be easily obtained from commercially available compounds using manufacturing methods known from literature) are reacted with each other using a solvent which does not take part in the reaction, such as dimethyl sulfoxide or pyridine, at a temperature between 0° C. and a temperature at which the solvent refluxes, thereby obtaining a compound represented by formula (AD-3):

[C21]

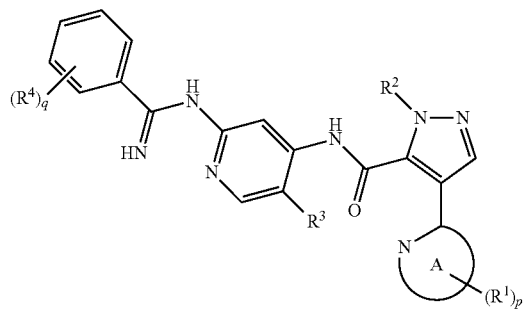

(AD-3)

[in formula (AD-3), p, q, $R^1$, $R^2$, $R^3$, $R^4$ and ring A group represented by formula (II) are defined in the same way as for formula (I) in mode [1a]] (stage [1a]-3), and the compound represented by formula (AD-3) is subjected to a cyclization reaction in the presence of air using a solvent which does not take part in the reaction, such as dimethyl sulfoxide (DMSO) or N-methylpyrrolidone (NMP), at a temperature between 0° C. and a temperature at which the solvent refluxes in the presence of a copper reagent such as copper iodide (CuI) or copper chloride (CuCl) (stage [1a]-4), thereby obtaining the compound represented by formula (I).

[1a-1] A preferred aspect of mode [1a] is a method in which a compound represented by formula (I) above is manufactured [in formula (I), p, q, $R^3$ and ring A group represented by formula (II) are defined in the same way as in mode [1a] above; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; $R^2$ denotes a methyl group; and $R^4$ denotes a group arbitrarily selected from among a fluorine atom, a methyl group and a methoxy group], the manufacturing method including stages in which a compound represented by formula (I) is obtained [these stages are the same as (stage [1a]-1) to (stage [1a]-4) in mode [1a] above; the definitions of the substituent groups in the intermediates in (stage [1a]-1) to (stage [1a]-4) are the same as the definitions in mode [1a-1], and $R^B$ in formula (IM-1) is a $C_{1-6}$ alkyl group].

[1a-2] A more preferred aspect of mode [1a] is a method in which a compound represented by formula (I) above is manufactured [in formula (I), p, $R^1$, $R^2$, $R^4$ and ring A group represented by formula (II) are defined in the same way as for mode [1a-1] above; q denotes the integer 0; and $R^3$ denotes a fluorine atom], the manufacturing method including stages in which a compound represented by formula (I) is obtained [these stages are the same as (stage [1a]-1) to (stage [1a]-4) in mode [1a] above; the definitions of the substituent groups in the intermediates in (stage [1a]-1) to (stage [1a]-4) are the same as the definitions in mode [1a-2], and $R^B$ in formula (IM-1) is a $C_{1-6}$ alkyl group].

[1a-3] A yet more preferred aspect of mode [1a] is a method in which a compound represented by formula (I) above is manufactured [in formula (I), p, q, $R^1$, $R^2$, $R^3$ and $R^4$ are defined in the same way as for mode [1a-2] above; ring A group represented by formula (II) is a thiazol-2-yl group or a pyrimidin-4-yl group; and a more specific group obtained by combining the definitions of p, $R^1$ and ring A group represented by formula (II) is a 4-(trifluoromethyl)thiazol-2-yl group, a 5-fluoro-2-methoxypyrimidin-4-yl group, a 2,5-dimethylpyrimidin-4-yl group or a 2-methylpyrimidin-4-yl group], the manufacturing method including stages in which a compound represented by formula (I) is obtained [these stages are the same as (stage [1a]-1) to (stage [1a]-4) in mode [1a] above; the definitions of the substituent groups in the intermediates in (stage [1a]-1) to (stage [1a]-4) are the same as the definitions in mode [1a-3], and $R^B$ in formula (IM-1) is a $C_{1-6}$ alkyl group].

[2] A second mode of the present invention is formula (AD-2) below:

[C22]

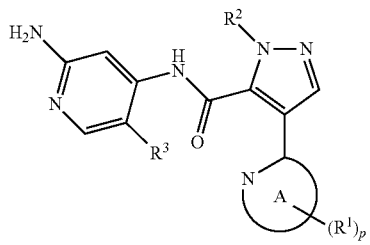

(AD-2)

[in formula (AD-2), p denotes an integer between 0 and 3; $R^1$ groups each independently denote a group arbitrarily selected from among a halogen atom, a cyano group, a $C_{1-6}$ alkyl group, a halogenated $C_{1-6}$ alkyl group and a $C_{1-6}$ alkoxy group; $R^2$ denotes a $C_{1-6}$ alkyl group; $R^3$ denotes a group arbitrarily selected from among a hydrogen atom and a fluorine atom; and ring A group represented by formula (II):

[C23]

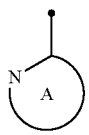
(II)

denotes a monocyclic 5- to 6-membered heteroaryl group arbitrarily selected from among a pyridin-2-yl group, a pyridazin-3-yl group, a pyrimidin-2-yl group, a pyrimidin-4-yl group and a pyrazin-2-yl group], the manufacturing method including stages in which a compound represented by formula (ET-1):

[C24]

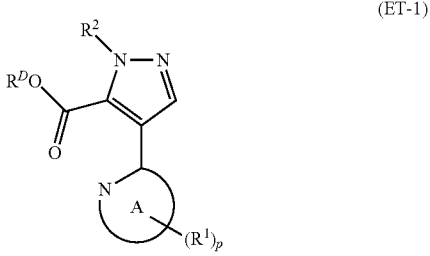
(ET-1)

[in formula (ET-1), p, $R^1$, $R^2$ and ring A group represented by formula (II) are defined in the same way as for formula (AD-2) in mode [2]; $R^D$ denotes a group arbitrarily selected from among a $C_{1-6}$ alkyl group, a $C_{6-14}$ aryl group and a $C_{7-20}$ aralkyl group (a routine method for manufacturing a compound represented by formula (ET-1) is described later)] and an aqueous ammonia solution are reacted with each other at a temperature between 0° C. and a temperature at which the reaction solution refluxes, thereby obtaining a compound represented by formula (AD-1):

[C25]

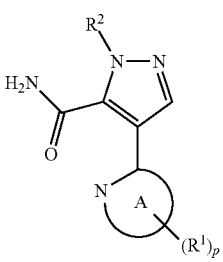
(AD-1)

[in formula (AD-1), p, $R^1$, $R^2$ and ring A group represented by formula (II) are defined in the same way as for formula (AD-2) in mode [2]] (stage [2]-1), and the compound represented by formula (AD-1) and a 2-amino-4-iodopyridine derivative represented by formula (PY-1):

[C26]

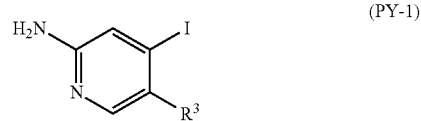
(PY-1)

[in formula (PY-1), $R^3$ denotes a hydrogen atom or a fluorine atom (a routine method for manufacturing a compound represented by formula (PY-1) is described later)] are reacted with each other in the presence of N,N-dimethyl-1,2-ethanediamine, copper iodide and an inorganic base such as potassium carbonate or potassium phosphate using a solvent which does not take part in the reaction, such as 1,4-dioxane, tetrahydrofuran or 1,2-dimethoxyethane, at a temperature between 0° C. and a temperature at which the solvent refluxes, thereby obtaining a compound represented by formula (AD-2) (stage [2]-2).

[2-1] A preferred aspect of mode [2] is a method in which a compound represented by formula (AD-2) above is manufactured [in formula (AD-2), p, $R^3$ and ring A group represented by formula (II) are defined in the same way as in mode [2] above; $R^1$ denotes a group arbitrarily selected from among a fluorine atom, a chlorine atom, a cyano group, a methyl group, a trifluoromethyl group and a methoxy group; and $R^2$ denotes a methyl group], the manufacturing method including stages in which a compound represented by formula (AD-2) is obtained [these stages are the same as (stage [2]-1) and (stage [2]-2) in mode [2] above; and the definitions of the substituent groups in the intermediates in (stage [2]-1) and (stage [2]-2) are the same as the definitions in mode [2-1]].

[2-2] A more preferred aspect of mode [2] is a method in which a compound represented by formula (AD-2) above is manufactured [in formula (AD-2), p, $R^1$, $R^2$ and ring A group represented by formula (II) are defined in the same way as in mode [2-1] above; and $R^3$ denotes a fluorine atom], the manufacturing method including stages in which a compound represented by formula (AD-2) is obtained [these stages are the same as (stage [2]-1) and (stage [2]-2) in mode [2] above; and the definitions of the substituent groups in the intermediates in (stage [2]-1) and (stage [2]-2) are the same as the definitions in mode [2-2]].

[2-3] A yet more preferred aspect of mode [2] is a method in which a compound represented by formula (AD-2) above is manufactured [in formula (AD-2), p, $R^1$, $R^2$ and $R^3$ are defined in the same way as for mode [2-2] above; ring A group represented by formula (II) is a pyrimidin-4-yl group; and a more specific group obtained by combining the definitions of p, $R^1$ and ring A group represented by formula (II) is a 2,5-dimethylpyrimidin-4-yl group], the manufacturing method including stages in which a compound represented by formula (AD-2) is obtained [these stages are the same as (stage [2]-1) and (stage [2]-2) in mode [2] above; and the definitions of the substituent groups in the intermediates in (stage [2]-1) and (stage [2]-2) are the same as the definitions in mode [2-3]].

[2a] Another aspect of the second mode of the present invention is a method for manufacturing a compound represented by formula (AD-2) below:

[C27]

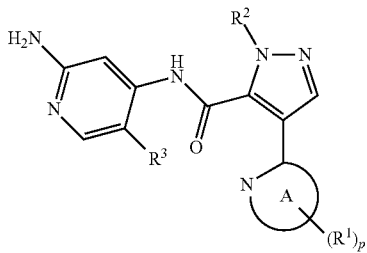

(AD-2)

[in formula (AD-2), p denotes an integer between 0 and 3; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; and ring A group represented by formula (II):

[C28]

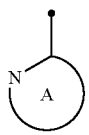

(II)

denotes a monocyclic 5- to 6-membered heteroaryl group arbitrarily selected from among a thiazol-2-yl group, a thiazol-4-yl group, a 1-methyl-1H-imidazol-2-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], the manufacturing method including stages in which a compound represented by formula (ET-1):

[C29]

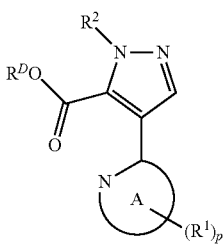

(ET-1)

[in formula (ET-1), p, $R^1$, $R^2$ and ring A group represented by formula (II) are defined in the same way as for formula (AD-2) in mode [2a]; $R^D$ denotes a group arbitrarily selected from among a $C_{1-6}$ alkyl group, a $C_{6-14}$ aryl group and a $C_{7-20}$ aralkyl group (a routine method for manufacturing a compound represented by formula (ET-1) is described later)] and an aqueous ammonia solution are reacted with each other at a temperature between 0° C. and a temperature at which the reaction solution refluxes, thereby obtaining a compound represented by formula (AD-1):

[C30]

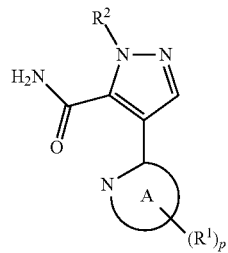

(AD-1)

[in formula (AD-1), p, $R^1$, $R^2$ and ring A group represented by formula (II) are defined in the same way as for formula (AD-2) in mode [2a]] (stage [2a]-1), and the compound represented by formula (AD-1) and a 2-amino-4-iodopyridine derivative represented by formula (PY-1):

[C31]

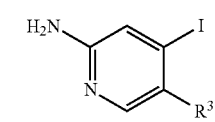

(PY-1)

[in formula (PY-1), $R^3$ denotes a hydrogen atom or a fluorine atom (a routine method for manufacturing a compound represented by formula (PY-1) is described later)] are reacted with each other in the presence of N,N-dimethyl-1,2-ethanediamine, copper iodide (CuI) and an inorganic base such as potassium carbonate or potassium phosphate using a solvent which does not take part in the reaction, such as 1,4-dioxane, tetrahydrofuran or 1,2-dimethoxyethane, at a temperature between 0° C. and a temperature at which the solvent refluxes, thereby obtaining the compound represented by formula (AD-2) (stage [2a]-2).

[2a-1] A preferred aspect of mode [2a] is a method in which a compound represented by formula (AD-2) above is manufactured [in formula (AD-2), p, $R^3$ and ring A group represented by formula (II) are defined in the same way as in mode [2a] above; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; and $R^2$ denotes a methyl group], the manufacturing method including stages in which a compound represented by formula (AD-2) is obtained [these stages are the same as (stage [2a]-1) and (stage [2a]-2) in mode [2a] above; and the definitions of the substituent groups in the intermediates in (stage [2a]-1) and (stage [2a]-2) are the same as the definitions in mode [2a-1]].

[2a-2] A more preferred aspect of mode [2a] is a method in which a compound represented by formula (AD-2) above is manufactured [in formula (AD-2), p, $R^1$, $R^2$ and ring A group represented by formula (II) are defined in the same way as in mode [2a-1] above; and $R^3$ denotes a fluorine atom], the manufacturing method including stages in which a compound represented by formula (AD-2) is obtained [these stages are the same as (stage [2a]-1) and (stage [2a]-2) in mode [2a] above; and the definitions of the substituent groups in the intermediates in (stage [2a]-1) and (stage [2a]-2) are the same as the definitions in mode [2a-2]].

[2a-3] A yet more preferred aspect of mode [2a] is a method in which a compound represented by formula (AD-2) above is manufactured [in formula (AD-2), p, R¹, R² and R³ are defined in the same way as for mode [2a-2] above; ring A group represented by formula (II) is a thiazol-2-yl group or a pyrimidin-4-yl group; and a more specific group obtained by combining the definitions of p, R¹ and ring A group represented by formula (II) is a 4-(trifluoromethyl)thiazol-2-yl group, a 5-fluoro-2-methoxypyrimidin-4-yl group, a 2,5-dimethylpyrimidin-4-yl group or a 2-methylpyrimidin-4-yl group], the manufacturing method including stages in which a compound represented by formula (AD-2) is obtained [these stages are the same as (stage [2a]-1) and (stage [2a]-2) in mode [2a] above; and the definitions of the substituent groups in the intermediates in (stage [2a]-1) and (stage [2a]-2) are the same as the definitions in mode [2a-3]].

[3] A third mode of the present invention is a method for manufacturing a compound represented by formula (AD-2) below:

[C32]

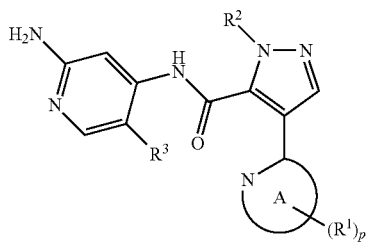

(AD-2)

[in formula (AD-2), p denotes an integer between 0 and 3; R¹ groups each independently denote a group arbitrarily selected from among a halogen atom, a cyano group, a $C_{1-6}$ alkyl group, a halogenated $C_{1-6}$ alkyl group and a $C_{1-6}$ alkoxy group; R² denotes a $C_{1-6}$ alkyl group; R³ denotes a group arbitrarily selected from among a hydrogen atom and a fluorine atom; and ring A group represented by formula (II):

[C33]

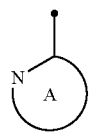

(II)

denotes a monocyclic 5- to 6-membered heteroaryl group arbitrarily selected from among a pyridin-2-yl group, a pyridazin-3-yl group, a pyrimidin-2-yl group, a pyrimidin-4-yl group and a pyrazin-2-yl group], the manufacturing method including a stage in which a compound represented by formula (AD-1):

[C34]

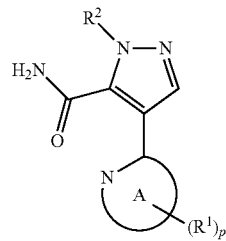

(AD-1)

[in formula (AD-1), p, R¹, R² and ring A group represented by formula (II) are defined in the same way as for formula (AD-2) in mode [3]] and a 2-amino-4-iodopyridine derivative represented by formula (PY-1):

[C35]

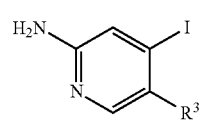

(PY-1)

[in formula (PY-1), R³ denotes a hydrogen atom or a fluorine atom (a routine method for manufacturing a compound represented by formula (PY-1) is described later)] are reacted with each other in the presence of N,N-dimethyl-1,2-ethanediamine, copper iodide (CuI) and an inorganic base such as potassium carbonate or potassium phosphate using a solvent which does not take part in the reaction, such as 1,4-dioxane, tetrahydrofuran or 1,2-dimethoxyethane, at a temperature between 0° C. and a temperature at which the solvent refluxes, thereby obtaining the compound represented by formula (AD-2) (stage [3]-1).

[3-1] A preferred aspect of mode [3] is a method in which a compound represented by formula (AD-2) above is manufactured [in formula (AD-2), p, R³ and ring A group represented by formula (II) are defined in the same way as in mode [3] above; R¹ denotes a group arbitrarily selected from among a fluorine atom, a chlorine atom, a cyano group, a methyl group, a trifluoromethyl group and a methoxy group; and R² denotes a methyl group], the manufacturing method including a stage in which a compound represented by formula (AD-2) is obtained [this stage is the same as (stage [3]-1) in mode [3] above; and the definitions of the substituent groups in the intermediate in (stage [3]-1) are the same as the definitions in mode [3-1]].

[3-2] A more preferred aspect of mode [3] is a method in which a compound represented by formula (AD-2) above is manufactured [in formula (AD-2), p, R¹, R² and ring A group represented by formula (II) are defined in the same way as in mode [3-1] above; and R³ denotes a fluorine atom], the manufacturing method including a stage in which a compound represented by formula (AD-2) is obtained [this stage is the same as (stage [3]-1) in mode [3] above; and the definitions of the substituent groups in the intermediate in (stage [3]-1) are the same as the definitions in mode [3-2]].

[3-3] A yet more preferred aspect of mode [3] is a method in which a compound represented by formula (AD-2) above is manufactured [in formula (AD-2), p, $R^1$, $R^2$ and $R^3$ are defined in the same way as for mode [3-2] above; ring A group represented by formula (II) is a pyrimidin-4-yl group; and a more specific group obtained by combining the definitions of p, $R^1$ and ring A group represented by formula (II) is a 2,5-dimethylpyrimidin-4-yl group], the manufacturing method including a stage in which a compound represented by formula (AD-2) is obtained [this stage is the same as (stage [3]-1) in mode [3] above; and the definitions of the substituent groups in the intermediate in (stage [3]-1) are the same as the definitions in mode [3-3]].

[3a] Another aspect of the third mode of the present invention is a method for manufacturing a compound represented by formula (AD-2) below:

[C36]

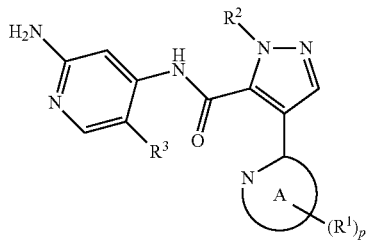

(AD-2)

[in formula (AD-2), p denotes an integer between 0 and 3; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; and ring A group represented by formula (II):

[C37]

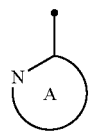

(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], the manufacturing method including a stage in which a compound represented by formula (AD-1):

[C38]

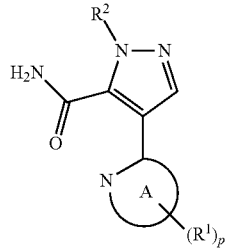

(AD-1)

[in formula (AD-1), p, $R^1$, $R^2$ and ring A group represented by formula (II) are defined in the same way as for formula (AD-2) in mode [3a]] and a 2-amino-4-iodopyridine derivative represented by formula (PY-1):

[C39]

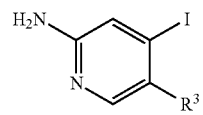

(PY-1)

[in formula (PY-1), $R^3$ denotes a hydrogen atom or a fluorine atom (a routine method for manufacturing a compound represented by formula (PY-1) is described later)] are reacted with each other in the presence of N,N-dimethyl-1,2-ethanediamine, copper iodide and an inorganic base such as potassium carbonate or potassium phosphate using a solvent which does not take part in the reaction, such as 1,4-dioxane, tetrahydrofuran or 1,2-dimethoxyethane, at a temperature between 0° C. and a temperature at which the solvent refluxes, thereby obtaining the compound represented by formula (AD-2) (stage [3a]-1).

[3a-1] A preferred aspect of mode [3a] is a method in which a compound represented by formula (AD-2) above is manufactured [in formula (AD-2), p, $R^3$ and ring A group represented by formula (II) are defined in the same way as in mode [3a] above; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; and $R^2$ denotes a methyl group], the manufacturing method including a stage in which a compound represented by formula (AD-2) is obtained [this stage is the same as (stage [3a]-1) in mode [3a] above; and the definitions of the substituent groups in the intermediate in (stage [3a]-1) are the same as the definitions in mode [3a-1]].

[3a-2] A more preferred aspect of mode [3a] is a method in which a compound represented by formula (AD-2) above is manufactured [in formula (AD-2), p, $R^1$, $R^2$ and ring A group represented by formula (II) are defined in the same way as in mode [3a-1] above; and $R^3$ denotes a fluorine atom], the manufacturing method including a stage in which a compound represented by formula (AD-2) is obtained [this stage is the same as (stage [3a]-1) in mode [3a] above; and the definitions of the substituent groups in the intermediate in (stage [3a]-1) are the same as the definitions in mode [3a-2]].

[3a-3] A yet more preferred aspect of mode [3a] is a method in which a compound represented by formula (AD-2) above is manufactured [in formula (AD-2), p, $R^1$, $R^2$ and $R^3$ are defined in the same way as for mode [3a-2] above; ring A group represented by formula (II) is a thiazol-2-yl group or a pyrimidin-4-yl group; and a more specific group obtained by combining the definitions of p, $R^1$ and ring A group represented by formula (II) is a 4-(trifluoromethyl) thiazol-2-yl group, a 5-fluoro-2-methoxypyrimidin-4-yl group, a 2,5-dimethylpyrimidin-4-yl group or a 2-methyl-pyrimidin-4-yl group], the manufacturing method including a stage in which a compound represented by formula (AD-2) is obtained [this stage is the same as (stage [3a]-1) in mode [3a] above; and the definitions of the substituent groups in the intermediate in (stage [3a]-1) are the same as the definitions in mode [3a-3]].

[4] A fourth mode of the present invention is a method for manufacturing a compound represented by formula (I) below:

[C40]

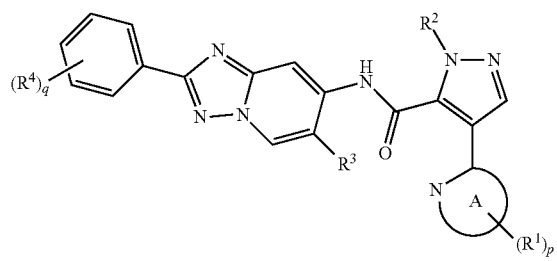

(I)

[in formula (I), p denotes an integer between 0 and 3; q denotes an integer between 0 and 2; $R^1$ groups each independently denote a group arbitrarily selected from among a halogen atom, a cyano group, a $C_{1-6}$ alkyl group, a halogenated $C_{1-6}$ alkyl group and a $C_{1-6}$ alkoxy group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C41]

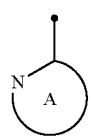

(II)

denotes a monocyclic 5- to 6-membered heteroaryl group arbitrarily selected from among a pyridin-2-yl group, a pyridazin-3-yl group, a pyrimidin-2-yl group, a pyrimidin-4-yl group and a pyrazin-2-yl group], the manufacturing method including stages in which a compound represented by formula (AD-2):

[C42]

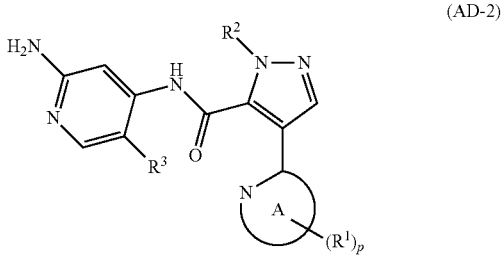

(AD-2)

[in formula (AD-2), p, $R^1$, $R^2$, $R^3$ and ring A group represented by formula (II) are defined in the same way as for formula (I) in mode [4]] and a compound represented by formula (IM-1):

[C43]

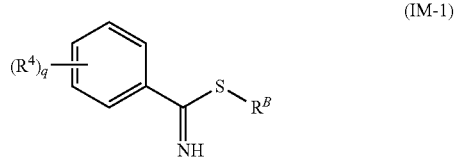

(IM-1)

[in formula (IM-1), q and $R^4$ are defined in the same way as for formula (I) in mode [4]; and $R^B$ denotes a $C_{1-6}$ alkyl group] or a salt thereof (the compound represented by formula (IM-1) and salt thereof are commercially available compounds or compounds that can be easily obtained from commercially available compounds using manufacturing methods known from literature) are reacted with each other using a solvent which does not take part in the reaction, such as dimethyl sulfoxide or pyridine, at a temperature between 0° C. and a temperature at which the solvent refluxes thereby obtaining a compound represented by formula (AD-3):

[C44]

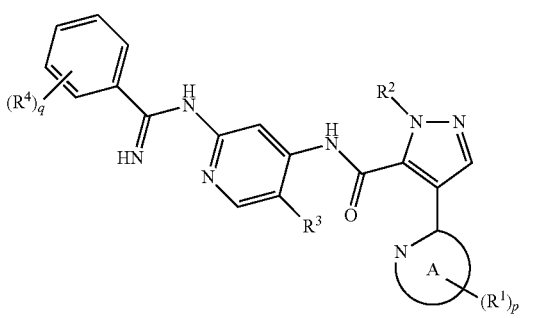

(AD-3)

[in formula (AD-3), p, q, $R^1$, $R^2$, $R^3$, $R^4$ and ring A group represented by formula (II) are defined in the same way as for formula (I) in mode [4]] (stage [4]-1), and the compound represented by formula (AD-3) is subjected to a cyclization reaction in the presence of air using a solvent which does not take part in the reaction, such as dimethyl sulfoxide (DMSO) or N-methylpyrrolidone (NMP), at a temperature between 0° C. and a temperature at which the solvent refluxes in the presence of a copper reagent such as copper iodide (CuI) or copper chloride (CuCl) (stage [4]-2), thereby obtaining the compound represented by formula (I).

[4-1] A preferred aspect of mode [4] is a method in which a compound represented by formula (I) above is manufactured [in formula (I), p, q, $R^3$ and ring A group represented by formula (II) are defined in the same way as for mode [4] above; $R^1$ denotes a group arbitrarily selected from among a fluorine atom, a chlorine atom, a cyano group, a methyl group, a trifluoromethyl group and a methoxy group; $R^2$ denotes a methyl group; and $R^4$ denotes a group arbitrarily selected from among a fluorine atom, a methyl group and a methoxy group], the manufacturing method including stages in which a compound represented by formula (I) is obtained [these stages are the same as (stage [4]-1) and (stage [4]-2) in mode [4] above; the definitions of the substituent groups in the intermediates in (stage [4]-1) and (stage [4]-2) are the same as the definitions in mode [4-1], and $R^B$ in formula (IM-1) is a $C_{1-6}$ alkyl group].

[4-2] A more preferred aspect of mode [4] is a method in which a compound represented by formula (I) above is manufactured [in formula (I), p, $R^1$, $R^2$, $R^4$ and ring A group represented by formula (II) are defined in the same way as for mode [4-1] above; q denotes the integer 0; and $R^3$ denotes a fluorine atom], the manufacturing method including stages in which a compound represented by formula (I) is obtained [these stages are the same as (stage [4]-1) and (stage [4]-2) in mode [4] above; the definitions of the substituent groups in the intermediates in (stage [4]-1) and (stage [4]-2) are the same as the definitions in mode [4-2], and $R^B$ in formula (IM-1) is a $C_{1-6}$ alkyl group].

[4-3] A yet more preferred aspect of mode [4] is a method in which a compound represented by formula (I) above is manufactured [in formula (I), p, q, $R^1$, $R^2$, $R^3$ and $R^4$ are defined in the same way as for mode [4-2] above; ring A group represented by formula (II) is a pyrimidin-4-yl group; and a more specific group obtained by combining the definitions of p, $R^1$ and ring A group represented by formula (II) is a 2,5-dimethylpyrimidin-4-yl group], the manufacturing method including stages in which a compound represented by formula (I) is obtained [these stages are the same as (stage [4]-1) and (stage [4]-2) in mode [4] above; the definitions of the substituent groups in the intermediates in (stage [4]-1) and (stage [4]-2) are the same as the definitions in mode [4-3], and $R^B$ in formula (IM-1) is a $C_{1-6}$ alkyl group].

[4a] Another aspect of the fourth mode of the present invention is a method for manufacturing a compound represented by formula (I) below:

[C45]

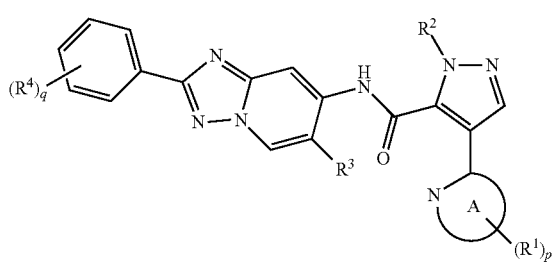
(I)

[in formula (I), p denotes an integer between 0 and 3; q denotes an integer between 0 and 2; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C46]

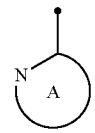
(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], the manufacturing method including stages in which a compound represented by formula (AD-2):

[C47]

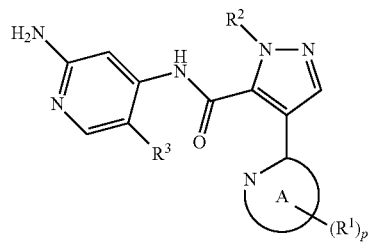
(AD-2)

[in formula (AD-2), p, $R^1$, $R^2$, $R^3$ and ring A group represented by formula (II) are defined in the same way as for formula (I) in mode [4a]] and a compound represented by formula (IM-1):

[C48]

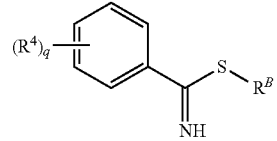
(IM-1)

[in formula (IM-1), q and $R^4$ are defined in the same way as for formula (I) in mode [4a]; and $R^B$ denotes a $C_{1-6}$ alkyl group] or a salt thereof (the compound represented by formula (IM-1) and salt thereof are commercially available compounds or compounds that can be easily obtained from commercially available compounds using manufacturing methods known from literature) are reacted with each other using a solvent which does not take part in the reaction, such as dimethyl sulfoxide or pyridine, at a temperature between 0° C. and a temperature at which the solvent refluxes, thereby obtaining a compound represented by formula (AD-3):

[C49]

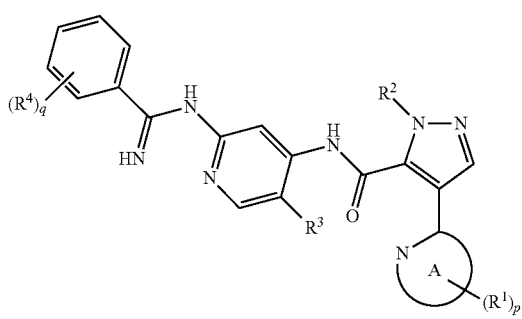

(AD-3)

[in formula (AD-3), p, q, $R^1$, $R^2$, $R^3$, $R^4$ and ring A group represented by formula (II) are defined in the same way as for formula (I) in mode [4a]] (stage [4a]-1), and the compound represented by formula (AD-3) is subjected to a cyclization reaction in the presence of air using a solvent which does not take part in the reaction, such as dimethyl sulfoxide (DMSO) or N-methylpyrrolidone (NMP), at a temperature between 0° C. and a temperature at which the solvent refluxes in the presence of a copper reagent such as copper iodide (CuI) or copper chloride (CuCl) (stage [4a]-2), thereby obtaining the compound represented by formula (I).

[4a-1] A preferred aspect of mode [4a] is a method in which a compound represented by formula (I) above is manufactured [in formula (I), p, q, $R^3$ and ring A group represented by formula (II) are defined in the same way as in mode [4a] above; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; $R^2$ denotes a methyl group; and $R^4$ denotes a group arbitrarily selected from among a fluorine atom, a methyl group and a methoxy group], the manufacturing method including stages in which a compound represented by formula (I) is obtained [these stages are the same as (stage [4a]-1) and (stage [4a]-2) in mode [4a] above; the definitions of the substituent groups in the intermediates in (stage [4a]-1) and (stage [4a]-2) are the same as the definitions in mode [4a-1], and $R^B$ in formula (IM-1) is a $C_{1-6}$ alkyl group].

[4a-2] A more preferred aspect of mode [4a] is a method in which a compound represented by formula (I) above is manufactured [in formula (I), p, $R^1$, $R^2$, $R^4$ and ring A group represented by formula (II) are defined in the same way as for mode [4a-1] above; q denotes the integer 0; and $R^3$ denotes a fluorine atom], the manufacturing method including stages in which a compound represented by formula (I) is obtained [these stages are the same as (stage [4a]-1) and (stage [4a]-2) in mode [4a] above; the definitions of the substituent groups in the intermediates in (stage [4a]-1) and (stage [4a]-2) are the same as the definitions in mode [4a-2], and $R^B$ in formula (IM-1) is a $C_{1-6}$ alkyl group].

[4a-3] A yet more preferred aspect of mode [4a] is a method in which a compound represented by formula (I) above is manufactured [in formula (I), p, q, $R^1$, $R^2$, $R^3$ and $R^4$ are defined in the same way as for mode [4a-2] above; ring A group represented by formula (II) is a thiazol-2-yl group or a pyrimidin-4-yl group; and a more specific group obtained by combining the definitions of p, $R^1$ and ring A group represented by formula (II) is a 4-(trifluoromethyl)thiazol-2-yl group, a 5-fluoro-2-methoxypyrimidin-4-yl group, a 2,5-dimethylpyrimidin-4-yl group or a 2-methylpyrimidin-4-yl group], the manufacturing method including stages in which a compound represented by formula (I) is obtained [these stages are the same as (stage [4a]-1) and (stage [4a]-2) in mode [4a] above; the definitions of the substituent groups in the intermediates in (stage [4a]-1) and (stage [4a]-2) are the same as the definitions in mode [4a-3], and $R^B$ in formula (IM-1) is a $C_{1-6}$ alkyl group].

A fifth mode of the present invention is a method for manufacturing a compound represented by formula (I) below:

[C50]

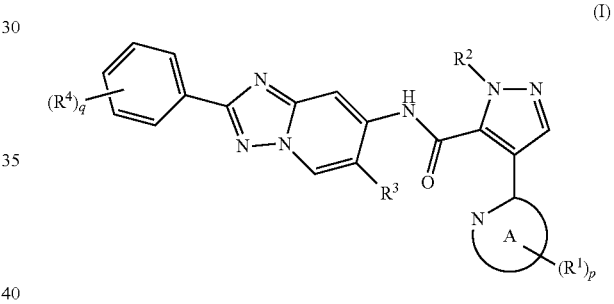

(I)

[in formula (I), p denotes an integer between 0 and 3; q denotes an integer between 0 and 2; $R^1$ groups each independently denote a group arbitrarily selected from among a halogen atom, a cyano group, a $C_{1-6}$ alkyl group, a halogenated $C_{1-6}$ alkyl group and a $C_{1-6}$ alkoxy group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C51]

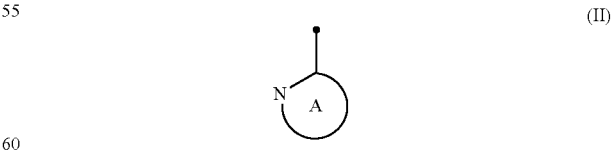

(II)

denotes a monocyclic 5- to 6-membered heteroaryl group arbitrarily selected from among a pyridin-2-yl group, a pyridazin-3-yl group, a pyrimidin-2-yl group, a pyrimidin-4-yl group and a pyrazin-2-yl group], the manufacturing method including a stage in which a compound represented by formula (AD-3):

[C52]

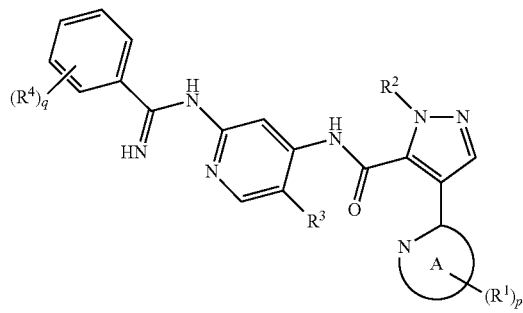

(AD-3)

[in formula (AD-3), p, q, $R^1$, $R^2$, $R^3$, $R^4$ and ring A group represented by formula (II) are defined in the same way as for formula (I) in mode [5]] is subjected to a cyclization reaction in the presence of air using a solvent which does not take part in the reaction, such as dimethyl sulfoxide (DMSO) or N-methylpyrrolidone (NMP), at a temperature between 0° C. and a temperature at which the solvent refluxes in the presence of a copper reagent such as copper iodide (CuI) or copper chloride (CuCl) (stage [5]-1), thereby obtaining the compound represented by formula (I).

[5-1] A preferred aspect of mode [5] is a method in which a compound represented by formula (I) above is manufactured [in formula (I), p, q, $R^3$ and ring A group represented by formula (II) are defined in the same way as for mode [5] above; $R^1$ denotes a group arbitrarily selected from among a fluorine atom, a chlorine atom, a cyano group, a methyl group, a trifluoromethyl group and a methoxy group; $R^2$ denotes a methyl group; and $R^4$ denotes a group arbitrarily selected from among a fluorine atom, a methyl group and a methoxy group], the manufacturing method including a stage in which a compound represented by formula (I) is obtained [this stage is the same as (stage [5]-1) in mode [5] above; and the definitions of the substituent groups in the intermediate in (stage [5]-1) are the same as the definitions in mode [5-1]].

[5-2] A more preferred aspect of mode [5] is a method in which a compound represented by formula (I) above is manufactured [in formula (I), p, $R^1$, $R^2$, $R^4$ and ring A group represented by formula (II) are defined in the same way as for mode [5-1] above; q denotes the integer 0; and $R^3$ denotes a fluorine atom], the manufacturing method including a stage in which a compound represented by formula (I) is obtained [this stage is the same as (stage [5]-1) in mode [5] above; and the definitions of the substituent groups in the intermediate in (stage [5]-1) are the same as the definitions in mode [5-2]].

[5-3] A yet more preferred aspect of mode [5] is a method in which a compound represented by formula (I) above is manufactured [in formula (I), p, q, $R^1$, $R^2$, $R^3$ and $R^4$ are defined in the same way as for mode [5-2] above; ring A group represented by formula (II) is a pyrimidin-4-yl group; and a more specific group obtained by combining the definitions of p, $R^1$ and ring A group represented by formula (II) is a 2,5-dimethylpyrimidin-4-yl group], the manufacturing method including a stage in which a compound represented by formula (I) is obtained [this stage is the same as (stage [5]-1) in mode [5] above; and the definitions of the substituent groups in the intermediate in (stage [5]-1) are the same as the definitions in mode [5-3]].

[5a] Another aspect of the fifth mode of the present invention is a method for manufacturing a compound represented by formula (I) below:

[C53]

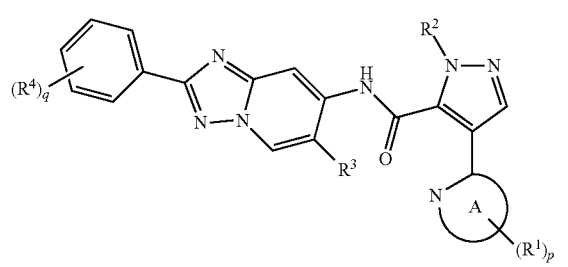

(I)

[in formula (I), p denotes an integer between 0 and 3; q denotes an integer between 0 and 2; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C54]

(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], the manufacturing method including a stage in which a compound represented by formula (AD-3):

[C55]

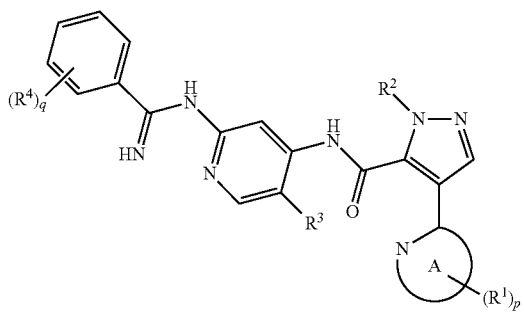

(AD-3)

[in formula (AD-3), p, q, R¹, R², R³, R⁴ and ring A group represented by formula (II) are defined in the same way as for formula (I) in mode [5a]] is subjected to a cyclization reaction in the presence of air using a solvent which does not take part in the reaction, such as dimethyl sulfoxide (DMSO) or N-methylpyrrolidone (NMP), at a temperature between 0° C. and a temperature at which the solvent refluxes in the presence of a copper reagent such as copper iodide (CuI) or copper chloride (CuCl) (stage [5a]-1), thereby obtaining the compound represented by formula (I).

[5a-1] A preferred aspect of mode [5a] is a method in which a compound represented by formula (I) above is manufactured [in formula (I), p, q, R³ and ring A group represented by formula (II) are defined in the same way as in mode [5a] above; R¹ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; R² denotes a methyl group; and R⁴ denotes a group arbitrarily selected from among a fluorine atom, a methyl group and a methoxy group], the manufacturing method including a stage in which a compound represented by formula (I) is obtained [this stage is the same as (stage [5a]-1) in mode [5a] above; and the definitions of the substituent groups in the intermediate in (stage [5a]-1) are the same as the definitions in mode [5a-1]].

[5a-2] A more preferred aspect of mode [5a] is a method in which a compound represented by formula (I) above is manufactured [in formula (I), p, R¹, R², R⁴ and ring A group represented by formula (II) are defined in the same way as for mode [5a-1] above; q denotes the integer 0; and R³ denotes a fluorine atom], the manufacturing method including a stage in which a compound represented by formula (I) is obtained [this stage is the same as (stage [5a]-1) in mode [5a] above; and the definitions of the substituent groups in the intermediate in (stage [5a]-1) are the same as the definitions in mode [5a-2]].

[5a-3] A yet more preferred aspect of mode [5a] is a method in which a compound represented by formula (I) above is manufactured [in formula (I), p, q, R¹, R², R³ and R⁴ are defined in the same way as for mode [5a-2] above; ring A group represented by formula (II) is a thiazol-2-yl group or a pyrimidin-4-yl group; and a more specific group obtained by combining the definitions of p, R¹ and ring A group represented by formula (II) is a 4-(trifluoromethyl) thiazol-2-yl group, a 5-fluoro-2-methoxypyrimidin-4-yl group, a 2,5-dimethylpyrimidin-4-yl group or a 2-methylpyrimidin-4-yl group], the manufacturing method including a stage in which a compound represented by formula (I) is obtained [this stage is the same as (stage [5a]-1) in mode [5a] above; and the definitions of the substituent groups in the intermediate in (stage [5a]-1) are the same as the definitions in mode [5a-3]].

[6] A sixth mode of the present invention is a method for manufacturing a compound represented by formula (I) below:

[C56]

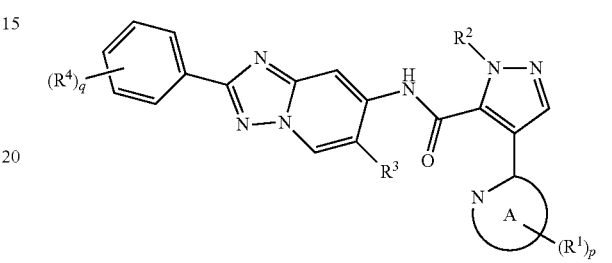

(I)

[in formula (I), p denotes an integer between 0 and 3; q denotes an integer between 0 and 2; R¹ groups each independently denote a group arbitrarily selected from among a halogen atom, a cyano group, a C₁₋₆ alkyl group, a halogenated C₁₋₆ alkyl group and a C₁₋₆ alkoxy group; R² denotes a C₁₋₆ alkyl group; R³ denotes a group arbitrarily selected from among a hydrogen atom and a fluorine atom; R⁴ groups each independently denote a group arbitrarily selected from among a halogen atom, a C₁₋₆ alkyl group and a C₁₋₆ alkoxy group; and ring A group represented by formula (II):

[C57]

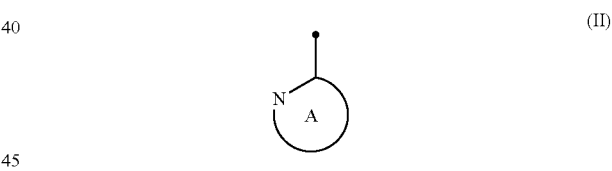

(II)

denotes a monocyclic 5- to 6-membered heteroaryl group arbitrarily selected from among a pyridin-2-yl group, a pyridazin-3-yl group, a pyrimidin-2-yl group, a pyrimidin-4-yl group and a pyrazin-2-yl group], the manufacturing method including stages in which a compound represented by formula (ET-1):

[C58]

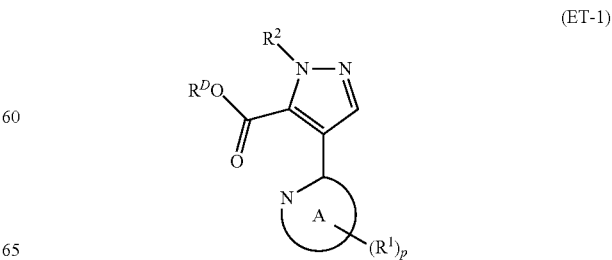

(ET-1)

[in formula (ET-1), p, $R^1$ and $R^2$ are defined in the same way as for formula (I) in mode [6]; $R^D$ denotes a group arbitrarily selected from among a $C_{1-6}$ alkyl group, a $C_{6-14}$ aryl group and a $C_{7-20}$ aralkyl group (a routine method for manufacturing a compound represented by formula (ET-1) is described later)] is subjected to hydrolysis [in cases where $R^D$ is a $C_{1-6}$ alkyl group (for example, a methyl group, an ethyl group, or the like), a $C_{6-14}$ aryl group (for example, a phenyl group or the like) or a $C_{7-20}$ aralkyl group (for example, a benzyl group), a reaction is carried out in the presence of a base such as lithium hydroxide, sodium hydroxide, potassium hydroxide, lithium carbonate, sodium carbonate or potassium carbonate using a solvent that is inert in the reaction, such as water, methanol, ethanol, 2-propanol, N,N-dimethylformamide, 1,4-dioxane, tetrahydrofuran or a mixture thereof at a temperature between 0° C. and a temperature at which the solvent refluxes; in cases where $R^D$ is a tert-butyl group (a $C_{1-6}$ alkyl group), a reaction with an acid such as hydrochloric acid or trifluoroacetic acid is carried out] or hydrogenation [in cases where $R^D$ is a $C_{7-20}$ aralkyl group (for example, a benzyl group or the like), a reaction is carried out in the presence of a catalyst such as palladium-carbon (Pd—C), Raney-nickel (Raney-Ni) or platinum oxide ($PtO_2$) in a hydrogen gas atmosphere using a solvent which does not take part in the reaction, such as an alcoholic solvent such as methanol, ethanol or 2-propanol, an ether-based solvent such as diethyl ether, tetrahydrofuran, 1,2-dimethoxyethane or 1,4-dioxane, or a polar solvent such as ethyl acetate or methyl acetate, or a mixture thereof, at a temperature between 0° C. and a temperature at which the solvent refluxes], thereby obtaining a compound represented by formula (CA-1):

[C59]

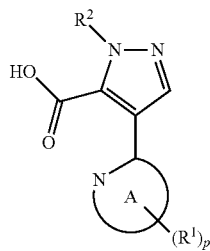

(CA-1)

[in formula (CA-1), p, $R^1$ and $R^2$ are defined in the same way as for formula (I) in mode [6]] (stage [6]-1), the compound represented by formula (CA-1) and a compound represented by formula (PY-2):

[C60]

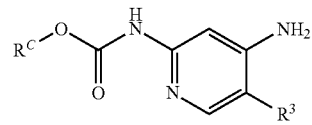

(PY-2)

[in formula (PY-2), $R^3$ denotes a group arbitrarily selected from among a hydrogen atom and a fluorine atom; $R^C$ denotes a group arbitrarily selected from among a $C_{1-6}$ alkyl group, a $C_{6-14}$ aryl group and a $C_{7-20}$ aralkyl group (a routine method for manufacturing a compound represented by formula (PY-2) is described later)] are reacted with each other in the presence of a condensing agent such as 1,3-dicyclohexylcarbodiimide (DCC), 1-ethyl-3-(3'-dimethylaminopropyl)carbodiimide hydrochloride (WSC.HCl), 1-hydroxybenzotriazole (Hobt), benzotriazol-1-yloxy-tris(dimethylamino)phosphonium hexafluorophosphate (a BOP reagent), bis(2-oxo-3-oxazolidinyl)phosphinic chloride (BOP-Cl), 2-chloro-1,3-dimethylimidazolinium hexafluorophosphate (CIP), 4-(4,6-dimethoxy-1,3,5-triazin-2-yl)-4-methylmorpholinium chloride (DMTMM), polyphosphoric acid (PPA) or 2-(1H-7-azabenzotriazol-1-yl)-1,1,3,3-tetramethyluronium hexafluorophosphate methanaminium (HATU), in the presence or absence of a base such as N,N-diisopropylethylamine, triethylamine, pyridine or lutidine, in a solvent which does not take part in the reaction, such as dichloromethane, chloroform, diethyl ether, tetrahydrofuran, toluene, benzene, N,N-dimethylformamide, N-methylpyrrolidone, methanol, ethanol or 2-propanol at a temperature between 0° C. and a temperature at which the solvent refluxes, thereby obtaining a compound represented by formula (AD-4):

[C61]

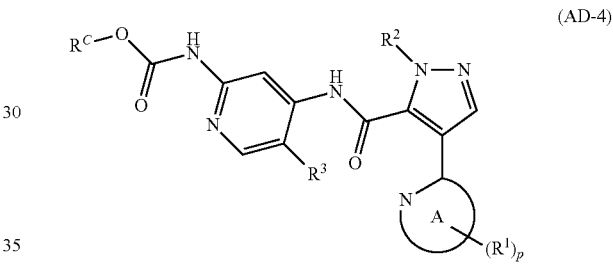

[in formula (AD-4), p, $R^1$, $R^2$ and $R^3$ are defined in the same way as for formula (I) in mode [6]; and $R^C$ denotes a group arbitrarily selected from among a $C_{1-6}$ alkyl group, a $C_{6-14}$ aryl group and a $C_{7-20}$ aralkyl group] (stage [6]-2), a —C(=O)$OR^C$ group ($R^C$ denotes a group arbitrarily selected from among a $C_{1-6}$ alkyl group, a $C_{6-14}$ aryl group and a $C_{7-20}$ aralkyl group), which is a protecting group for an amino group in formula (AD-4) is deprotected using a method known from literature, for example, a method disclosed in Greene et al., "Protective Groups in Organic Synthesis", fourth edition, 2007 (John Wiley & Sons), or using articles that have been publicly expressed, thereby obtaining a compound represented by formula (AD-2):

[C62]

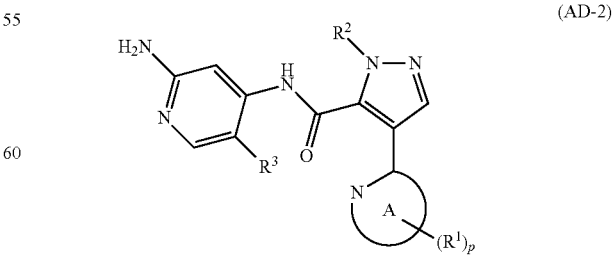

[in formula (AD-2), p, $R^1$, $R^2$ and $R^3$ are defined in the same way as for formula (I) in mode [6]] (stage [6]-3), the compound represented by formula (AD-2) and a compound represented by formula (IM-1):

[C63]

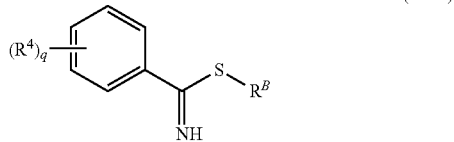

(IM-1)

[in formula (IM-1), q and $R^4$ are defined in the same way as for formula (I) in mode [6]; and $R^B$ denotes a $C_{1-6}$ alkyl group] or a salt thereof (the compound represented by formula (IM-1) and salt thereof are commercially available compounds or compounds that can be easily obtained from commercially available compounds using manufacturing methods known from literature) are reacted with each other using a solvent which does not take part in the reaction, such as dimethyl sulfoxide or pyridine, at a temperature between 0° C. and a temperature at which the solvent refluxes, thereby obtaining a compound represented by formula (AD-3):

[C64]

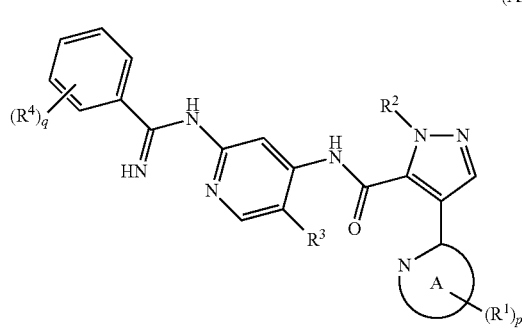

(AD-3)

[in formula (AD-3), p, q, $R^1$, $R^2$, $R^3$, $R^4$ and ring A group represented by formula (II) are defined in the same way as for formula (I) in mode [6]] (stage [6]-4), and the compound represented by formula (AD-3) is subjected to a cyclization reaction in the presence of air using a solvent which does not take part in the reaction, such as dimethyl sulfoxide (DMSO) or N-methylpyrrolidone (NMP), at a temperature between 0° C. and a temperature at which the solvent refluxes in the presence of a copper reagent such as copper iodide (CuI) or copper chloride (CuCl) (stage [6]-5), thereby obtaining the compound represented by formula (I).

[6-1] A preferred aspect of mode [6] is a method in which a compound represented by formula (I) above is manufactured [in formula (I), p, q, $R^3$ and ring A group represented by formula (II) are defined in the same way as for mode [6] above; $R^1$ denotes a group arbitrarily selected from among a fluorine atom, a chlorine atom, a cyano group, a methyl group, a trifluoromethyl group and a methoxy group; $R^2$ denotes a methyl group; and $R^4$ denotes a group arbitrarily selected from among a fluorine atom, a methyl group and a methoxy group], the manufacturing method including stages in which the compound represented by formula (I) is obtained [these stages are the same as (stage [6]-1) to (stage [6]-5) in mode [6] above; and the definitions of the substituent groups in the intermediates in (stage [6]-1) to (stage [6]-5) are the same as the definitions in mode [6-1]].

[6-2] A more preferred aspect of mode [6] is a method in which a compound represented by formula (I) above is manufactured [in formula (I), p, $R^1$, $R^2$, $R^4$ and ring A group represented by formula (II) are defined in the same way as for mode [6-1] above; q denotes the integer 0; and $R^3$ denotes a fluorine atom], the manufacturing method including stages in which a compound represented by formula (I) is obtained [these stages are the same as (stage [6]-1) to (stage [6]-5) in mode [6] above; and the definitions of the substituent groups in the intermediates in (stage [6]-1) to (stage [6]-5) are the same as the definitions in mode [6-2]].

[6-3] A yet more preferred aspect of mode [6] is a method in which a compound represented by formula (I) above is manufactured [in formula (I), p, q, $R^1$, $R^2$, $R^3$ and $R^4$ are defined in the same way as for mode [6-2] above; ring A group represented by formula (II) is a pyrimidin-4-yl group; and a more specific group obtained by combining the definitions of p, $R^1$ and ring A group represented by formula (II) is a 2,5-dimethylpyrimidin-4-yl group], the manufacturing method including stages in which a compound represented by formula (I) is obtained [these stages are the same as (stage [6]-1) to (stage [6]-5) in mode [6] above; and the definitions of the substituent groups in the intermediates in (stage [6]-1) to (stage [6]-5) are the same as the definitions in mode [6-3]].

[6a] Another aspect of the sixth mode of the present invention is a method for manufacturing a compound represented by formula (I) below:

[C65]

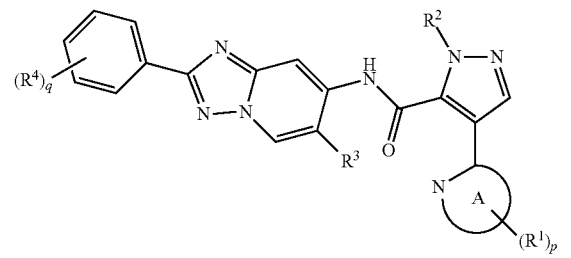

(I)

[in formula (I), p denotes an integer between 0 and 3; q denotes an integer between 0 and 2; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C66]

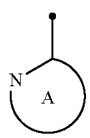
(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], the manufacturing method including stages in which a compound represented by formula (ET-1):

[C67]

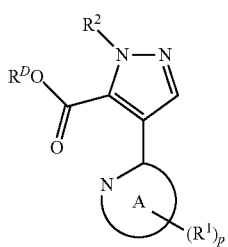
(ET-1)

[in formula (ET-1), p, $R^1$ and $R^2$ are defined in the same way as for formula (I) in mode [6a]; $R^D$ denotes a group arbitrarily selected from among a $C_{1-6}$ alkyl group, a $C_{6-14}$ aryl group and a $C_{7-20}$ aralkyl group (a routine method for manufacturing a compound represented by formula (ET-1) is described later)] is subjected to hydrolysis [in cases where $R^D$ is a $C_{1-6}$ alkyl group (for example, a methyl group, an ethyl group, or the like), a $C_{6-14}$ aryl group (for example, a phenyl group or the like) or a $C_{7-20}$ aralkyl group (for example, a benzyl group), a reaction is carried out in the presence of a base such as lithium hydroxide, sodium hydroxide, potassium hydroxide, lithium carbonate, sodium carbonate or potassium carbonate using a solvent that is inert in the reaction, such as water, methanol, ethanol, 2-propanol, N,N-dimethylformamide, 1,4-dioxane, tetrahydrofuran or a mixture thereof at a temperature between 0° C. and a temperature at which the solvent refluxes; in cases where $R^D$ is a tert-butyl group (a $C_{1-6}$ alkyl group), a reaction with an acid such as hydrochloric acid or trifluoroacetic acid is carried out] or hydrogenation [in cases where $R^D$ is a $C_{7-20}$ aralkyl group (for example, a benzyl group or the like), a reaction is carried out in the presence of a catalyst such as palladium-carbon (Pd—C), Raney-nickel (Raney-Ni) or platinum oxide ($PtO_2$) in a hydrogen gas atmosphere using a solvent which does not take part in the reaction, such as an alcoholic solvent such as methanol, ethanol or 2-propanol, an ether-based solvent such as diethyl ether, tetrahydrofuran, 1,2-dimethoxyethane or 1,4-dioxane, or a polar solvent such as ethyl acetate or methyl acetate, or a mixture thereof, at a temperature between 0° C. and a temperature at which the solvent refluxes], thereby obtaining a compound represented by formula (CA-1):

[C68]

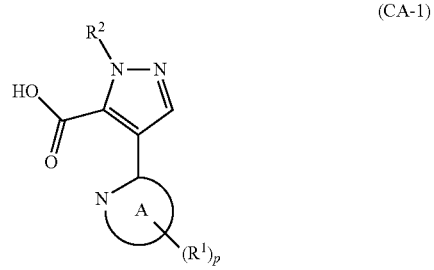
(CA-1)

[in formula (CA-1), p, $R^1$ and $R^2$ are defined in the same way as for formula (I) in mode [6a]] (stage [6a]-1), the compound represented by formula (CA-1) and a compound represented by formula (PY-2):

[C69]

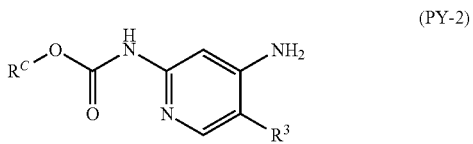
(PY-2)

[in formula (PY-2), $R^3$ denotes a group arbitrarily selected from among a hydrogen atom and a fluorine atom; $R^C$ denotes a group arbitrarily selected from among a $C_{1-6}$ alkyl group, a $C_{6-14}$ aryl group and a $C_{7-20}$ aralkyl group (a routine method for manufacturing a compound represented by formula (PY-2) is described later)] are reacted with each other in the presence of a condensing agent such as 1,3-dicyclohexylcarbodiimide (DCC), 1-ethyl-3-(3'-dimethylaminopropyl)carbodiimide hydrochloride (WSC.HCl), 1-hydroxybenzotriazole (Hobt), benzotriazol-1-yloxy-tris(dimethylamino)phosphonium hexafluorophosphate (a BOP reagent), bis(2-oxo-3-oxazolidinyl)phosphinic chloride (BOP-Cl), 2-chloro-1,3-dimethylimidazolinium hexafluorophosphate (CIP), 4-(4,6-dimethoxy-1,3,5-triazin-2-yl)-4-methylmorpholinium chloride (DMTMM), polyphosphoric acid (PPA) or 2-(1H-7-azabenzotriazol-1-yl)-1,1,3,3-tetramethyluronium hexafluorophosphate methanaminium (HATU), in the presence or absence of a base such as N,N-diisopropylethylamine, triethylamine, pyridine or lutidine, in a solvent which does not take part in the reaction, such as dichloromethane, chloroform, diethyl ether, tetrahydrofuran, toluene, benzene, N,N-dimethylformamide, N-methylpyrrolidone, methanol, ethanol or 2-propanol at a temperature between 0° C. and a temperature at which the solvent refluxes, thereby obtaining a compound represented by formula (AD-4):

[C70]

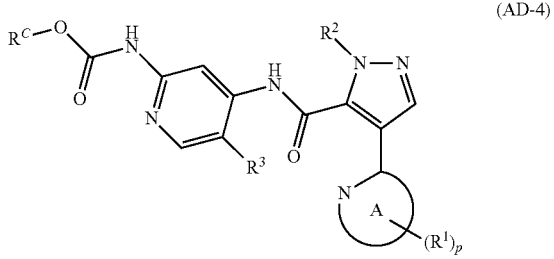

(AD-4)

[in formula (AD-4), p, $R^1$, $R^2$ and $R^3$ are defined in the same way as for formula (I) in mode [6a]; and $R^C$ denotes a group arbitrarily selected from among a $C_{1-6}$ alkyl group, a $C_{6-14}$ aryl group and a $C_{7-20}$ aralkyl group] (stage [6a]-2), a —C(=O)O$R^C$ group ($R^C$ denotes a group arbitrarily selected from among a $C_{1-6}$ alkyl group, a $C_{6-14}$ aryl group and a $C_{7-20}$ aralkyl group), which is a protecting group for an amino group in formula (AD-4) is deprotected using a method known from literature, for example, a method disclosed in Greene et al., "Protective Groups in Organic Synthesis", fourth edition, 2007 (John Wiley & Sons), or using articles that have been publicly expressed, thereby obtaining a compound represented by formula (AD-2):

[C71]

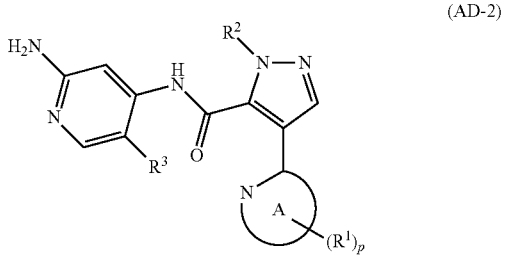

(AD-2)

[in formula (AD-2), p, $R^1$, $R^2$ and $R^3$ are defined in the same way as for formula (I) in mode [6a]] (stage [6a]-3), the compound represented by formula (AD-2) and a compound represented by formula (IM-1):

[C72]

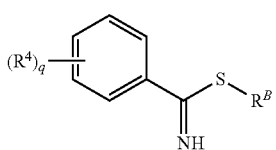

(IM-1)

[in formula (IM-1), q and $R^4$ are defined in the same way as for formula (I) in mode [6a]; and $R^B$ denotes a $C_{1-6}$ alkyl group] or a salt thereof (the compound represented by formula (IM-1) and salt thereof are commercially available compounds or compounds that can be easily obtained from commercially available compounds using manufacturing methods known from literature) are reacted with each other using a solvent which does not take part in the reaction, such as dimethyl sulfoxide or pyridine, at a temperature between 0° C. and a temperature at which the solvent refluxes, thereby obtaining a compound represented by formula (AD-3):

[C73]

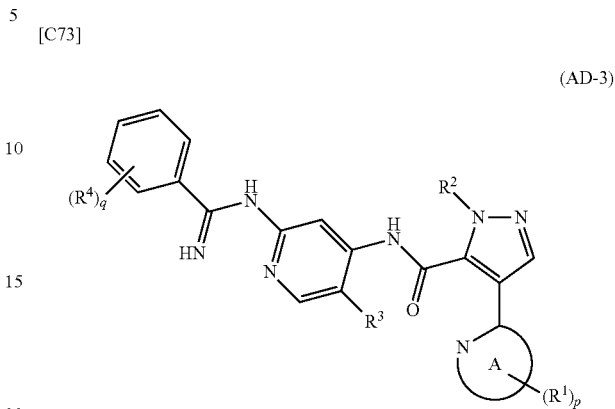

(AD-3)

[in formula (AD-3), p, q, $R^1$, $R^2$, $R^3$, $R^4$ and ring A group represented by formula (II) are defined in the same way as for formula (I) in mode [6a]] (stage [6a]-4), and the compound represented by formula (AD-3) is subjected to a cyclization reaction in the presence of air using a solvent which does not take part in the reaction, such as dimethyl sulfoxide (DMSO) or N-methylpyrrolidone (NMP), at a temperature between 0° C. and a temperature at which the solvent refluxes in the presence of a copper reagent such as copper iodide (CuI) or copper chloride (CuCl) (stage [6a]-5), thereby obtaining the compound represented by formula (I).

[6a-1] A preferred aspect of mode [6a] is a method in which a compound represented by formula (I) above is manufactured [in formula (I), p, q, $R^3$ and ring A group represented by formula (II) are defined in the same way as in mode [6a] above; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; $R^2$ denotes a methyl group; and $R^4$ denotes a group arbitrarily selected from among a fluorine atom, a methyl group and a methoxy group], the manufacturing method including stages in which a compound represented by formula (I) is obtained [these stages are the same as (stage [6a]-1) to (stage [6a]-5) in mode [6a] above; and the definitions of the substituent groups in the intermediates in (stage [6a]-1) to (stage [6a]-5) are the same as the definitions in mode [6a-1]].

[6a-2] A more preferred aspect of mode [6a] is a method in which a compound represented by formula (I) above is manufactured [in formula (I), p, $R^1$, $R^2$, $R^4$ and ring A group represented by formula (II) are defined in the same way as for mode [6a-1] above; q denotes the integer 0; and $R^3$ denotes a fluorine atom], the manufacturing method including stages in which a compound represented by formula (I) is obtained [these stages are the same as (stage [6a]-1) to (stage [6a]-5) in mode [6a] above; and the definitions of the substituent groups in the intermediates in (stage [6a]-1) to (stage [6a]-5) are the same as the definitions in mode [6a-2]].

[6a-3] A yet more preferred aspect of mode [6a] is a method in which a compound represented by formula (I) above is manufactured [in formula (I), p, q, $R^1$, $R^2$, $R^3$ and $R^4$ are defined in the same way as for mode [6a-2] above; ring A group represented by formula (II) is a thiazol-2-yl group or a pyrimidin-4-yl group; and a more specific group obtained by combining the definitions of p, $R^1$ and ring A group represented by formula (II) is a 4-(trifluoromethyl)thiazol-2-yl group, a 5-fluoro-2-methoxypyrimidin-4-yl group, a 2,5-dimethylpyrimidin-4-yl group or a 2-methyl-pyrimidin-4-yl group], the manufacturing method including stages in which a compound represented by formula (I) is obtained [these stages are the same as (stage [6a]-1) to (stage [6a]-5) in mode [6a] above; and the definitions of the substituent groups in the intermediates in (stage [6a]-1) to (stage [6a]-5) are the same as the definitions in mode [6a-3]].

[7] A seventh mode of the present invention is a method for manufacturing a compound represented by formula (AD-2) below:

[C74]

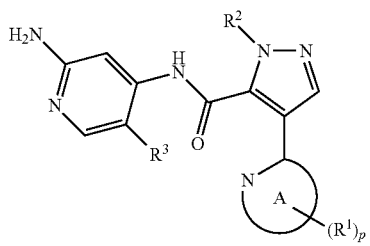

(AD-2)

[in formula (AD-2), p denotes an integer between 0 and 3; $R^1$ groups each independently denote a group arbitrarily selected from among a halogen atom, a cyano group, a $C_{1-6}$ alkyl group, a halogenated $C_{1-6}$ alkyl group and a $C_{1-6}$ alkoxy group; $R^2$ denotes a $C_{1-6}$ alkyl group; $R^3$ denotes a group arbitrarily selected from among a hydrogen atom and a fluorine atom; and ring A group represented by formula (II):

[C75]

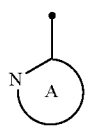

(II)

denotes a monocyclic 5- to 6-membered heteroaryl group arbitrarily selected from among a pyridin-2-yl group, a pyridazin-3-yl group, a pyrimidin-2-yl group, a pyrimidin-4-yl group and a pyrazin-2-yl group], the manufacturing method including stages in which a compound represented by formula (ET-1):

[C76]

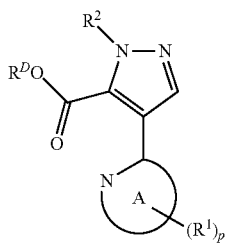

(ET-1)

[in formula (ET-1), p, $R^1$, $R^2$ and ring A group represented by formula (II) are defined in the same way as for formula (AD-2) in mode [7]; $R^D$ denotes a group arbitrarily selected from among a $C_{1-6}$ alkyl group, a $C_{6-14}$ aryl group and a $C_{7-20}$ aralkyl group (a routine method for manufacturing a compound represented by formula (ET-1) is described later)] is subjected to hydrolysis or hydrogenation (these are the same as the reactions described in mode [6] above) according to the type of $R^D$ group, thereby obtaining a compound represented by formula (CA-1):

[C77]

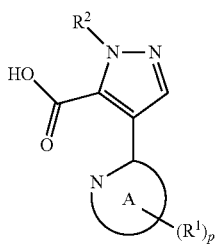

(CA-1)

[in formula (CA-1), p, $R^1$, $R^2$ and ring A group represented by formula (II) are defined in the same way as for formula (I) in mode [7]] (stage [7]-1), the compound represented by formula (CA-1) and a compound represented by formula (PY-2):

[C78]

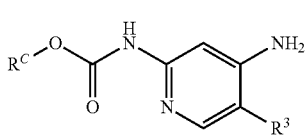

(PY-2)

[in formula (PY-2), $R^3$ denotes a group arbitrarily selected from among a hydrogen atom and a fluorine atom; $R^C$ denotes a group arbitrarily selected from among a $C_{1-6}$ alkyl group, a $C_{6-14}$ aryl group and a $C_{7-20}$ aralkyl group (a routine method for manufacturing a compound represented by formula (PY-2) is described later)] are reacted with each other in the presence of a condensing agent (condensing agents are the same as the condensing agents described in mode [6] above), in the presence or absence of a base such as N,N-diisopropylethylamine, triethylamine, pyridine or lutidine, in a solvent which does not take part in the reaction, such as dichloromethane, chloroform, diethyl ether, tetrahydrofuran, toluene, benzene, N,N-dimethylformamide, N-methylpyrrolidone, methanol, ethanol or 2-propanol at a temperature between 0° C. and a temperature at which the solvent refluxes, thereby obtaining a compound represented by formula (AD-4):

[C79]

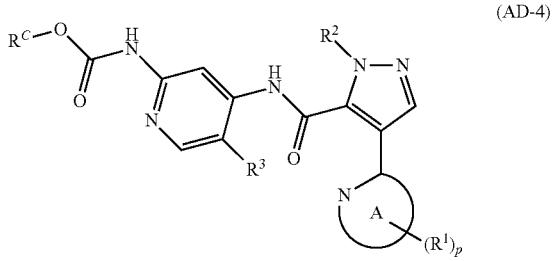

(AD-4)

[in formula (AD-4), p, $R^1$, $R^2$, $R^3$ and ring A group represented by formula (II) are defined in the same way as for formula (AD-2) in mode [7]; and $R^C$ denotes a group arbitrarily selected from among a $C_{1-6}$ alkyl group, a $C_{6-14}$ aryl group and a $C_{7-20}$ aralkyl group] (stage [7]-2), and a —C(=O)O$R^C$ group ($R^C$ denotes a group arbitrarily selected from among a $C_{1-6}$ alkyl group, a $C_{6-14}$ aryl group and a $C_{7-20}$ aralkyl group), which is a protecting group for an amino group in formula (AD-4) is deprotected (according to the deprotection method described in mode [6] above) (stage [7]-3), thereby obtaining the compound represented by formula (AD-2).

[7-1] A preferred aspect of mode [7] is a method in which a compound represented by formula (AD-2) above is manufactured [in formula (AD-2), p, $R^3$ and ring A group represented by formula (II) are defined in the same way as in mode [7] above; $R^1$ denotes a group arbitrarily selected from among a fluorine atom, a chlorine atom, a cyano group, a methyl group, a trifluoromethyl group and a methoxy group; and $R^2$ denotes a methyl group], the manufacturing method including stages in which a compound represented by formula (AD-2) is obtained [these stages are the same as (stage [7]-1) to (stage [7]-3) in mode [7] above; and the definitions of the substituent groups in the intermediates in (stage [7]-1) to (stage [7]-3) are the same as the definitions in mode [7-1]].

[7-2] A more preferred aspect of mode [7] is a method in which a compound represented by formula (AD-2) above is manufactured [in formula (AD-2), p, $R^1$, $R^2$ and ring A group represented by formula (II) are defined in the same way as in mode [7-1] above; and $R^3$ denotes a fluorine atom], the manufacturing method including stages in which a compound represented by formula (AD-2) is obtained [these stages are the same as (stage [7]-1) to (stage [7]-3) in mode [7] above; and the definitions of the substituent groups in the intermediates in (stage [7]-1) to (stage [7]-3) are the same as the definitions in mode [7-2]].

[7-3] A yet more preferred aspect of mode [7] is a method in which a compound represented by formula (AD-2) above is manufactured [in formula (AD-2), p, $R^1$, $R^2$ and $R^3$ are defined in the same way as for mode [7-2] above; ring A group represented by formula (II) is a pyrimidin-4-yl group; and a more specific group obtained by combining the definitions of p, $R^1$ and ring A group represented by formula (II) is a 2,5-dimethylpyrimidin-4-yl group], the manufacturing method including stages in which a compound represented by formula (AD-2) is obtained [these stages are the same as (stage [7]-1) to (stage [7]-3) in mode [7] above; and the definitions of the substituent groups in the intermediates in (stage [7]-1) to (stage [7]-3) are the same as the definitions in mode [7-3]].

[7a] Another aspect of the seventh mode of the present invention is a method for manufacturing a compound represented by formula (AD-2) below:

[C80]

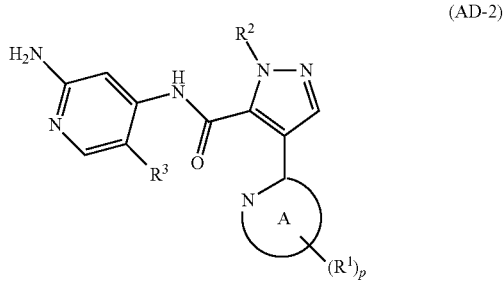

(AD-2)

[in formula (AD-2), p denotes an integer between 0 and 3; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; and ring A group represented by formula (II):

[C81]

(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], the manufacturing method including stages in which a compound represented by formula (ET-1):

[C82]

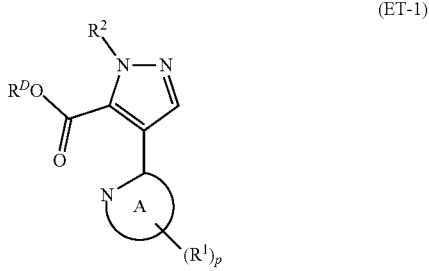

(ET-1)

[in formula (ET-1), p, $R^1$, $R^2$ and ring A group represented by formula (II) are defined in the same way as for formula (AD-2) in mode [7a]; $R^D$ denotes a group arbitrarily selected from among a $C_{1-6}$ alkyl group, a $C_{6-14}$ aryl group and a $C_{7-20}$ aralkyl group (a routine method for manufacturing a compound represented by formula (ET-1) is described later)] is subjected to hydrolysis or hydrogenation (these are the same as the reactions described in mode [6a] above) according to the type of $R^D$ group, thereby obtaining a compound represented by formula (CA-1):

[C83]

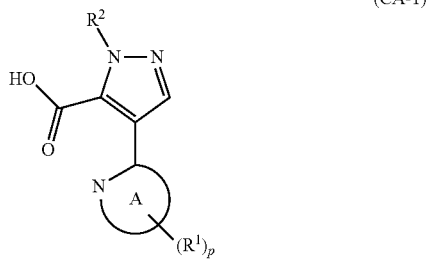

(CA-1)

[in formula (CA-1), p, $R^1$, $R^2$ and ring A group represented by formula (II) are defined in the same way as for formula (I) in mode [7a]] (stage [7a]-1), the compound represented by formula (CA-1) and a compound represented by formula (PY-2):

[C84]

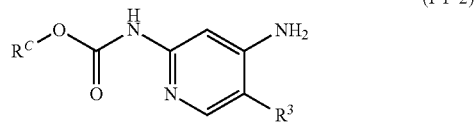

(PY-2)

[in formula (PY-2), $R^3$ denotes a group arbitrarily selected from among a hydrogen atom and a fluorine atom; $R^C$ denotes a group arbitrarily selected from among a $C_{1-6}$ alkyl group, a $C_{6-14}$ aryl group and a $C_{7-20}$ aralkyl group (a routine method for manufacturing a compound represented by formula (PY-2) is described later)] are reacted with each other in the presence of a condensing agent (such as a condensing agent described in mode [6a] above), in the presence or absence of a base such as N,N-diisopropylethylamine, triethylamine, pyridine or lutidine, in a solvent which does not take part in the reaction, such as dichloromethane, chloroform, diethyl ether, tetrahydrofuran, toluene, benzene, N,N-dimethylformamide, N-methylpyrrolidone, methanol, ethanol or 2-propanol at a temperature between 0° C. and a temperature at which the solvent refluxes, thereby obtaining a compound represented by formula (AD-4):

[C85]

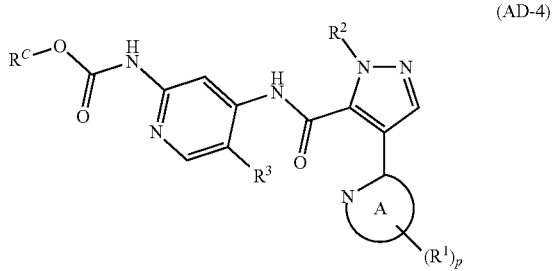

(AD-4)

[in formula (AD-4), p, $R^1$, $R^2$, $R^3$ and ring A group represented by formula (II) are defined in the same way as for formula (AD-2) in mode [7a]; and $R^C$ denotes a group arbitrarily selected from among a $C_{1-6}$ alkyl group, a $C_{6-14}$ aryl group and a $C_{7-20}$ aralkyl group] (stage [7a]-2), and a —C(=O)OR$^C$ group ($R^C$ denotes a group arbitrarily selected from among a $C_{1-6}$ alkyl group, a $C_{6-14}$ aryl group and a $C_{7-20}$ aralkyl group), which is a protecting group for an amino group in formula (AD-4) is deprotected (according to the deprotection method described in mode [6] above) (stage [7a]-3), thereby obtaining the compound represented by formula (AD-2).

[7a-1] A preferred aspect of mode [7a] is a method in which a compound represented by formula (AD-2) above is manufactured [in formula (AD-2), p, $R^3$ and ring A group represented by formula (II) are defined in the same way as in mode [7a] above; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; and $R^2$ denotes a methyl group], the manufacturing method including stages in which a compound represented by formula (AD-2) is obtained [these stages are the same as (stage [7a]-1) to (stage [7a]-3) in mode [7a] above; and the definitions of the substituent groups in the intermediates in (stage [7a]-1) to (stage [7a]-3) are the same as the definitions in mode [7a-1]].

[7a-2] A more preferred aspect of mode [7a] is a method in which a compound represented by formula (AD-2) above is manufactured [in formula (AD-2), p, $R^1$, $R^2$ and ring A group represented by formula (II) are defined in the same way as in mode [7a-1] above; and $R^3$ denotes a fluorine atom], the manufacturing method including stages in which a compound represented by formula (AD-2) is obtained [these stages are the same as (stage [7a]-1) to (stage [7a]-3) in mode [7a] above; and the definitions of the substituent groups in the intermediates in (stage [7a]-1) to (stage [7a]-3) are the same as the definitions in mode [7a-2]].

[7a-3] A yet more preferred aspect of mode [7a] is a method in which a compound represented by formula (AD-2) above is manufactured [in formula (AD-2), p, $R^1$, $R^2$ and $R^3$ are defined in the same way as for mode [7a-2] above; ring A group represented by formula (II) is a thiazol-2-yl group or a pyrimidin-4-yl group; and a more specific group obtained by combining the definitions of p, $R^1$ and ring A group represented by formula (II) is a 4-(trifluoromethyl) thiazol-2-yl group, a 5-fluoro-2-methoxypyrimidin-4-yl group, a 2,5-dimethylpyrimidin-4-yl group or a 2-methylpyrimidin-4-yl group], the manufacturing method including stages in which a compound represented by formula (AD-2) is obtained [these stages are the same as (stage [7a]-1) to (stage [7a]-3) in mode [7a] above; and the definitions of the substituent groups in the intermediates in (stage [7a]-1) to (stage [7a]-3) are the same as the definitions in mode [7a-3]].

[8] An eighth mode of the present invention is a compound represented by formula (AD-1):

[C86]

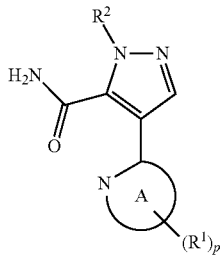

(AD-1)

[in formula (AD-1), p denotes an integer between 0 and 3; $R^1$ groups each independently denote a group arbitrarily selected from among a halogen atom, a cyano group, a $C_{1-6}$ alkyl group, a halogenated $C_{1-6}$ alkyl group and a $C_{1-6}$ alkoxy group; $R^2$ denotes a $C_{1-6}$ alkyl group; and ring A group represented by formula (II):

[C87]

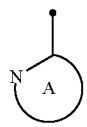

(II)

denotes a monocyclic 5- to 6-membered heteroaryl group arbitrarily selected from among a pyridin-2-yl group, a pyridazin-3-yl group, a pyrimidin-2-yl group, a pyrimidin-4-yl group and a pyrazin-2-yl group], or a salt of the compound, or a solvate of the compound or salt.

[8-1] A preferred aspect of mode [8] is a compound represented by formula (AD-1) above [in formula (AD-1), p and ring A group represented by formula (II) are defined in the same way as for mode [8] above; $R^1$ denotes a group arbitrarily selected from among a fluorine atom, a chlorine atom, a cyano group, a methyl group, a trifluoromethyl group and a methoxy group; and $R^2$ denotes a methyl group], or a salt of the compound, or a solvate of the compound or salt.

[8-2] A more preferred aspect of mode [8] is a compound represented by formula (AD-1) above [in formula (AD-1), p, $R^1$ and $R^2$ are defined in the same way as for mode [8-1] above; ring A group represented by formula (II) is a pyrimidin-4-yl group; and a more specific group obtained by combining the definitions of p, $R^1$ and ring A group represented by formula (II) is a 2,5-dimethylpyrimidin-4-yl group], or a salt of the compound, or a solvate of the compound or salt.

[8a] Another aspect of the eighth mode of the present invention is a compound represented by formula (AD-1):

[C88]

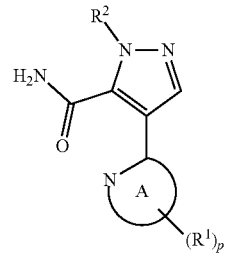

(AD-1)

[in formula (AD-1), p denotes an integer between 0 and 3; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; and ring A group represented by formula (II):

[C89]

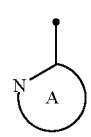

(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], or a salt of the compound, or a solvate of the compound or salt.

[8a-1] A preferred aspect of mode [8a] is a compound represented by formula (AD-1) above [in formula (AD-1), p and ring A group represented by formula (II) are defined in the same way as for mode [8a] above; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; and $R^2$ denotes a methyl group], or a salt of the compound, or a solvate of the compound or salt.

[8a-2] A more preferred aspect of mode [8a] is a compound represented by formula (AD-1) above [in formula (AD-1), p denotes an integer between 1 and 3; $R^1$, $R^2$ and ring A group represented by formula (II) are defined in the same way as in mode [8a-1] above], or a salt of the compound, or a solvate of the compound or salt.

[8a-3] A yet more preferred aspect of mode [8a] is a compound represented by formula (AD-1) above [in formula (AD-1), p, $R^1$ and $R^2$ are defined in the same way as for mode [8a-2] above; ring A group represented by formula (II) is a thiazol-2-yl group or a pyrimidin-4-yl group; and a more specific group obtained by combining the definitions of p, $R^1$ and ring A group represented by formula (II) is a 4-(trifluoromethyl)thiazol-2-yl group, a 5-fluoro-2-methoxypyrimidin-4-yl group, a 2,5-dimethylpyrimidin-4-yl group or a 2-methylpyrimidin-4-yl group], or a salt of the compound, or a solvate of the compound or salt.

[8']

Mode no. 8' of the present invention lists the intermediate compounds shown below as preferred intermediate compounds for compounds represented by formula (AD-1) in modes [8] to [8-3] above or modes [8a] to [8a-3] above, or salts of these intermediate compounds, or solvates of the intermediate compounds or salts. The listed intermediate compounds are obtained in steps having working example numbers corresponding to the compound names. For example, Working Example Number 1-2 means that an intermediate compound corresponding to <Step 2> in Working Example 1 is obtained. Moreover, the names of the compounds shown below are based on English names obtained using the Cambridge Soft Chem BioDraw Ultra 12.0.2.1076 compound nomenclature program.

TABLE 1

| Compound | Working Example No. |
| --- | --- |
| 4-(2,5-dimethylpyrimidin-4-yl)-1-methyl-1H-pyrazole-5-carboxamde | 2 and 6-1 |
| 1-methyl-4-(2-methylpyrimidin-4-yl)-1H-pyrazole-5-carboxamide | 9 |
| 4-(5-fluoro-2-methoxypyrimidin-4-yl)-1-methyl-1H-pyrazole-5-carboxamide | 13 |
| 1-methyl-4-(4-(trifluoromethyl)thiazol-2-yl)-1H-pyrazole-5-carboxamide | 17 |

[9] A ninth mode of the present invention is a compound represented by formula (AD-2):

[C90]

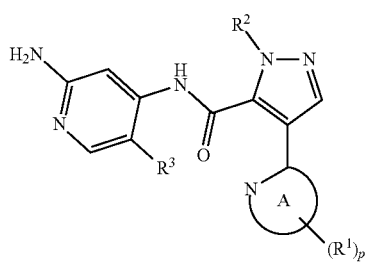

(AD-2)

[in formula (AD-2), p denotes an integer between 0 and 3; $R^1$ groups each independently denote a group arbitrarily selected from among a halogen atom, a cyano group, a $C_{1-6}$ alkyl group, a halogenated $C_{1-6}$ alkyl group and a $C_{1-6}$ alkoxy group; $R^2$ denotes a $C_{1-6}$ alkyl group; $R^3$ denotes a group arbitrarily selected from among a hydrogen atom and a fluorine atom; and ring A group represented by formula (II):

[C91]

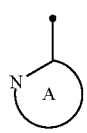

(II)

denotes a monocyclic 5- to 6-membered heteroaryl group arbitrarily selected from among a pyridin-2-yl group, a pyridazin-3-yl group, a pyrimidin-2-yl group, a pyrimidin-4-yl group and a pyrazin-2-yl group], or a salt of the compound, or a solvate of the compound or salt.

[9-1] A preferred aspect of mode [9] is a compound represented by formula (AD-2) above [in formula (AD-2), p, $R^3$ and ring A group represented by formula (II) are defined in the same way as for mode [9] above; $R^1$ denotes a group arbitrarily selected from among a fluorine atom, a chlorine atom, a cyano group, a methyl group, a trifluoromethyl group and a methoxy group; and $R^2$ denotes a methyl group], or a salt of the compound, or a solvate of the compound or salt.

[9-2] A more preferred aspect of mode [9] is a compound represented by formula (AD-2) above [in formula (AD-2), p, $R^1$, $R^2$ and ring A group represented by formula (II) are defined in the same way as for mode [9-1] above; and $R^3$ denotes a fluorine atom], or a salt of the compound, or a solvate of the compound or salt.

[9-3] A yet more preferred aspect of mode [9] is a compound represented by formula (AD-2) above [in formula (AD-2), p, $R^1$, $R^2$ and $R^3$ are defined in the same way as for mode [9-2] above; ring A group represented by formula (II) is a pyrimidin-4-yl group; and a more specific group obtained by combining the definitions of p, $R^1$ and ring A group represented by formula (II) is a 2,5-dimethylpyrimidin-4-yl group], or a salt of the compound, or a solvate of the compound or salt.

[9a] Another aspect of the ninth mode of the present invention is a compound represented by formula (AD-2):

[C92]

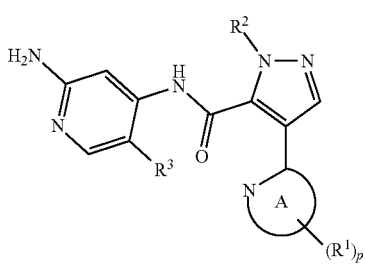

(AD-2)

[in formula (AD-2), p denotes an integer between 0 and 3; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; and ring A group represented by formula (II):

[C93]

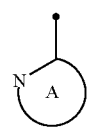

(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], or a salt of the compound, or a solvate of the compound or salt.

[9a-1] A preferred aspect of mode [9a] is a compound represented by formula (AD-2) above [in formula (AD-2), p, $R^3$ and ring A group represented by formula (II) are defined in the same way as for mode [9a] above; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; and $R^2$ denotes a methyl group], or a salt of the compound, or a solvate of the compound or salt.

[9a-2] A more preferred aspect of mode [9a] is a compound represented by formula (AD-2) above [in formula (AD-2), p, $R^1$, $R^2$ and ring A group represented by formula (II) are defined in the same way as for mode [9a-1] above; and $R^3$ denotes a fluorine atom], or a salt of the compound, or a solvate of the compound or salt.

[9a-3] A yet more preferred aspect of mode [9a] is a compound represented by formula (AD-2) above [in formula (AD-2), p, $R^2$ and $R^3$ are defined in the same way as for mode [9a-2] above; ring A group represented by formula (II) is a thiazol-2-yl group or a pyrimidin-4-yl group; and a more specific group obtained by combining the definitions of p, $R^1$ and ring A group represented by formula (II) is a 4-(trifluoromethyl)thiazol-2-yl group, a 5-fluoro-2-methoxypyrimidin-4-yl group, a 2,5-dimethylpyrimidin-4-yl group or a 2-methylpyrimidin-4-yl group], or a salt of the compound, or a solvate of the compound or salt.

[9']

Mode no. 9' of the present invention lists the intermediate compounds shown below as preferred intermediate compounds for compounds represented by formula (AD-2) in modes [9] to [9-3] above or modes [9a] to [9a-3] above, or salts of these intermediate compounds, or solvates of the intermediate compounds or salts. The listed intermediate compounds are obtained in steps having working example numbers corresponding to the compound names. Explanations relating to the names of the compounds and the working example numbers are the same as the explanations given in mode [8'] above.

TABLE 2

| Compound | Working Example No. |
| --- | --- |
| N-(2-amino-5-fluoropyridin-4-yl)-4-(2,5-dimethylpyrimidin-4-yl)-1-methyl-1H-pyrazole-5-carboxamide | 5-3 and 6-2 |
| N-(2-amino-5-fluoropyridin-4-yl)-4-(2-methylpyrimidin-4-yl)-1-methyl-1H-pyrazole-5-carboxamide | 10-1 |
| N-(2-amino-5-fluoropyridin-4-yl)-4-(5-fluoro-2-methoxypyrimidin-4-yl)-1-methyl-1H-pyrazole-5-carboxamide | 14-1 |
| N-(2-amino-5-fluoropyridin-4-yl)-4-(4-(trifluoromethyl)thiazol-2-yl)-1-methyl-1H-pyrazole-5-carboxamide | 18-1 |

A tenth mode of the present invention is a compound represented by formula (AD-3):

[C94]

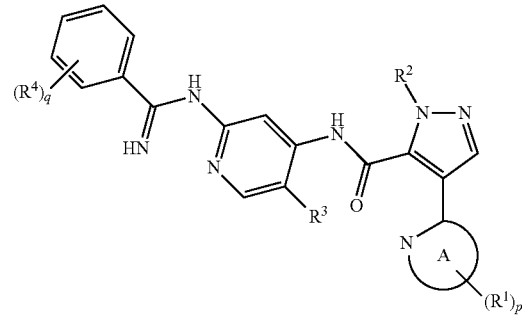

(AD-3)

[in formula (AD-3), p denotes an integer between 0 and 3; q denotes an integer between 0 and 2; $R^1$ groups each independently denote a group arbitrarily selected from among a halogen atom, a cyano group, a $C_{1-6}$ alkyl group, a halogenated $C_{1-6}$ alkyl group and a $C_{1-6}$ alkoxy group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C95]

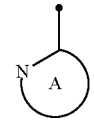

(II)

denotes a monocyclic 5- to 6-membered heteroaryl group arbitrarily selected from among a pyridin-2-yl group, a pyridazin-3-yl group, a pyrimidin-2-yl group, a pyrimidin-4-yl group and a pyrazin-2-yl group], or a salt of the compound, or a solvate of the compound or salt.

[10-1] A preferred aspect of mode [10] is a compound represented by formula (AD-3) above [in formula (AD-3), p, q, $R^3$ and ring A group represented by formula (II) are defined in the same way as for mode [10] above; $R^1$ denotes a group arbitrarily selected from among a fluorine atom, a chlorine atom, a cyano group, a methyl group, a trifluoromethyl group and a methoxy group; $R^2$ denotes a methyl group; and $R^4$ denotes a group arbitrarily selected from among a fluorine atom, a methyl group and a methoxy group], or a salt of the compound, or a solvate of the compound or salt.

[10-2] A more preferred aspect of mode [10] is a compound represented by formula (AD-3) above [in formula (AD-3), p, $R^1$, $R^2$, $R^4$ and ring A group represented by formula (II) are defined in the same way as for mode [10-1] above; q denotes the integer 0; and $R^3$ denotes a fluorine atom], or a salt of the compound, or a solvate of the compound or salt.

[10-3] A yet more preferred aspect of mode [10] is a compound represented by formula (AD-3) above [in formula (AD-3), p, q, $R^1$, $R^2$, $R^3$ and $R^4$ are defined in the same way as for mode [10-2] above; ring A group represented by formula (II) is a pyrimidin-4-yl group; and a more specific group obtained by combining the definitions of p, $R^1$ and ring A group represented by formula (II) is a 2,5-dimethylpyrimidin-4-yl group], or a salt of the compound, or a solvate of the compound or salt.

[10a] Another aspect of the tenth mode of the present invention is a compound represented by formula (AD-3):

[C96]

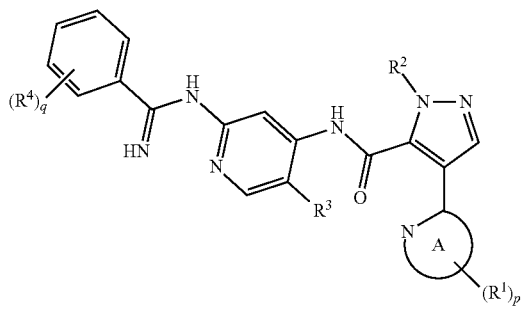

(AD-3)

[in formula (AD-3), p denotes an integer between 0 and 3; q denotes an integer between 0 and 2; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C97]

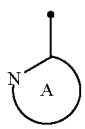

(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], or a salt of the compound, or a solvate of the compound or salt.

[10a-1] A preferred aspect of mode [10a] is a compound represented by formula (AD-3) above [in formula (AD-3), p, q, $R^3$ and ring A group represented by formula (II) are defined in the same way as for mode [10a] above; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; $R^2$ denotes a methyl group; and $R^4$ denotes a group arbitrarily selected from among a fluorine atom, a methyl group and a methoxy group], or a salt of the compound, or a solvate of the compound or salt.

[10a-2] A more preferred aspect of mode [10a] is a compound represented by formula (AD-3) above [in formula (AD-3), p, $R^1$, $R^2$, $R^4$ and ring A group represented by formula (II) are defined in the same way as for mode [10a-1] above; q denotes the integer 0; and $R^3$ denotes a fluorine atom], or a salt of the compound, or a solvate of the compound or salt.

[10a-3] A yet more preferred aspect of mode [10a] is a compound represented by formula (AD-3) above [in formula (AD-3), p, q, $R^1$, $R^2$, $R^3$ and $R^4$ are defined in the same way as for mode [10a-2] above; ring A group represented by formula (II) is a thiazol-2-yl group or a pyrimidin-4-yl group; and a more specific group obtained by combining the definitions of p, $R^1$ and ring A group represented by formula (II) is a 4-(trifluoromethyl)thiazol-2-yl group, a 5-fluoro-2-methoxypyrimidin-4-yl group, a 2,5-dimethylpyrimidin-4-yl group or a 2-methylpyrimidin-4-yl group], or a salt of the compound, or a solvate of the compound or salt.

[10']

Mode no. 10' of the present invention lists the intermediate compounds shown below as preferred intermediate compounds for compounds represented by formula (AD-3) in modes [10] to [10-3] above or modes [10a] to [10a-3] above, or salts of these intermediate compounds, or solvates of the intermediate compounds or salts. The listed intermediate compounds are obtained in steps having working example numbers corresponding to the compound names. Explanations relating to the names of the compounds and the working example numbers are the same as the explanations given in mode [8'] above.

TABLE 3

| Compound | Working Example No. |
|---|---|
| N-(benzimidamido-5-fluoropyridin-4-yl)-4-(2,5-dimethylpyrimidin-4-yl)-1-methyl-1H-pyrazole-5-carboxamide | 6-3 |
| N-(benzimidamido-5-fluoropyridin-4-yl)-4-(2-methylpyrimidin-4-yl)-1-methyl-1H-pyrazole-5-carboxamide | 10-2 |
| N-(benzimidamido-5-fluoropyridin-4-yl)-4-(5-fluoro-2-methoxypyrimidin-4-yl)-1-methyl-1H-pyrazole-5-carboxamide | 14-2 |
| N-(benzimidamido-5-fluoropyridin-4-yl)-4-(4-(trifluoromethyl)thiazol-2-yl)-1-methyl-1H-pyrazole-5-carboxamide | 18-2 |

[11] An eleventh mode of the present invention is a compound represented by formula (PY-1-1):

[C98]

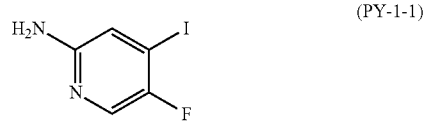

(PY-1-1)

or a salt of the compound, or a solvate of the compound or salt.

[12] A twelfth mode of the present invention is a compound represented by formula (PY-2-1):

[C99]

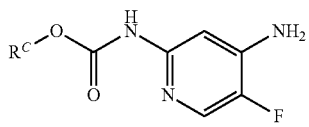

(PY-2-1)

[in formula (PY-2), $R^C$ denotes a group arbitrarily selected from among a $C_{1-6}$ alkyl group, a $C_{6-14}$ aryl group and a $C_{7-20}$ aralkyl group], or a salt of the compound, or a solvate of the compound or salt.

[12-1] A preferred aspect of mode [12] is a compound represented by formula (PY-2-1) above [in formula (PY-2), $R^C$ denotes a benzyl group], or a salt of the compound, or a solvate of the compound or salt.

A thirteenth mode of the present invention is a compound represented by formula (ET-1):

[C100]

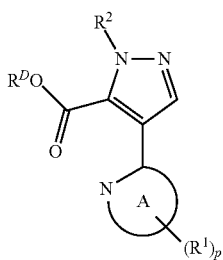

(ET-1)

[in formula (ET-1), p denotes an integer between 0 and 3; $R^1$ groups each independently denote a group arbitrarily selected from among a halogen atom, a cyano group, a $C_{1-6}$ alkyl group, a halogenated $C_{1-6}$ alkyl group and a $C_{1-6}$ alkoxy group; $R^2$ denotes a $C_{1-6}$ alkyl group; $R^D$ groups each independently denote a group arbitrarily selected from among a $C_{1-6}$ alkyl group, a $C_{6-14}$ aryl group and a $C_{7-20}$ aralkyl group; and ring A group represented by formula (II):

[C101]

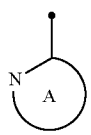

(II)

denotes a monocyclic 5- to 6-membered heteroaryl group arbitrarily selected from among a pyridin-2-yl group, a pyridazin-3-yl group, a pyrimidin-2-yl group, a pyrimidin-4-yl group and a pyrazin-2-yl group], or a salt of the compound, or a solvate of the compound or salt.

[13-1] A preferred aspect of mode [13] is a compound represented by formula (ET-1) above [in formula (ET-1), p denotes an integer between 0 and 3; $R^1$ groups each independently denote a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; $R^2$ denotes a methyl group; $R^D$ groups each independently denote a group arbitrarily selected from among a methyl group, an ethyl group, a tert-butyl group, a phenyl group and a benzyl group; and ring A group represented by formula (II) is defined in the same way as in mode [13] above], or a salt of the compound, or a solvate of the compound or salt.

[13-2] A more preferred aspect of mode [13] is a compound represented by formula (ET-1) above [in formula (ET-1), p denotes an integer between 1 and 3; R', $R^2$, $R^D$ and ring A group represented by formula (II) are defined in the same way as in mode [13-1] above], or a salt of the compound, or a solvate of the compound or salt.

[13-3] A preferred aspect of mode [13] is a compound represented by formula (ET-1) above [in formula (ET-1), p, $R^1$, $R^2$, $R^D$ and ring A group represented by formula (II) are defined in the same way as in mode [13-2] above; and a more specific group obtained by combining the definitions of p, $R^1$ and ring A group is a 2,5-dimethylpyrimidin-4-yl group], or a salt of the compound, or a solvate of the compound or salt.

[13a] Another aspect of the thirteenth mode of the present invention is a compound represented by formula (ET-1) below:

[C102]

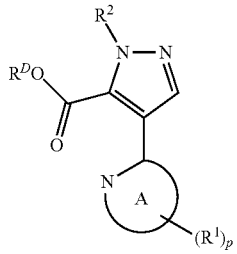

(ET-1)

[in formula (ET-1), p denotes an integer between 0 and 3; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^D$ denotes a group arbitrarily selected from among a $C_{1-6}$ alkyl group, a $C_{6-14}$ aryl group and a $C_{7-20}$ aralkyl group; and ring A group represented by formula (II):

[C103]

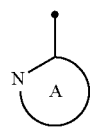

(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], or a salt of the compound, or a solvate of the compound or salt.

[13a-1] A preferred aspect of mode [13a] is a compound represented by formula (ET-1) above [in formula (ET-1), p denotes an integer between 0 and 3; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; $R^2$ denotes a methyl group; $R^D$ groups each independently denote a group arbitrarily selected from among a methyl group, an ethyl group, a tert-butyl group, a phenyl group and a benzyl group; and ring A group represented by formula (II) is defined in the same way as in mode [13a] above], or a salt of the compound, or a solvate of the compound or salt.

[13a-2] A more preferred aspect of mode [13a] is a compound represented by formula (ET-1) above [in formula (ET-1), p denotes an integer between 1 and 3; $R^1$, $R^2$, $R^D$ and ring A group represented by formula (II) are defined in the same way as in mode [13a-1] above], or a salt of the compound, or a solvate of the compound or salt.

[13a-3] A yet more preferred aspect of mode [13a] is a compound represented by formula (ET-1) above [in formula (ET-1), p, $R^1$, $R^2$ and $R^D$ are defined in the same way as in mode [13a-2] above; ring A group represented by formula (II) is a thiazol-2-yl group or a pyrimidin-4-yl group; and a more specific group obtained by combining the definitions of p, $R^1$ and ring A group represented by formula (II) is a 4-(trifluoromethyl)thiazol-2-yl group, a 5-fluoro-2-methoxypyrimidin-4-yl group, a 2,5-dimethylpyrimidin-4-yl group or a 2-methylpyrimidin-4-yl group], or a salt of the compound, or a solvate of the compound or salt.

[13']

Mode no. 13' of the present invention lists the intermediate compounds shown below as preferred intermediate compounds for compounds represented by formula (ET-1) in modes [13] to [13-3] above or modes [13a] to [13a-3] above, or salts of these intermediate compounds, or solvates of the intermediate compounds or salts. The listed intermediate compounds are obtained in steps having working example numbers corresponding to the compound names. Explanations relating to the names of the compounds and the working example numbers are the same as the explanations given in mode [8'] above.

TABLE 4

| Compound | Working Example No. |
|---|---|
| Ethyl 4-(2,5-dimethylpyrimidin-4-yl)-1-methyl-1H-pyrazole-5-carboxylate | 1 |
| Methyl 1-methyl-4-(2-methylpyrimidin-4-yl)-1H-pyrazole-5-carboxylate | 7 |
| Methyl 4-(5-fluoro-2-methoxypyrimidin-4-yl)-1-methyl-1H-pyrazole-5-carboxylate | 11 |
| Methyl 1-methyl-4-(4-(trifluoromethyl)thiazol-2-yl)-1H-pyrazole-5-carboxylate | 15-2 |

[14] A fourteenth mode of the present invention is a compound represented by formula (CA-1):

[C104]

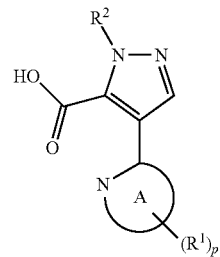

(CA-1)

[in formula (CA-1), p denotes an integer between 0 and 3; $R^1$ groups each independently denote a group arbitrarily selected from among a halogen atom, a cyano group, a $C_{1-6}$ alkyl group, a halogenated $C_{1-6}$ alkyl group and a $C_{1-6}$ alkoxy group; $R^2$ denotes a $C_{1-6}$ alkyl group; and ring A group represented by formula (II):

[C105]

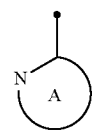

(II)

denotes a monocyclic 5- to 6-membered heteroaryl group arbitrarily selected from among a pyridin-2-yl group, a pyridazin-3-yl group, a pyrimidin-2-yl group, a pyrimidin-4-yl group and a pyrazin-2-yl group], or a salt of the compound, or a solvate of the compound or salt.

[14-1] A preferred aspect of mode [14] is a compound represented by formula (CA-1) above [in formula (CA-1), p denotes an integer between 0 and 3; $R^1$ groups each independently denote a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; $R^2$ denotes a methyl group; and ring A group represented by formula (II) is defined in the same way as in mode [14] above], or a salt of the compound, or a solvate of the compound or salt.

[14-2] A more preferred aspect of mode [14] is a compound represented by formula (CA-1) above [in formula (CA-1), p denotes an integer between 1 and 3; $R^1$, $R^2$ and ring A group represented by formula (II) are defined in the same way as in mode [14-1] above], or a salt of the compound, or a solvate of the compound or salt.

[14-3] A preferred aspect of mode [14] is a compound represented by formula (CA-1) above [in formula (CA-1), p, $R^1$, $R^2$ and ring A group represented by formula (II) are defined in the same way as in mode [14-2] above; and a more specific group obtained by combining the definitions of p, $R^1$ and ring A group is a 2,5-dimethylpyrimidin-4-yl group], or a salt of the compound, or a solvate of the compound or salt.

[14a] Another aspect of the fourteenth mode of the present invention is a compound represented by formula (CA-1) below:

[C106]

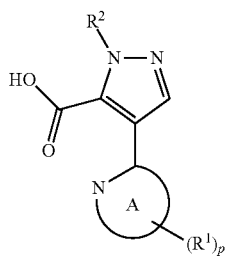
(CA-1)

[in formula (CA-1), p denotes an integer between 0 and 3; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; and ring A group represented by formula (II):

[C107]

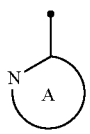
(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], or a salt of the compound, or a solvate of the compound or salt.

[14a-1] A preferred aspect of mode [14a] is a compound represented by formula (CA-1) above [in formula (CA-1), p denotes an integer between 0 and 3; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; $R^2$ denotes a methyl group; and ring A group represented by formula (II) is defined in the same way as in mode [14a] above], or a salt of the compound, or a solvate of the compound or salt.

[14a-2] A more preferred aspect of mode [14a] is a compound represented by formula (CA-1) above [in formula (CA-1), p denotes an integer between 1 and 3; $R^1$, $R^2$ and ring A group represented by formula (II) are defined in the same way as in mode [14a-1] above], or a salt of the compound, or a solvate of the compound or salt.

[14a-3] A yet more preferred aspect of mode [14a] is a compound represented by formula (CA-1) above [in formula (CA-1), p, $R^1$ and $R^2$ are defined in the same way as in mode [14a-2] above; ring A group represented by formula (II) is a thiazol-2-yl group or a pyrimidin-4-yl group; and a more specific group obtained by combining the definitions of p, $R^2$ and ring A group represented by formula (II) is a 4-(trifluoromethyl)thiazol-2-yl group, a 5-fluoro-2-methoxypyrimidin-4-yl group, a 2,5-dimethylpyrimidin-4-yl group or a 2-methylpyrimidin-4-yl group], or a salt of the compound, or a solvate of the compound or salt.

[14']

Mode no. 14' of the present invention lists the intermediate compounds shown below as preferred intermediate compounds for compounds represented by formula (CA-1) in modes [14] to [14-3] above or modes [14a] to [14a-3] above, or salts of these intermediate compounds, or solvates of the intermediate compounds or salts. The listed intermediate compounds are obtained in steps having working example numbers corresponding to the compound names. Explanations relating to the names of the compounds and the working example numbers are the same as the explanations given in mode [8'] above.

TABLE 5

| Compound | Working Example No. |
| --- | --- |
| 4-(2,5-dimethylpyrimidin-4-yl)-1-methyl-1H-pyrazole-5-carboxylic acid | 5-1 |
| 1-methyl-4-(2-methylpyrimidin-4-yl)-1H-pyrazole-5-carboxylic acid | 8 |
| 4-(5-fluoro-2-methoxypyrimidin-4-yl)-1-methyl-1H-pyrazole-5-carboxylic acid | 12 |
| 1-methyl-4-(4-(trifluoromethyl)thiazol-2-yl)-1H-pyrazole-5-carboxylic acid | 16 |

[15] A fifteenth mode of the present invention is a method for manufacturing a compound represented by formula (I) below:

[C108]

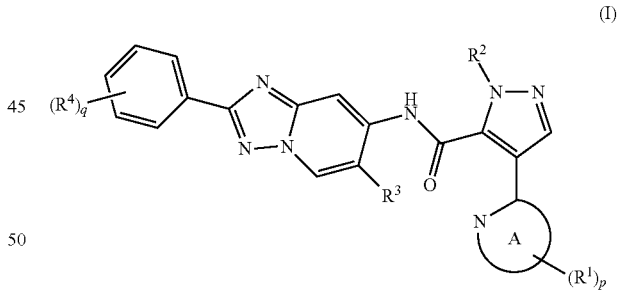
(I)

[in formula (I), p denotes an integer between 0 and 3; q denotes an integer between 0 and 2; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C109]

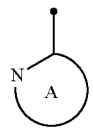
(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], the manufacturing method including stages in which a compound represented by formula (AD-1):

[C110]

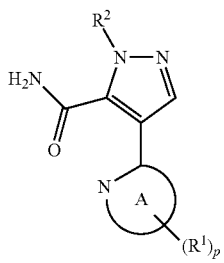
(AD-1)

[in formula (AD-1), p, $R^1$, $R^2$ and ring A group represented by formula (II) are defined in the same way as for formula (I) in mode [15]] and a 2-amino-4-iodopyridine derivative represented by formula (PY-1):

[C111]

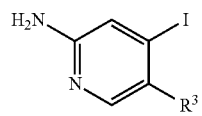
(PY-1)

[in formula (PY-1), $R^3$ denotes a hydrogen atom or a fluorine atom (a routine method for manufacturing a compound represented by formula (PY-1) is described later)] are reacted with each other in the presence of N,N-dimethyl-1,2-ethanediamine, copper iodide (CuI) and an inorganic base such as potassium carbonate or potassium phosphate using a solvent which does not take part in the reaction, such as 1,4-dioxane, tetrahydrofuran or 1,2-dimethoxyethane, at a temperature between 0° C. and a temperature at which the solvent refluxes, thereby obtaining a compound represented by formula (AD-2):

[C112]

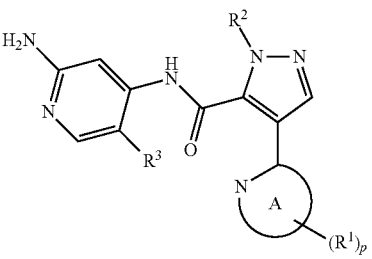
(AD-2)

[in formula (AD-2), p, $R^2$, $R^3$ and ring A group represented by formula (II) are defined in the same way as for formula (I) in mode [15]] (stage [15]-1), the compound represented by formula (AD-2) and a compound represented by formula (IM-1):

[C113]

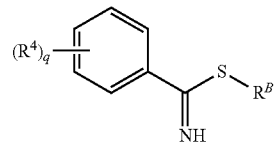
(IM-1)

[in formula (IM-1), q and $R^4$ are defined in the same way as for formula (I) in mode [15]; and $R^B$ denotes a $C_{1-6}$ alkyl group] or a salt thereof (the compound represented by formula (IM-1) and salt thereof are commercially available compounds or compounds that can be easily obtained from commercially available compounds using manufacturing methods known from literature) are reacted with each other using a solvent which does not take part in the reaction, such as dimethyl sulfoxide or pyridine, at a temperature between 0° C. and a temperature at which the solvent refluxes, thereby obtaining a compound represented by formula (AD-3):

[C114]

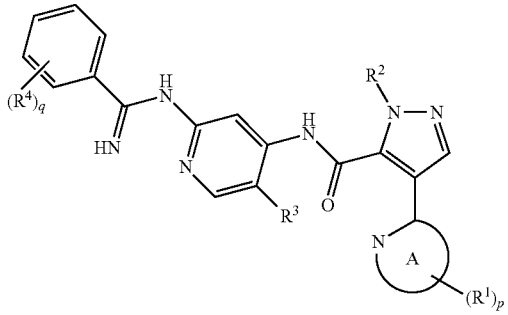
(AD-3)

[in formula (AD-3), p, q, $R^1$, $R^2$, $R^3$, $R^4$ and ring A group represented by formula (II) are defined in the same way as for formula (I) in mode [15]] (stage [15]-2), and the compound represented by formula (AD-3) is subjected to a cyclization reaction in the presence of air using a solvent which does not take part in the reaction, such as dimethyl sulfoxide (DMSO) or N-methylpyrrolidone (NMP), at a temperature between 0° C. and a temperature at which the solvent refluxes in the presence of a copper reagent such as copper iodide (CuI) or copper chloride (CuCl) (stage [15]-3), thereby obtaining the compound represented by formula (I).

[15-1] A preferred aspect of mode [15] is a method in which a compound represented by formula (I) above is manufactured [in formula (I), p, q, $R^3$ and ring A group represented by formula (II) are defined in the same way as in mode [15] above; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; $R^2$ denotes a methyl group; and $R^4$ denotes a group arbitrarily selected from among a fluorine atom, a methyl group and a methoxy group], the manufacturing method including stages in which a compound represented by formula (I) is obtained [these stages are the same as (stage [15]-1) to (stage [15]-3) in mode [15] above; the definitions of the substituent groups in the intermediates in (stage [15]-1) to (stage [15]-3) are the same as the definitions in mode [15-1], and $R^B$ in formula (IM-1) is a $C_{1-6}$ alkyl group].

[15-2] A more preferred aspect of mode [15] is a method in which a compound represented by formula (I) above is manufactured [in formula (I), p, $R^1$, $R^2$, $R^4$ and ring A group represented by formula (II) are defined in the same way as for mode [15-1] above; q denotes the integer 0; and $R^3$ denotes a fluorine atom], the manufacturing method including stages in which a compound represented by formula (I) is obtained [these stages are the same as (stage [15]-1) to (stage [15]-3) in mode [15] above; the definitions of the substituent groups in the intermediates in (stage [15]-1) to (stage [15]-3) are the same as the definitions in mode [15-2], and $R^B$ in formula (IM-1) is a $C_{1-6}$ alkyl group].

[15-3] A yet more preferred aspect of mode [15] is a method in which a compound represented by formula (I) above is manufactured [in formula (I), p, q, $R^1$, $R^2$, $R^3$ and $R^4$ are defined in the same way as for mode [15-2] above; ring A group represented by formula (II) is a thiazol-2-yl group or a pyrimidin-4-yl group; and a more specific group obtained by combining the definitions of p, $R^1$ and ring A group represented by formula (II) is a 4-(trifluoromethyl)thiazol-2-yl group, a 5-fluoro-2-methoxypyrimidin-4-yl group, a 2,5-dimethylpyrimidin-4-yl group or a 2-methylpyrimidin-4-yl group], the manufacturing method including stages in which a compound represented by formula (I) is obtained [these stages are the same as (stage [15]-1) to (stage [15]-3) in mode [15] above; the definitions of the substituent groups in the intermediates in (stage [15]-1) to (stage [15]-3) are the same as the definitions in mode [15-3], and $R^B$ in formula (IM-1) is a $C_{1-6}$ alkyl group].

[16] A sixteenth mode of the present invention is a method for manufacturing a compound represented by formula (AD-3) below:

[C115]

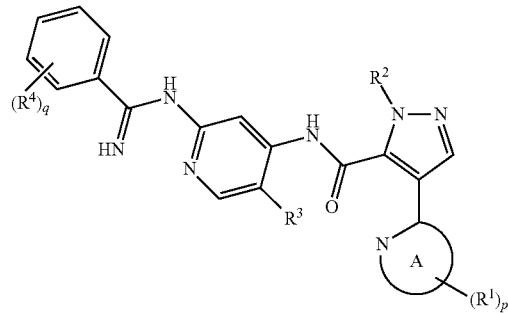

(AD-3)

[in formula (AD-3), p denotes an integer between 0 and 3; q denotes an integer between 0 and 2; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a hydrogen atom or a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C116]

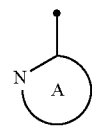

(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], the manufacturing method including stages in which a compound represented by formula (AD-1):

[C117]

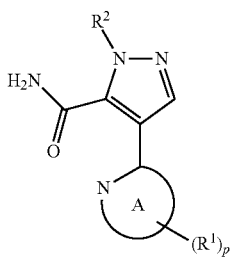

(AD-1)

[in formula (AD-1), p, $R^1$, $R^2$ and ring A group represented by formula (II) are defined in the same way as for formula (AD-3) in mode [16]] and a 2-amino-4-iodopyridine derivative represented by formula (PY-1):

[C118]

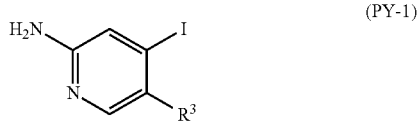
(PY-1)

[in formula (PY-1), R³ denotes a group arbitrarily selected from among a hydrogen atom and a fluorine atom (a routine method for manufacturing a compound represented by formula (PY-1) is described later)] are reacted with each other in the presence of N,N-dimethyl-1,2-ethanediamine, copper iodide (CuI) and an inorganic base such as potassium carbonate or potassium phosphate using a solvent which does not take part in the reaction, such as 1,4-dioxane, tetrahydrofuran or 1,2-dimethoxyethane, at a temperature between 0° C. and a temperature at which the solvent refluxes, thereby obtaining a compound represented by formula (AD-2):

[C119]

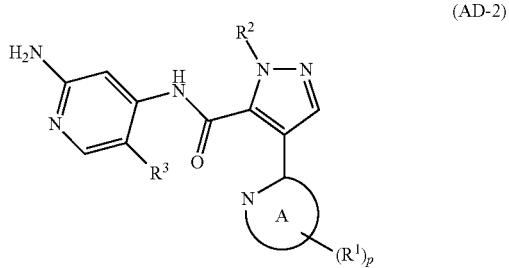
(AD-2)

[in formula (AD-2), p, $R^1$, $R^2$, $R^3$ and ring A group represented by formula (II) are defined in the same way as for formula (AD-3) in mode [16]] (stage [16]-1), and the compound represented by formula (AD-2) and a compound represented by formula (IM-1):

[C120]

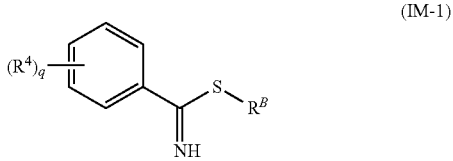
(IM-1)

[in formula (IM-1), q and $R^4$ are defined in the same way as for formula (AD-3) in mode [16]; and $R^B$ denotes a $C_{1-6}$ alkyl group] or a salt thereof (the compound represented by formula (IM-1) and salt thereof are commercially available compounds or compounds that can be easily obtained from commercially available compounds using manufacturing methods known from literature) are reacted with each other using a solvent which does not take part in the reaction, such as dimethyl sulfoxide or pyridine, at a temperature between 0° C. and a temperature at which the solvent refluxes (stage [16]-2), thereby obtaining the compound represented by formula (AD-3).

[16-1] A preferred aspect of mode [16] is a method in which a compound represented by formula (AD-3) above is manufactured [in formula (AD-3), p, q, $R^3$ and ring A group represented by formula (II) are defined in the same way as in mode [16] above; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; $R^2$ denotes a methyl group; and $R^4$ denotes a group arbitrarily selected from among a fluorine atom, a methyl group and a methoxy group], the manufacturing method including stages in which a compound represented by formula (AD-3) is obtained [these stages are the same as (stage [16]-1) and (stage [16]-2) in mode [16] above; the definitions of the substituent groups in the intermediates in (stage [16]-1) and (stage [16]-2) are the same as the definitions in mode [16-1], and $R^B$ in formula (IM-1) is a $C_{1-6}$ alkyl group].

[16-2] A more preferred aspect of mode [16] is a method in which a compound represented by formula (AD-3) above is manufactured [in formula (AD-3), p, $R^1$, $R^2$, $R^4$ and ring A group represented by formula (II) are defined in the same way as for mode [16-1] above; q denotes the integer 0; and $R^3$ denotes a fluorine atom], the manufacturing method including stages in which a compound represented by formula (AD-3) is obtained [these stages are the same as (stage [16]-1) and (stage [16]-2) in mode [16] above; the definitions of the substituent groups in the intermediates in (stage [16]-1) and (stage [16]-2) are the same as the definitions in mode [16-2], and $R^B$ in formula (IM-1) is a $C_{1-6}$ alkyl group].

[16-3] A yet more preferred aspect of mode [16] is a method in which a compound represented by formula (AD-3) above is manufactured [in formula (AD-3), p, q, $R^1$, $R^2$, $R^3$ and $R^4$ are defined in the same way as for mode [16-2] above; ring A group represented by formula (II) is a thiazol-2-yl group or a pyrimidin-4-yl group; and a more specific group obtained by combining the definitions of p, $R^1$ and ring A group represented by formula (II) is a 4-(trifluoromethyl)thiazol-2-yl group, a 5-fluoro-2-methoxypyrimidin-4-yl group, a 2,5-dimethylpyrimidin-4-yl group or a 2-methylpyrimidin-4-yl group], the manufacturing method including stages in which a compound represented by formula (AD-3) is obtained [these stages are the same as (stage [16]-1) and (stage [16]-2) in mode [16] above; the definitions of the substituent groups in the intermediates in (stage [16]-1) and (stage [16]-2) are the same as the definitions in mode [16-3], and $R^B$ in formula (IM-1) is a $C_{1-6}$ alkyl group].

[17] A seventeenth mode of the present invention is a method for manufacturing a compound represented by formula (AD-3) below:

[C121]

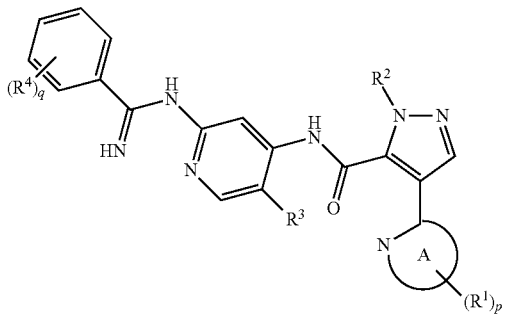

(AD-3)

[in formula (AD-3), p denotes an integer between 0 and 3; q denotes an integer between 0 and 2; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C122]

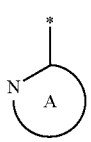

(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group], the manufacturing method including a stage in which a compound represented by formula (AD-2):

[C123]

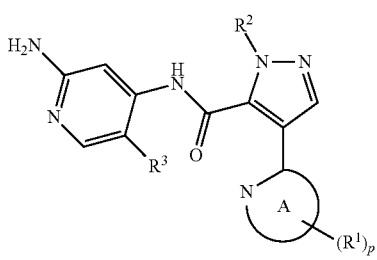

(AD-2)

[in formula (AD-2), p, $R^1$, $R^2$, $R^3$ and ring A group represented by formula (II) are defined in the same way as for formula (AD-3) in mode [17]] and a compound represented by formula (IM-1):

[C124]

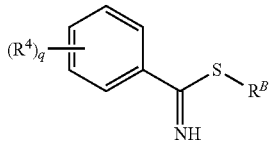

(IM-1)

[in formula (IM-1), q and $R^4$ are defined in the same way as for formula (AD-3) in mode [17]; and $R^B$ denotes a $C_{1-6}$ alkyl group] or a salt thereof (the compound represented by formula (IM-1) and salt thereof are commercially available compounds or compounds that can be easily obtained from commercially available compounds using manufacturing methods known from literature) are reacted with each other using a solvent which does not take part in the reaction, such as dimethyl sulfoxide or pyridine, at a temperature between 0° C. and a temperature at which the solvent refluxes (stage [17]-1), thereby obtaining the compound represented by formula (AD-3).

[17-1] A preferred aspect of mode [17] is a method in which a compound represented by formula (AD-3) above is manufactured [in formula (AD-3), p, q, $R^3$ and ring A group represented by formula (II) are defined in the same way as in mode [17] above; $R^1$ denotes a group arbitrarily selected from among a fluorine atom, a chlorine atom, a bromine atom, a cyano group, a methyl group, an ethyl group, an isopropyl group, a tert-butyl group, a cyclopropyl group, a difluoromethyl group, a trifluoromethyl group, a 1-hydroxyethyl group, a vinyl group, an acetyl group, a methoxy group and an ethoxyethyl group; $R^2$ denotes a methyl group; and $R^4$ denotes a group arbitrarily selected from among a fluorine atom, a methyl group and a methoxy group], the manufacturing method including a stage in which a compound represented by formula (AD-3) is obtained [this stage is the same as (stage [17]-1) in mode [17] above; the definitions of the substituent groups in the intermediate in (stage [17]-1) are the same as the definitions in mode [17-1], and $R^B$ in formula (IM-1) is a $C_{1-6}$ alkyl group].

[17-2] A more preferred aspect of mode [17] is a method in which a compound represented by formula (AD-3) above is manufactured [in formula (AD-3), p, $R^1$, $R^2$, $R^4$ and ring A group represented by formula (II) are defined in the same way as for mode [17-1] above; q denotes the integer 0; and $R^3$ denotes a fluorine atom], the manufacturing method including a stage in which a compound represented by formula (AD-3) is obtained [this stage is the same as (stage [17]-1) in mode [17] above; the definitions of the substituent groups in the intermediate in (stage [17]-1) are the same as the definitions in mode [17-2], and $R^B$ in formula (IM-1) is a $C_{1-6}$ alkyl group].

[17-3] A yet more preferred aspect of mode [17] is a method in which a compound represented by formula (AD-3) above is manufactured [in formula (AD-3), p, q, $R^1$, $R^2$, $R^3$ and $R^4$ are defined in the same way as for mode [17-2] above; ring A group represented by formula (II) is a thiazol-2-yl group or a pyrimidin-4-yl group; and a more specific group obtained by combining the definitions of p, $R^1$ and ring A group represented by formula (II) is a 4-(trifluoromethyl)thiazol-2-yl group, a 5-fluoro-2-methoxypyrimidin-4-yl group, a 2,5-dimethylpyrimidin-4-yl group or a 2-methylpyrimidin-4-yl group], the manufacturing method including a stage in which a compound represented by formula (AD-3) is obtained [this stage is the same as (stage

[17]-1) in mode [17] above; the definitions of the substituent groups in the intermediate in (stage [17]-1) are the same as the definitions in mode [17-3], and $R^B$ in formula (IM-1) is a $C_{1-6}$ alkyl group].

[18] An eighteenth mode of the present invention is a method for manufacturing a 4-heteroaryl-N-(2-phenyl-[1,2,4]triazolo[1,5-a]pyridin-7-yl)-1H-pyrazole-5-carboxylic acid amide derivative represented by formula (I) in (Scheme 1) below [in (Scheme 1), p, q, $R^1$, $R^2$, $R^3$, $R^4$, $R^B$, $R^C$, $R^D$ and ring A group represented by formula (II) are defined in the same way as modes [1] to [17] above]; and an intermediate for this manufacturing method.

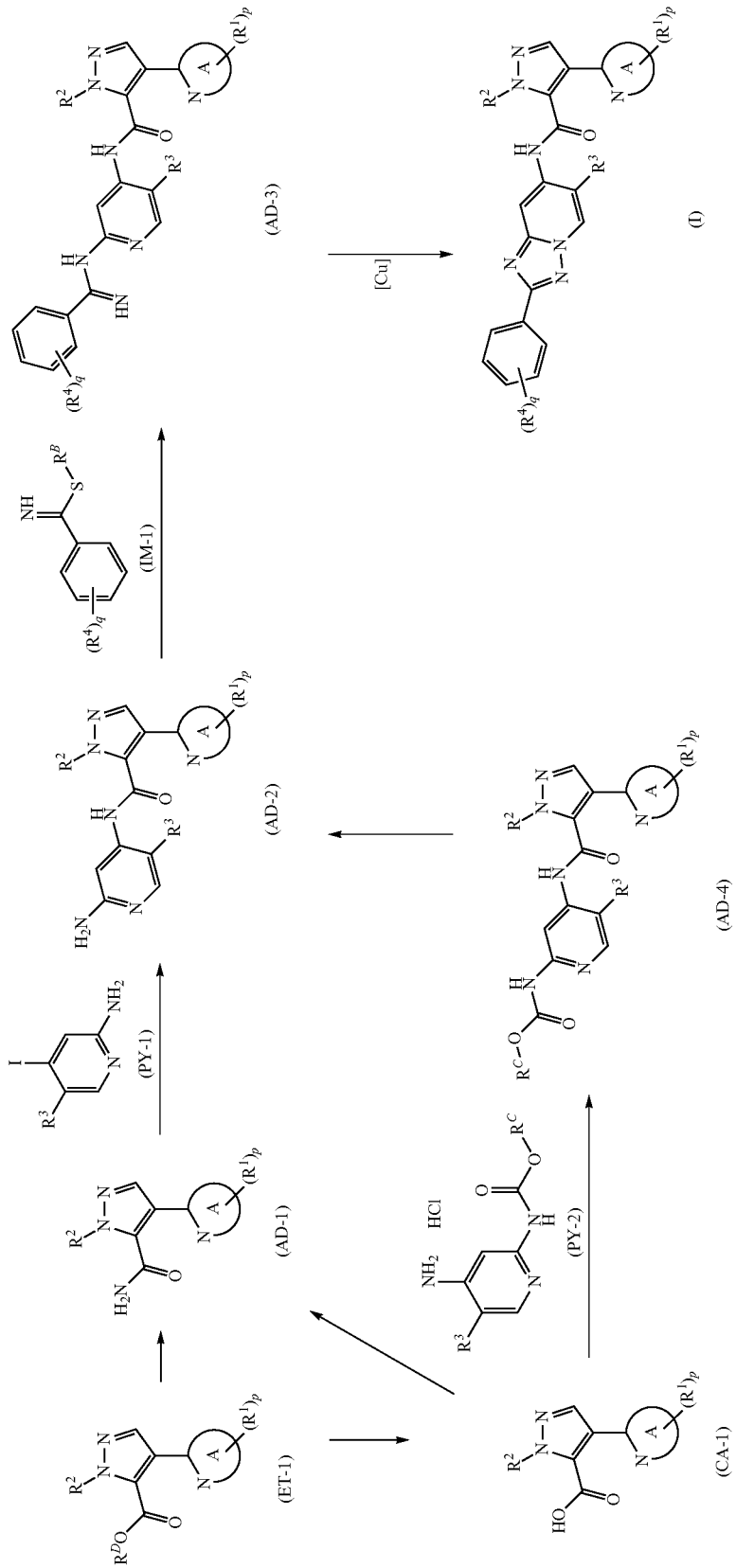

Specific explanations will now be given for the groups in the formulae in modes [1] to [18].

For example, in explanations relating to the compound of the present invention, "$C_{1-6}$" means that the number of constituent carbon atoms is between 1 and 6 and, unless explicitly stated otherwise, denotes the number of carbon atoms in a straight chain, branched chain or cyclic group. The number of constituent carbon atoms includes the total number of carbon atoms in a group that includes a straight chain or branched chain group substituted with a cyclic group or in a group that includes a cyclic group substituted with a straight chain or branched chain group. Therefore, a chain-like group means "a straight chain or branched chain having 1 to 6 constituent carbon atoms". In addition, a cyclic group means "a cyclic group in which the number of constituent carbon atoms in the ring is 1 to 6". A group that includes a chain-like group and a cyclic group means "a group having a total of 1 to 6 carbon atoms".

Unless explicitly stated otherwise, the term "halogen atom" in the present specification includes, for example, fluorine atoms, chlorine atoms, bromine atoms, iodine atoms, and the like.

Unless explicitly stated otherwise, the term "$C_{1-6}$ alkyl group" in the present specification includes, for example, methylethyl groups, propyl groups, isopropyl groups, butyl groups, isobutyl groups, sec-butyl groups, tert-butyl groups, pentyl groups, isopentyl groups, neopentyl groups, tert-pentyl3-methylbutyl groups, 1,2-dimethylpropyl groups, 1-ethylpropyl groups, hexyl groups, isohexyl groups, 1-methylpentyl groups, 2-methylpentyl groups, 3-methylpentyl groups, 1,1-dimethylbutyl groups, 1,2-dimethylbutyl groups, 2,2-dimethylbutyl groups, 1,3-dimethylbutyl groups, 2,3-dimethylbutyl groups, 3,3-dimethylbutyl groups, 1-ethylbutyl groups, 2-ethylbutyl groups, 1,1,2-trimethylpropyl groups, 1,2,2-trimethylpropyl groups, 1-ethyl-1-methylpropyl groups, 1-ethyl-2-methylpropyl groups, cyclopropyl groups, cyclobutyl groups, cyclopentyl groups, cyclohexyl groups, cyclopropylmethyl groups, cyclobutylmethyl groups, cyclopentylmethyl groups, 1-cyclopropylethyl groups, 2-cyclopropylethyl groups, 2-cyclobutylethyl groups, 2-methylcyclopropyl groups, and the like.

Unless explicitly stated otherwise, the term "halogenated" in the present specification means that 1 to 5 of the "halogen atoms" mentioned above may be present as substituent groups. In addition, the term "halogenated" may also be written as "optionally halogenated" or "halogeno".

Unless explicitly stated otherwise, the term "halogenated $C_{1-6}$ alkyl group" in the present specification means a group in which the "$C_{1-6}$ alkyl groups" mentioned above are arbitrarily substituted with 1 to 5 halogen atoms, and examples thereof include fluoromethyl groups, difluoromethyl groups, trifluoromethyl groups, 2,2,2-trifluoroethyl groups, 1,1,2,2-tetrafluoroethyl groups and pentafluoroethyl groups.

Unless explicitly stated otherwise, the term "$C_{3-8}$ cycloalkyl group" in the present specification includes, for example, cyclopropyl groups, cyclobutyl groups, cyclopentyl groups, cyclohexyl groups, cycloheptyl groups and cyclooctyl groups.

Unless explicitly stated otherwise, the term "$C_{2-6}$ alkenyl group" in the present specification includes, for example, vinyl groups, allyl groups, isopropenyl groups, 1-propen-1-yl groups, 2-methylallyl groups, butenyl groups, pentenyl groups, isopentenyl groups, hexenyl groups, 1-cyclopropen-1-yl groups, 2-cyclopropen-1-yl groups, 1-cyclobuten-1-yl groups, 1-cyclopenten-1-yl groups, 2-cyclopenten-1-yl groups, 3-cyclopenten-1-yl groups, 1-cyclohexen-1-yl groups, 2-cyclohexen-1-yl groups, 3-cyclohexen-1-yl groups, 2,4-cyclopentadien-1-yl groups, 2,5-cyclohexadien-1-yl groups, and the like.

Unless explicitly stated otherwise, the term "$C_{1-6}$ alkoxy group" in the present specification includes, for example, methoxy groups, ethoxy groups, propoxy groups, isopropoxy groups, butoxy groups, isobutoxy groups, sec-butoxy groups, tert-butoxy groups, pentyloxy groups, isopentyloxy groups, neopentyloxy groups, tert-pentyloxy groups, 1-methylbutoxy groups, 2-methylbutoxy groups, 1,2-dimethylpropoxy groups, 1-ethylpropoxy groups, hexyloxy groups, isohexyloxy groups, 1-methylpentyloxy groups, 2-methylpentyloxy groups, 3-methylpentyloxy groups, 1,1-dimethylbutyloxy groups, 1,2-dimethylbutyloxy groups, 2,2-dimethylbutyloxy groups, 1,3-dimethylbutyloxy groups, 2,3-dimethylbutyloxy groups, 3,3-dimethylbutyloxy groups, 1-ethylbutyloxy groups, 2-ethylbutyloxy groups, 1,1,2-trimethylpropyloxy groups, 1,2,2-trimethylpropyloxy groups, 1-ethyl-1-methylpropyloxy groups, 1-ethyl-2-methylpropyloxy groups, cyclopropyloxy groups, cyclobutyloxy groups, cyclopentyloxy groups, cyclohexyloxy groups, cyclopropylmethoxy groups, cyclobutylmethoxy groups, cyclopentylmethoxy groups, 1-cyclopropylethoxy groups, 2-cyclopropylethoxy groups, 2-cyclobutylethoxy groups, 2-methylcyclopropyloxy groups, and the like.

Unless explicitly stated otherwise, the term "$C_{1-6}$ alkoxy-$C_{1-6}$ alkyl group" in the present specification means groups in which the "$C_{1-6}$ alkyl groups" mentioned above are substituted with the "$C_{1-6}$ alkoxy groups" mentioned above. Unless explicitly stated otherwise, the term "$C_{1-6}$ alkoxy-$C_{1-6}$ alkyl group" in the present specification includes, for example, methoxymethyl groups, methoxyethyl groups, ethoxymethyl groups, ethoxyethyl groups, 1,1-dimethoxymethyl groups, 1,1-diethoxyethyl groups, and the like.

Unless explicitly stated otherwise, the term "hydroxy-$C_{1-6}$ alkyl group" in the present specification means groups in which the "$C_{1-6}$ alkyl groups" mentioned above are arbitrarily substituted with 1 to 5 hydroxyl groups, and examples thereof include hydroxymethyl groups, hydroxyethyl groups (specifically, 1-hydroxyethyl groups and 2-hydroxyethyl groups), hydroxypropyl groups (specifically, 1-hydroxypropyl groups, 2-hydroxypropyl groups, 3-hydroxypropyl groups, and the like) and 2-hydroxy-2-methylethyl groups.

Unless explicitly stated otherwise, the term "$C_{2-7}$ alkanoyl group" in the present specification includes, for example, acetyl groups, propionyl groups, butyryl groups, isobutyryl groups, valeryl groups, isovaleryl groups, pivaloyl groups, hexanoyl groups, heptanoyl groups, cyclopropylcarbonyl groups, cyclobutylcarbonyl groups, cyclopentylcarbonyl groups, cyclohexylcarbonyl groups, cyclopropylmethylcarbonyl groups, 2-methylcyclopropylcarbonyl groups, and the like.

Unless explicitly stated otherwise, the term "monocyclic 5- to 6-membered heteroaryl group" in the present specification means a monocyclic 5- to 6-membered heteroaryl ring group having 1 to 5 heteroatoms selected from among nitrogen atoms, sulfur atoms and oxygen atoms.

Unless explicitly stated otherwise, the term "monocyclic 5- to 6-membered heteroaryl group" in the present specification includes, for example, pyrrolyl groups, furyl groups, thienyl groups, thiazolyl groups, oxazolyl groups, 1H-imidazolyl groups, isothiazolyl groups, isoxazolyl groups, 1H-pyrazolyl groups, 1,2,4-thiadiazolyl groups, 1,2,4-oxadiazolyl groups, 1H-1,2,4-triazolyl groups, 1,2,5-thiadiazolyl groups, 1,2,5-oxadiazolyl (furazanyl) groups, 2H-1,2, 3-triazolyl groups, 1,3,4-thiadiazolyl groups, 1,3,4-oxadiazolyl groups, 4H-1,2,4-triazolyl groups, 1,2,4-thiadiazolyl groups, 1,2,4-oxadiazolyl groups, 1H-1,2,4-triazolyl groups, 1,2,3-thiadiazolyl groups, 1,2,3-oxadiazolyl groups, 1H-1,2,3-triazolyl groups, 1,2,3,4-thiatriazolyl groups, 1,2,3,4-oxatriazolyl groups, 1,2,3,5-thiatriazolyl groups, 1,2,3,5-oxatriazolyl groups, 1H-tetrazolyl groups, 2H-tetrazolyl groups, pyridinyl groups, pyridazinyl groups, pyrimidinyl groups, pyrazinyl groups, 1,2,3-triazinyl groups, 1,2,4-triazinyl groups, 1,3,5-triazinyl groups, 1,2,4,5-tetrazinyl groups, 1,2,3,4-tetrazinyl groups, 1,2,3,5-tetrazinyl groups, and the like.

Unless explicitly stated otherwise, the term "$C_{7-20}$ aralkyl group" in the present specification includes, for example, benzyl groups, phenethyl groups, diphenylmethyl groups, 2,2-diphenylethyl groups, 3-phenylpropyl groups, 4-phenylbutyl groups, 5-phenylpentyl groups, 2-biphenylmethyl groups, 3-biphenylmethyl groups, 4-biphenylmethyl groups, 1-naphthylmethyl groups, 2-naphthylmethyl groups, 2-(1-naphthyl)ethyl groups, 2-(2-naphthyl)ethyl groups, 1-indanylmethyl groups, 2-indanylmethyl groups, 1,2,3,4-tetrahydronaphthalen-1-ylmethyl groups, 1,2,3,4-tetrahydronaphthalen-2-ylmethyl groups, and the like.

Unless explicitly stated otherwise, cases in the present specification in which a cyclic group is substituted with a variable substituent group means that the variable substituent group does not bond to a specific carbon atom in the cyclic group or to a specific NH group in the cyclic group. For example, variable substituent group $R^x$ in formula A below can be substituted at any of carbon atoms i, ii, iii, iv or v in formula A, variable substituent group $R^y$ in formula B below can be substituted at either of carbon atoms vi or vii in formula B, and variable substituent group $R^z$ in formula C below can be substituted at any of carbon atoms viii, ix, x or xi in formula C.

[C126]

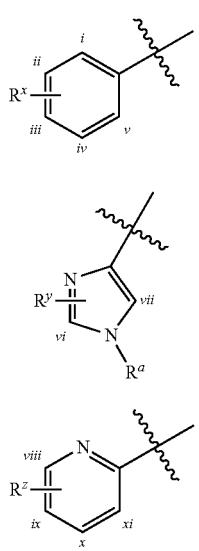

Formula A

Formula B

Formula C

In all of the modes described above, when the term "compound" is used, this can also mean "a pharmaceutically acceptable salt of the compound".

Depending on the types of substituent group, a compound of the present invention may form an acid addition salt or form a salt with a base. Such salts are not particularly limited as long as these are pharmaceutically acceptable salts, but examples thereof include metal salts, ammonium salts, salts with organic bases, salts with inorganic bases, salts with organic acids and salts with basic or acidic amino acids. Preferred examples of metal salts include alkali metal salts such as lithium salts, sodium salts, potassium salts and cesium salts, alkaline earth metal salts such as calcium salts, magnesium salts and barium salts, and aluminum salts (these include, for example, mono-salts, disodium salts and dipotassium salts). Preferred examples of salts with organic bases include salts with methylamine, ethylamine, t-butylamine, t-octylamine, diethylamine, trimethylamine, triethylamine, cyclohexylamine, dicyclohexylamine, dibenzylamine, ethanolamine, diethanolamine, triethanolamine, piperidine, morpholine, pyridine, picoline, lysine, arginine, ornithine, ethylenediamine, N-methylglucamine, glucosamine, phenylglycine alkyl esters, guanidine, 2,6-lutidine, ethanolamine, diethanolamine, triethanolamine, N,N'-dibenzylethylenediamine, and the like. Preferred examples of salts with inorganic acids include salts with hydrochloric acid, hydrobromic acid, hydroiodic acid, nitric acid, sulfuric acid, phosphoric acid, and the like. Preferred examples of salts with organic acids include salts with aliphatic monocarboxylic acids such as formic acid, acetic acid, trifluoroacetic acid, propionic acid, butyric acid, valeric acid, enanthic acid, capric acid, myristic acid, palmitic acid, stearic acid, lactic acid, sorbic acid and mandelic acid, salts with aliphatic dicarboxylic acids such as oxalic acid, malonic acid, succinic acid, fumaric acid, maleic acid, malic acid and tartaric acid, salts with aliphatic tricarboxylic acids such as citric acid, salts with aromatic monocarboxylic acids such as benzoic acid and salicylic acid, salts with aromatic dicarboxylic acids such as phthalic acid, salts with organic carboxylic acids such as cinnamic acid, glycolic acid, pyruvic acid, oxylic acid, salicylic acid and N-acetylcysteine, salts with organic sulfonic acids such as methanesulfonic acid, benzenesulfonic acid and p-toluenesulfonic acid, and acid addition salts with acidic amino acids such as aspartic acid and glutamic acid. Preferred examples of salts with basic amino acids include salts with arginine, lysine, ornithine, and the like, and preferred examples of salts with acidic amino acids include salts with aspartic acid, glutamic acid, and the like. Of these, pharmaceutically acceptable salts are preferred. For example, in cases where an acidic functional group is present in the compound, an inorganic salt such as an alkali metal salt (for example, a sodium salt, potassium salt, or the like), an alkaline earth metal salt (for example, a calcium salt, magnesium salt, barium salt, or the like), an ammonium salt, or the like, can be used, and in cases where a basic functional group is present in the compound, a salt with an inorganic acid such as hydrochloric acid, hydrobromic acid, nitric acid, sulfuric acid or phosphoric acid or a salt with an organic acid such as acetic acid, phthalic acid, fumaric acid, oxalic acid, tartaric acid, maleic acid, citric acid, succinic acid, methanesulfonic acid or p-toluenesulfonic acid can be used.

These salts can be obtained using conventional methods, for example by mixing the compound of the present invention with a solution that contains an appropriate quantity of acid or base, thereby forming the target salt, and then separating the salt by filtration or distilling off the mixed solvent. In addition, the compound of the present invention or salt thereof can form a solvate with a solvent such as water, ethanol or glycerol.

"Handbook of Pharmaceutical Salts: Properties, Selection, and Use" Stahl & Wermuth (Wiley-VCH, 2002) has been published as a review relating to salts, and detailed explanations are available in this publication. These salts can be manufactured by referring to this review.

The compound of the present invention may be present in a non-solvated form or a solvated form. In the present specification, the term "solvate" means a molecular complex that includes the compound of the present invention and one or more pharmaceutically acceptable solvent molecules (for example, water or ethanol). When the solvent molecule is water, the specific term "hydrate" is used.

In cases where the compound of the present invention has isomers such as geometric isomers, configuration isomers, tautomeric isomers, optical isomers, diastereomers, regioisomers or rotational isomers, individual isomers and mixtures thereof are encompassed by the compound of the present invention. Furthermore, in cases where optical isomers are present in the compound of the present invention, an optical isomer that has been separated from a racemate of the compound is encompassed by the compound of the present invention.

In cases where the compound of the present invention has one or more asymmetric carbon atoms, two or more diastereomers may be present. In addition, in cases where the compound of the present invention contains a "$C_{2-6}$ alkenyl group", geometric isomers (cis/trans isomers or Z/E isomers) may be present. In addition, in cases where structural isomers can be interconverted due to low energy barriers, tautomeric isomerism may occur. Examples of tautomeric isomerism include proton tautomeric isomerism in compounds having imino groups, keto groups or oxime groups.

In cases where the compound of the present invention includes geometric isomers, configuration isomers, diastereomers, conformational isomers, or the like, these may be isolated using publicly known means.

In addition, in cases where the compound of the present invention is an optically active compound, a racemate may be separated into the (+) isomer or (−) isomer [D isomer or L isomer] using a conventional optical resolution means.

In cases where the compound of the present invention includes optical isomers, diastereomers, regioisomers, rotational isomers or tautomeric isomers, each isomer can be obtained as a single compound by using a publicly known synthesis means or separation means. Examples of optical resolution means include publicly known methods such as (1) partitioning recrystallization methods, (2) diastereomer methods and (3) chiral column methods.

(1) Partitioning recrystallization method: A method in which an optical resolution agent ionically bonds to a racemate so as to obtain crystalline diastereomers, these diastereomers are separated by a partitioning recrystallization method and, if necessary, a free optically pure compound is obtained by means of a neutralization step. Examples of optical resolution agents include (+)-mandelic acid, (−)-mandelic acid, (+)-tartaric acid, (−)-tartaric acid, (+)-1-phenethylamine, (−)-1-phenethylamine, cinchonine, (−)-cinchonidine and brucine.

(2) Diastereomer method: A method in which an optical resolution agent is covalently bonded (reacted) to a racemate mixture so as to obtain a mixture of diastereomers, this mixture of diastereomers is separated into optically pure diastereomers by means of a conventional separation means (for example, partitioning recrystallization, silica gel column chromatography or high performance liquid chromatography (HPLC)), and a chemical treatment is carried out by means of a hydrolysis reaction or the like so as to remove the optical resolution agent, thereby obtaining an optically pure optical isomer. For example, in cases where the compound of the present invention has a hydroxyl group, a primary amino group or a secondary amino group in the molecule, a condensation reaction is carried out between the compound and an optically active organic acid (for example, MTPA (α-methoxy-α-(trifluoromethyl)phenylacetic acid) or (−)-methoxyacetic acid), thereby obtaining diastereomers of the corresponding ester or amide. Meanwhile, in cases where the compound of the present invention contains a carboxyl group, a condensation reaction is carried out between the compound and an optically active amine or alcohol reagent, thereby obtaining diastereomers of the corresponding amide or ester. The thus separated diastereomers are converted into optical isomers of the original compound by carrying out an acid hydrolysis reaction or base hydrolysis reaction.

(3) Chiral column method: A method in which direct optical resolution is carried out by subjecting a racemate or a salt thereof to chromatography in a chiral column (a column for separating optical isomers). For example, in the case of high performance liquid chromatography (HPLC), a mixture of optical isomers is added to a chiral column such as a CHIRAL series column manufactured by Daicel Corporation, and development is carried out using water, a variety of buffer solutions (for example, a phosphoric acid buffer solution) or organic solvents (for example, ethanol, methanol, isopropanol, acetonitrile, trifluoroacetic acid or diethylamine) either individually or as a mixed solution, thereby enabling separation of optical isomers. In addition, in the case of gas chromatography, for example, separation can be carried out using a chiral column such as CP-Chirasil-DeX CB (manufactured by GL Sciences Inc.).

The compound of the present invention may be crystalline, and the crystal form thereof may be a single form or a mixture of forms.

The compound of the present invention may be a pharmaceutically acceptable cocrystal or cocrystal salt. Here, cocrystal and cocrystal salt means a crystalline substance constituted from two or more distinct substances which are solids at room temperature and which exhibit mutually different physical properties (for example, structure, melting point, heater fusion, hygroscopic properties, solubility, stability, and the like). The cocrystal or cocrystal salt may be manufactured according to a publicly known cocrystallization method.

The compound of the present invention encompasses compounds that are labeled or substituted with isotopes (for example, hydrogen isotopes such as $^2$H and $^3$H, carbon isotopes such as $^{11}$C, $^{13}$C and $^{14}$C, chlorine isotopes such as $^{36}$Cl, fluorine isotopes such as $^{18}$F, iodine isotopes such as $^{123}$I and $^{125}$I, nitrogen isotopes such as $^{13}$N and $^{15}$N, oxygen isotopes such as $^{15}$O, $^{17}$O and $^{18}$O, phosphorus isotopes such as $^{32}$P, and sulfur isotopes such as $^{35}$S).

If labeled or substituted with certain types of isotope (for example, positron-emitting isotopes such as $^{11}$C, $^{18}$F, $^{15}$O and $^{13}$N), the compound of the present invention can be used as, for example, a tracer (PET tracer) used in positron emission tomography (PET), and is useful in fields such as medical diagnostics.

If labeled or substituted with certain types of isotopic label, the compound of the present invention is useful in tissue distribution research for drugs and/or substrates. For example, $^3$H and $^{14}$C are useful for such research purposes due to labeling or substitution being easy and detection means being simple.

If isotopically labeled, the compound of the present invention can be obtained using conventional techniques that are known by persons skilled in the art or by methods similar to the synthesis methods disclosed in the working examples described below. In addition, obtained isotopically labeled compounds can be used instead of unlabeled compounds in pharmacological tests.

[Methods for Manufacturing Compounds Represented by Formula (ET-1), Formula (PY-1) and Formula (PY-2) and Separate Method for Manufacturing Compound Represented by Formula (AD-1) in the Present Invention]

Detailed explanations will now be given of methods for manufacturing compounds represented by formula (ET-1), formula (PY-1) and formula (PY-2) in (Scheme 2) below and a separate method for manufacturing a compound represented by formula (AD-1) in the present invention. In the present invention, compounds represented by formula (ET-1), formula (PY-1), formula (PY-2) and formula (AD-1), salts of these compounds and solvates of these compounds and salts can be easily manufactured by combining ordinary known chemical manufacturing methods that use, as starting materials or synthesis intermediates, commercially available compounds or compounds able to be easily obtained from commercially available compounds using manufacturing methods known from literature, and can be manufactured according to the representative manufacturing methods shown below. In addition, the present invention is in no way limited to the manufacturing methods explained below.

[C127] (Scheme 2)
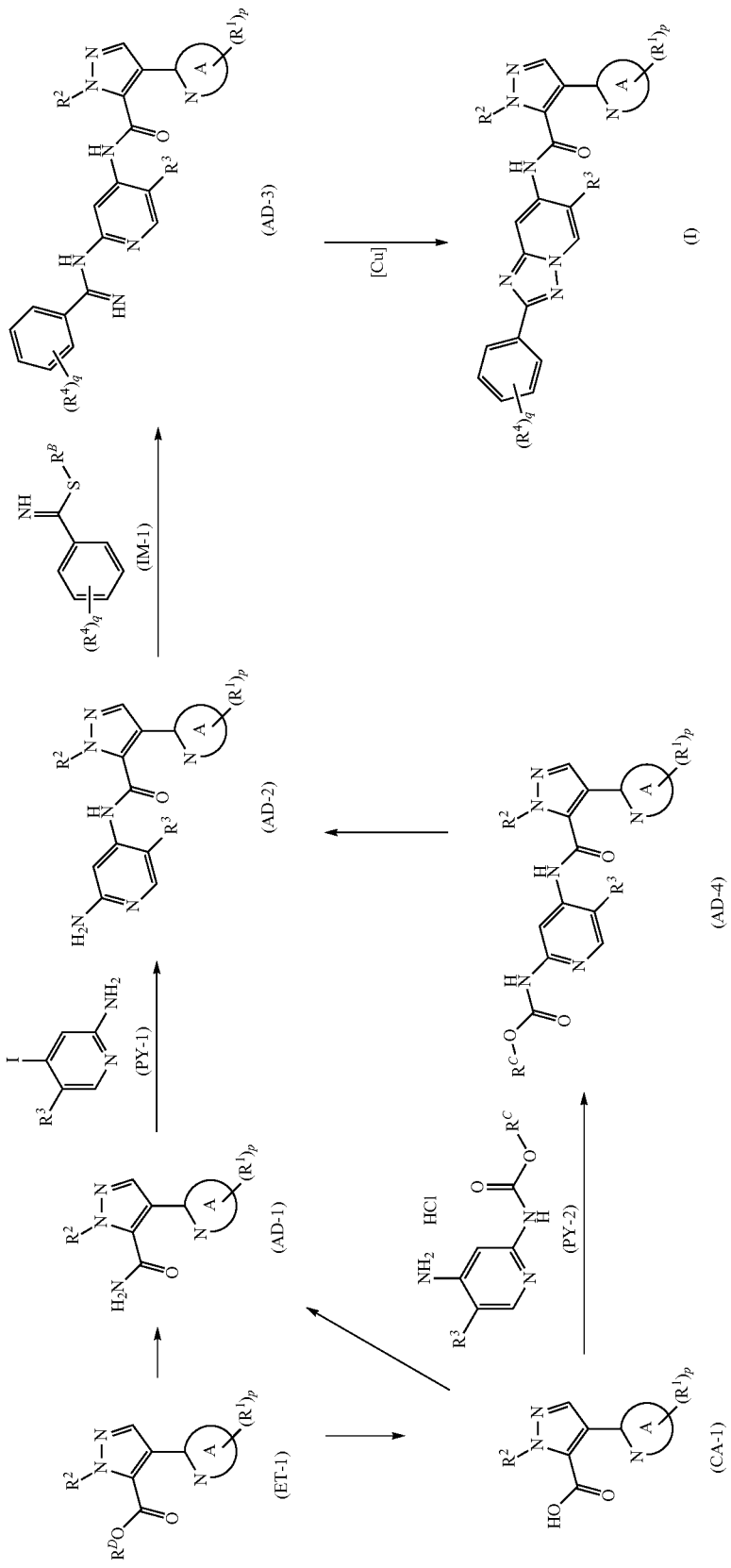

Unless explicitly stated otherwise, the definitions of p, $R^1$, $R^2$, $R^3$, $R^B$, $R^C$, $R^D$ and ring A represented by formula (II) in the formulae in the manufacturing methods for compounds represented by formula (ET-1), formula (PY-1), formula (PY-2) and formula (AD-1) are the same as the definitions described in modes [1] to [18] above. Unless explicitly stated otherwise, the definition of $R^A$ in the manufacturing methods is a $C_{1-6}$ alkyl group (for example, a methyl group or ethyl group), a $C_{6-14}$ aryl group (for example, a phenyl group) or a $C_{7-20}$ aralkyl group (for example, a benzyl group). Unless explicitly stated otherwise, the definition of X in the manufacturing methods is a halogen atom.

In the manufacturing methods described below, raw material compounds used in the manufacture of compounds represented by formula (ET-1), formula (PY-1), formula (PY-2) and formula (AD-1) may form salts, and examples of such salts include salts similar to the salts of formula (I) above. In addition, raw material compounds used in the manufacture of compounds represented by formula (ET-1), formula (PY-1), formula (PY-2) and formula (AD-1) may be used in subsequent reactions either as reaction solutions or as purified products, but can be isolated from reaction mixtures using conventional methods, and can be easily purified using publicly known separation means such as extraction, concentration, neutralization, filtration, distillation, recrystallization or chromatography.

Examples of solvents able to be used in the recrystallization mentioned above include water; alcohols such as methanol, ethanol, 2-propanol and butanol; ethers such as diethyl ether, tetrahydrofuran and 1,4-dioxane; hydrocarbons such as n-hexane, cyclohexane and heptane; aromatic hydrocarbons such as benzene, toluene and xylene; amides such as N,N-dimethylformamide, N,N-dimethylacetamide and 1,3-dimethyl-2-imidazolidinone; halogenated hydrocarbons such as chloroform, methylene chloride and 1,2-dichloroethane; nitriles such as acetonitrile; ketones such as acetone and diphenyl ketone; esters such as methyl acetate and ethyl acetate; sulfoxides such as dimethyl sulfoxide; and organic acids such as acetic acid, trifluoroacetic acid, methanesulfonic acid and p-toluenesulfonic acid. It is possible to use one of these solvents in isolation or a mixture of two or more types thereof at appropriate proportions, such as 1:1 to 1:10. In addition, in cases where the compounds in the formulae are commercially available, it is possible to use commercially available compounds without further modification or use compounds manufactured using publicly known methods or methods based on such publicly known methods.

In cases where substituent groups present in compounds represented by formula (ET-1), formula (PY-1), formula (PY-2) and formula (AD-1) contain variable functional groups (for example, carboxyl groups, amino groups, hydroxyl groups, carbonyl groups, mercapto groups, $C_{1-6}$ alkoxycarbonyl groups, $C_{6-14}$ aryloxycarbonyl groups, $C_{7-20}$ aralkyloxycarbonyl groups, sulfo groups (—$SO_2OH$), halogen atoms, and the like), a variety of compounds can be manufactured by converting these functional groups using publicly known methods or methods based on such publicly known methods.

A "carboxyl group" can be converted by means of a reaction such as esterification, chemical reduction, amidation, or conversion into an optionally protected amino group.

An "amino group" can be converted by means of a reaction such as amidation, sulfonylation, nitrosation, alkylation, arylation or imidation.

A "hydroxyl group" can be converted by means of a reaction such as esterification, carbamoylation, sulfonylation, alkylation, arylation, oxidation or halogenation.

A "carbonyl group" can be converted by means of a reaction such as chemical reduction, oxidation, imination (including oximation and hydrazonation), (thio)ketalation, alkylidenation and thiocarbonylationation.

A "mercapto (—SH) group" can be converted by means of a reaction such as alkylation or oxidation.

A "$C_{1-6}$ alkoxycarbonyl group", "$C_{6-14}$ aryloxycarbonyl group" or "$C_{7-20}$ aralkyloxycarbonyl group" can be converted by means of a reaction such as chemical reduction or hydrolysis.

A "sulfo (—$SO_2OH$) group" can be converted by means of a reaction such as sulfonamidation or chemical reduction.

A "halogen atom" can be converted by means of, for example, a variety of nucleophilic substitution reactions, a variety of coupling reactions, and the like.

In cases where a compound is obtained in a free form in the reactions mentioned above, the compound may be converted into a salt using a conventional method, and in cases where a compound is obtained in the form of a salt, the salt may be converted into a free compound or another salt using a conventional method.

These functional groups may be converted according to methods disclosed in, for example, Richard C. Larock et al., "Comprehensive Organic Transformations", second edition, October 1999 (Wiley-VCH).

In addition, in the reactions in the methods for manufacturing compounds represented by formula (ET-1), formula (PY-1), formula (PY-2) and formula (AD-1) and the reactions used to synthesize the raw material compounds in the present invention, in cases where a reactive group such as a hydroxyl group (an alcoholic hydroxyl group, phenolic hydroxyl group, heterocyclic hydroxyl group, or the like), an amino group, a carboxyl group or a thiol group is present as a substituent group, it is possible to protect these groups as appropriate in the reaction steps and remove the protecting groups at an appropriate stage.

Examples of protecting groups able to be used for these hydroxyl groups (alcoholic hydroxyl groups, phenolic hydroxyl groups, heterocyclic hydroxyl groups, and the like), include $C_{1-6}$ alkyl groups such as methyl groups, ethyl groups, n-propyl groups, isopropyl groups, n-butyl groups and tert-butyl groups; alkoxyalkyl groups such as methoxymethyl (MOM) groups and methoxyethoxymethyl (MEM) groups; tetrahydropyranyl (THP) groups; $C_{7-20}$ aralkyl groups such as benzyl (Bn) groups and triphenylmethyl (Tr) groups; silyl groups such as trimethylsilyl (TMS) groups, triethylsilyl (TES) groups, t-butyldimethylsilyl (TBDMS) groups and t-butyldiphenylsilyl (TBDPS) groups; alkanoyl groups such as acetyl (Ac) groups, ethylcarbonyl groups and pivaloyl (Piv) groups; $C_{7-20}$ aralkylcarbonyl groups such as benzylcarbonyl groups; aroyl groups such as benzoyl (Bz) groups; alkoxycarbonyl groups such as methoxycarbonyl groups, ethoxycarbonyl groups and t-butoxycarbonyl (Boc) groups; and $C_{7-20}$ aralkyloxycarbonyl groups such as benzyloxycarbonyl (Z) groups.

Examples of protecting groups able to be used for these amino groups (—$NH_2$ groups) or imino groups (—NH— groups) include alkanoyl groups such as acetyl (Ac) groups, ethylcarbonyl groups and pivaloyl (Piv) groups; alkoxycarbonyl groups such as methoxycarbonyl groups, ethoxycarbonyl groups and t-butoxycarbonyl (Boc) groups; allyloxycarbonyl (Alloc) groups; fluorenylmethoxycarbonyl (Fmoc) groups; phenyloxycarbonyl groups; $C_{7-20}$ aralkyloxycarbonyl groups such as benzyloxycarbonyl (Z) groups, para-methoxybenzyloxycarbonyl groups and para-nitrobenzoyloxycarbonyl groups; $C_{7\text{-}20}$ aralkyl groups such as benzyl (Bn) groups and triphenylmethyl (Tr) groups; aroyl groups such as benzoyl (Bz) groups; $C_{7\text{-}20}$ aralkylcarbonyl groups such as benzylcarbonyl groups; sulfonyl groups such as methanesulfonyl (Ms) groups, p-toluenesulfonyl (Ts) groups, 2,4-dinitrobenzenesulfonyl (Nos) groups and benzenesulfonyl (Bs) groups; 2-(trimethylsilyl)ethoxymethyl (SEM) groups; phthaloyl (Pht) groups; and N,N-dimethylaminomethylene groups.

Examples of protecting groups able to be used for these carboxyl groups (—COOH groups) include alkyl groups such as methyl groups, ethyl groups, n-propyl groups, isopropyl groups, n-butyl groups and tert-butyl groups; alkenyl groups such as allyl groups; aryl groups such as phenyl (Ph) groups; $C_{7\text{-}20}$ aralkyl groups such as benzyl (Bn) groups and triphenylmethyl (Tr) groups; and silyl groups such as trimethylsilyl (TMS) groups, triethylsilyl (TES) groups, t-butyldimethylsilyl (TBDMS) groups and t-butyldiphenylsilyl (TBDPS) groups.

Examples of protecting groups able to be used for these thiol groups (—SH groups) include alkyl groups such as methyl groups, ethyl groups, n-propyl groups, isopropyl groups, n-butyl groups and tert-butyl groups; $C_{7\text{-}20}$ aralkyl groups such as benzyl (Bn) groups and triphenylmethyl (Tr) groups; alkanoyl groups such as acetyl (Ac) groups, ethylcarbonyl groups and pivaloyl (Piv) groups; and aroyl groups such as benzoyl (Bz) groups.

Methods for introducing and removing such protecting groups are carried out as appropriate according to the type of group to be protected and the type of protecting group, but it is possible to use, for example, a method disclosed in Greene et al., "Protective Groups in Organic Synthesis", fourth edition, 2007 (John Wiley & Sons).

As a method for deprotecting a protecting group, it is possible to hydrolyze and deprotect acyl type protecting groups, for example alkanoyl groups such as acetyl (Ac) groups, ethylcarbonyl groups and pivaloyl (Piv) groups; alkoxycarbonyl groups such as methoxycarbonyl groups, ethoxycarbonyl groups and t-butoxycarbonyl (Boc) groups; and aroyl groups such as benzoyl (Bz) groups, using, for example, an appropriate base such as an alkali metal hydroxide, such as lithium hydroxide, sodium hydroxide or potassium hydroxide.

Alkoxyalkyl protecting groups such as methoxymethyl (MOM) groups, methoxyethoxymethyl (MEM) groups and tetrahydropyranyl (THP) groups; alkoxycarbonyl protecting groups such as t-butoxycarbonyl (Boc) groups; $C_{7\text{-}20}$ aralkyloxycarbonyl protecting groups such as benzyloxycarbonyl (Z) groups and para-methoxybenzyloxycarbonyl groups; and silyl protecting groups such as trimethylsilyl (TMS) groups, triethylsilyl (TES) groups and t-butyldimethylsilyl (TBDMS) groups can be deprotected using an appropriate acid such as acetic acid, hydrochloric acid, hydrobromic acid, sulfuric acid, phosphoric acid, trifluoroacetic acid or trifluoromethanesulfonic acid, or a combination of these acids.

In addition, these silyl protecting groups can be deprotected using an appropriate reagent that generates fluoride ions ($F^-$), for example a reagent such as tetrabutyl ammonium fluoride or hydrogen fluoride.

$C_{7\text{-}20}$ aralkyloxycarbonyl groups such as benzyloxycarbonyl (Z) groups, para-methoxybenzyloxycarbonyl groups and para-nitrobenzoyloxycarbonyl groups and $C_{7\text{-}20}$ aralkyl groups such as benzyl (Bn) groups can be deprotected by means of, for example, hydrogenolysis using a palladium-carbon (Pd—C) catalyst.

In addition, benzyl groups can also be deprotected by, for example, Birch reduction in liquid ammonia using metallic sodium.

Triphenylmethyl (Tr) groups can be deprotected using an appropriate acid such as acetic acid, hydrochloric acid, hydrobromic acid, sulfuric acid, phosphoric acid, trifluoroacetic acid or trifluoromethanesulfonic acid, or a combination of these acids. In addition, triphenylmethyl (Tr) groups can be deprotected by Birch reduction in liquid ammonia using metallic sodium or metallic lithium or by hydrogenolysis using a palladium-carbon catalyst.

Sulfonyl (—$SO_2$—) groups can be deprotected by, for example, one-electron reduction at a low temperature using Na/anthracene or Na/naphthalene, or Birch reduction in liquid ammonia using metallic sodium or metallic lithium.

In addition, among sulfonyl groups, 2-nitrobenzenesulfonyl (Ns) groups can be deprotected under mild conditions by, for example, reacting with a thiol in the presence of a basic reagent such as potassium carbonate or triethylamine.

These methods for deprotecting protecting groups are merely examples, and deprotection can be carried out using, for example, a method disclosed in Greene et al., "Protective Groups in Organic Synthesis", fourth edition, 2007 (John Wiley & Sons) or using articles that have been publicly expressed.

Unless explicitly stated otherwise, reaction conditions in the methods for manufacturing compounds represented by formula (ET-1), formula (PY-1), formula (PY-2) and formula (AD-1) described below are as follows. The reaction temperature is not limited as long as this temperature falls within the range between −78° C. and the temperature at which the solvent refluxes. The reaction duration is not limited as long as this duration is sufficient for the reaction to progress adequately.

With respect to the reaction temperature in the manufacturing methods disclosed in the present specification, unless explicitly stated otherwise, the expression "at a temperature between 0° C. and a temperature at which the solvent refluxes" means a temperature within a range between 0° C. and the temperature at which the solvent (or mixed solvent) used in the reaction refluxes. For example, in cases where methanol is used as the solvent, "at a temperature between 0° C. and a temperature at which the solvent refluxes" means a temperature within a range between 0° C. and the temperature at which methanol refluxes. Similarly, the expression "at a temperature between 0° C. and a temperature at which the reaction solution refluxes" means a temperature within a range between 0° C. and a temperature at which the reaction solution refluxes.

In addition, the steps in the methods for manufacturing compounds represented by formula (ET-1), formula (PY-1), formula (PY-2) and formula (AD-1) may be carried out in the absence of a solvent or by dissolving or suspending raw material compounds prior to the reaction in an appropriate solvent which does not take part in the reaction. Specific examples of solvents that do not take part in the reaction include water; saturated hydrocarbon-based solvents such as cyclohexane and hexane; aromatic hydrocarbon-based solvents such as benzene, chlorobenzene, toluene and xylene; alcoholic solvents such as methanol, ethanol, 1-propanol, 2-propanol, tert-butyl alcohol and 2-methoxyethanol; polar amide-based solvents such as N,N-dimethylformamide, N,N-dimethylacetamide, hexamethylphosphoric triamide and 1,3-dimethyl-2-imidazolidinone; sulfoxide-based solvents such as dimethyl sulfoxide; nitrile-based solvents such as acetonitrile and propionitrile; ether-based solvents such as diethyl ether, diisopropyl ether, diphenyl ether, tetrahydrofuran, 1,4-dioxane and 1,2-dimethoxyethane; ester-based solvents such as methyl acetate, ethyl acetate and butyl acetate; ketone-based solvents such as acetone and methyl ethyl ketone; halogenated hydrocarbon-based solvents such as dichloromethane, chloroform, carbon tetrachloride and 1,2-dichloroethane; basic solvents such as triethylamine, N,N-diisopropylethylamine, pyridine and lutidine; acid anhydrides such as acetic anhydride; organic acids such as formic acid, acetic acid, propionic acid, trifluoroacetic acid and methanesulfonic acid; and inorganic acids such as hydrochloric acid and sulfuric acid. It is possible to use one of these solvents in isolation or a mixture of appropriate proportions of two or more of these solvents, selected according to reaction conditions. Unless explicitly stated otherwise, the term "a solvent which does not take part in the reaction" in the manufacturing method in the present specification means that it is possible to use a single type of solvent in isolation or use a mixture of appropriate proportions of two or more solvents, selected according to reaction conditions.

Specific examples of bases (or deoxidizing agents) able to be used in the methods for manufacturing compounds represented by formula (ET-1), formula (PY-1), formula (PY-2) and formula (AD-1) include inorganic bases such as lithium hydroxide, sodium hydroxide, potassium hydroxide, magnesium hydroxide, lithium carbonate, sodium carbonate, potassium carbonate, cesium carbonate, calcium carbonate and sodium hydrogen carbonate; organic bases such as triethylamine, N,N-diisopropylethylamine, tributylamine, cyclohexyldimethylamine, pyridine, lutidine, 4-dimethylaminopyridine (DMAP), N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and imidazole; metal alkoxides such as sodium methoxide, sodium ethoxide, potassium tert-butoxide and sodium tert-butoxide; alkali metal hydroxides such as sodium hydroxide and potassium hydroxide; metal amides such as sodium amide, lithium diisopropylamide and lithium hexamethyldisilazide; and organic lithium reagents such as methyl lithium, n-butyl lithium, sec-butyl lithium and tert-butyl lithium. In addition, specific examples of acids and acid catalysts able to be used in the method for manufacturing the compound of the present invention include inorganic acids such as hydrochloric acid, sulfuric acid, nitric acid, hydrobromic acid and phosphoric acid; organic acids such as acetic acid, trifluoroacetic acid, oxalic acid, phthalic acid, fumaric acid, tartaric acid, maleic acid, citric acid, succinic acid, methanesulfonic acid, p-toluenesulfonic acid and 10-camphorsulfonic acid; and Lewis acids such as boron trifluoride ether complexes, zinc iodide, anhydrous aluminum chloride, anhydrous zinc chloride and anhydrous iron chloride. However, acids and acid catalysts able to be used in the method for manufacturing the compound of the present invention are not necessarily limited to those listed above.

Salts represented by formula (ET-1), formula (PY-1), formula (PY-2) and formula (AD-1) can be manufactured using publicly known means, for example, in cases where compounds represented by formula (ET-1), formula (PY-1) and formula (PY-2) are basic compounds, it is possible to manufacture the salts mentioned above by adding an inorganic acid (a mineral acid) such as hydrochloric acid, hydrobromic acid, nitric acid, sulfuric acid or phosphoric acid or an organic acid such as formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid, and in cases where compounds represented by formula (CA-1), formula (PY-1) and formula (PY-2) are acidic compounds, it is possible to manufacture the salts mentioned above by adding an organic base such as ammonia, trimethylamine, triethylamine, pyridine, picoline, 2,6-lutidine, ethanolamine, diethanolamine, triethanolamine, cyclohexylamine, dicyclohexylamine, N,N-diisopropylethylamine, N,N'-dibenzylethylenediamine or a N,N-dialkylaniline or an inorganic base such as lithium carbonate, sodium carbonate, potassium carbonate, cesium carbonate, lithium hydroxide, sodium hydroxide, potassium hydroxide or sodium hydrogen carbonate.

<Manufacturing Method A>

Method for Manufacturing Ester Derivative Represented by Formula (ET-1):

[C128]

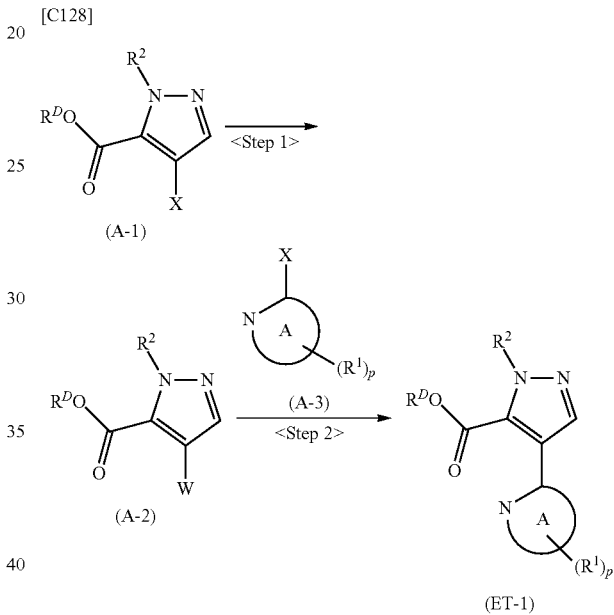

<Step 1>
<W=Boronic Acid Ester>

A boronic acid ester represented by formula (A-2) can be manufactured using a method known from literature, for example, according to the method disclosed in "The Journal of Organic Chemistry", 60, 7508-2665, 1995, by subjecting a compound represented by formula (A-1) to a reaction in the presence of a diboron ester such as bis(pinacolato)diboron or bis(neopentyl glycolato) diboron, in the presence of a palladium catalyst such as palladium (II) acetate, palladium tetrakis(triphenylphosphine), dipalladium tri (dibenzylideneacetone), [1,1'-bis(diphenylphosphino)ferrocene]dichloro palladium (II) or a [1,1'-bis(diphenylphosphino)ferrocene]dichloro palladium (II)-dichloromethane complex, in the presence or absence of a phosphine-based reagent such as triphenylphosphine, tri(tert-butyl)phosphine, tri(o-tolyl)phosphine or 2-dicyclohexylphosphino-2',6'-dimethoxybiphenyl and an organic or inorganic base such as triethylamine, N,N-diisopropylethylamine, potassium carbonate or potassium acetate or in the presence or absence of tetramethyl ammonium chloride, tetrabutyl ammonium chloride or the like instead of a phosphine-based reagent, in a solvent which does not take part in the reaction, such as toluene, N,N-dimethylformamide, dimethyl sulfoxide or 1,4-dioxane, or a mixture of these solvents, at a temperature between 0° C. and a temperature at which the solvent refluxes.

<W=Boronic Acid>

A boronic acid represented by formula (A-2) can be manufactured using a method known from literature, for example, according to the method disclosed in "Chemische Berichte" 42, 3090, 1909, by using a solvent which does not take part in the reaction, such as toluene, tetrahydrofuran or 1,4-dioxane, or a mixture of these solvents, in the presence of a Grignard reagent such as an alkyl lithium compound, such as n-butyl lithium or sec-butyl lithium, or isopropyl magnesium chloride or in the presence of metallic magnesium, adding a trialkyl borate such as trimethyl borate or triisopropyl borate, subjecting a compound represented by formula (A-1) to a reaction at a temperature between −78° C. and room temperature, then adding an acid such as hydrochloric acid or sulfuric acid, and carrying out a reaction at a temperature between 0° C. and a temperature at which the solvent refluxes.

<W=Trifluoroborate Salt>

A trifluoroborate salt represented by formula (A-2) can be manufactured using a method known from literature, for example, according to the method disclosed in "Chemical Reviews", 108, 288-325, 2008, by subjecting the boronic acid ester or boronic acid represented by formula (A-2), which are obtained in the methods mentioned above, to a reaction in the presence of potassium hydrogen difluoride (KHF$_2$) using a solvent which does not take part in the reaction, such as methanol, ethanol or water, or a mixture of these solvents, at a temperature between 0° C. and a temperature at which the solvent refluxes.

<W=Boronic Acid N-Methyliminodiacetic Acid (MIDA) Ester>

A boronic acid N-methyliminodiacetic acid (MIDA) ester represented by formula (A-2) can be manufactured using a method known from literature, for example, according to the method disclosed in "The Journal of Organometallic Chemistry", 307 (1), pages 1-6, 1986, by subjecting the boronic acid represented by formula (A-2), which is obtained in the method mentioned above, to a reaction in the presence of N-methyliminodiacetic acid (MIDA), using a solvent which does not take part in the reaction, such as benzene, toluene, xylene or dimethyl sulfoxide, or a mixture of these solvents, at a temperature between 0° C. and a temperature at which the solvent refluxes.

<Step 2>

A compound represented by formula (ET-1) can be manufactured using a method known from literature, for example, according to "The Fifth Series of Experimental Chemistry, 18. Organic Compound Synthesis VI—Organic Synthesis Using Metals —", pages 327-352, 2004, Maruzen and "Journal of Medicinal Chemistry" 48(20), pages 6326-6339, 2005, by subjecting a compound represented by formula (A-2), which was obtained in <Step 1> in <Manufacturing Method A>, and a halogenated heteroaryl derivative represented by formula (A-3) to a reaction in the presence of a palladium catalyst such as palladium (II) acetate (Pd(OAc)$_2$), palladium tetrakis(triphenylphosphine) (Pd(PPh$_3$)$_4$), dipalladium tri(dibenzylideneacetone) ((dba)$_3$Pd$_2$), palladium bis(dibenzylideneacetone) ((dba)$_2$Pd) or [1,1′-bis(diphenylphosphino)ferrocene]dichloro palladium (II) (Pd(dppf)Cl$_2$), a phosphine-based reagent such as triphenylphosphine, tri(tert-butyl)phosphine, tri(o-tolyl)phosphine, 2-dicyclohexylphosphino-2′,6′-dimethoxybiphenyl or 2-dicyclohexylphosphino-2′,4′,6′-triisopropylbiphenyl and an organic or inorganic base such as triethylamine, N,N-diisopropylethylamine, potassium phosphate, potassium carbonate or cesium carbonate, using a solvent which does not take part in the reaction, such as toluene, xylene, N,N-dimethylformamide, N,N-dimethylacetamide, 1,2-dimethoxyethane, acetonitrile (acetonitrile/water), 1,4-dioxane (1,4-dioxane/water) or tetrahydrofuran (tetrahydrofuran/water), or a mixture of these solvents, at a temperature between 0° C. and a temperature at which the solvent refluxes. In addition, a compound represented by formula (ET-1) can be manufactured using a similar method, using tetramethyl ammonium chloride, tetrabutyl ammonium chloride, or the like, instead of the phosphine-based reagent.

<Manufacturing Method B>

Method for Manufacturing Pyridine Acid Derivative Represented by Formula (PY-1) (Formula (PY-1-1) in Cases where R$^3$ is a Fluorine Atom):

[C129]

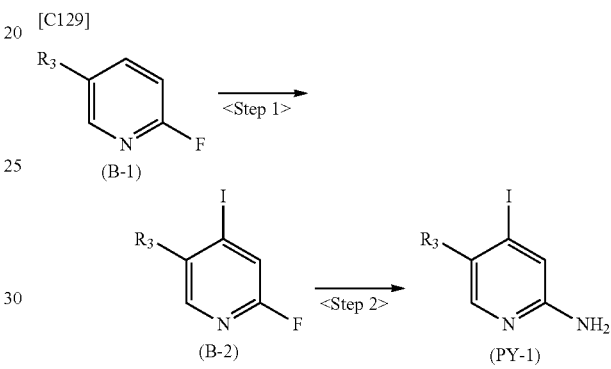

<Step 1>

A compound represented by formula (B-2) can be manufactured according to a method known from literature, for example, a method disclosed in "Bioorganic & Medicinal Chemistry Letters", 22(10), pages 3431-3436, 2012 or "Step (A) in Example 56 on page 116 of WO 2011/073845" (published 23 Jun. 2011), by adding a compound represented by formula (B-1) (in cases where R$^3$ is a fluorine atom, the starting material is 2,5-difluoropyridine [CAS No.:84476-99-3]) at a temperature of −78° C. to a mixed solution of lithium diisopropylamide (LDA) prepared from N,N-diisopropylamine and n-butyl lithium (an n-hexane solution) in a solvent that is inert in the reaction, such as tetrahydrofuran, diethyl ether or 1,2-dimethoxyethane, or a mixture of these solvents, stirring for 3 hours, further adding iodine, and carrying out a reaction at a temperature between −78° C. and 0° C.

<Step 2>

A compound represented by formula (PY-1) can be manufactured according to a method known from literature, for example, a method disclosed in "Synthesis", 12, pages 905-908, 1989, by subjecting the compound represented by formula (B-2), which was obtained in <Step 1> in <Manufacturing Method B> to a sealed tube reaction at a temperature between 0° C. and 150° C. in the presence of aqueous ammonia using a solvent that is inert in the reaction, such as 1,4-dioxane.

<Manufacturing Method C>

Method for Manufacturing Pyridine Acid Derivative Represented by Formula (PY-2):

[In cases where R$^3$ is F, the starting material is 2-bromo-5-fluoropyridine [CAS No.: 41404-58-4], which is represented by formula (C-1). In cases where R$^3$ is H, the starting material is 2-amino-isonicotinic acid ethyl ester [CAS No.: 13362-30-6], which is represented by formula (C-4).]

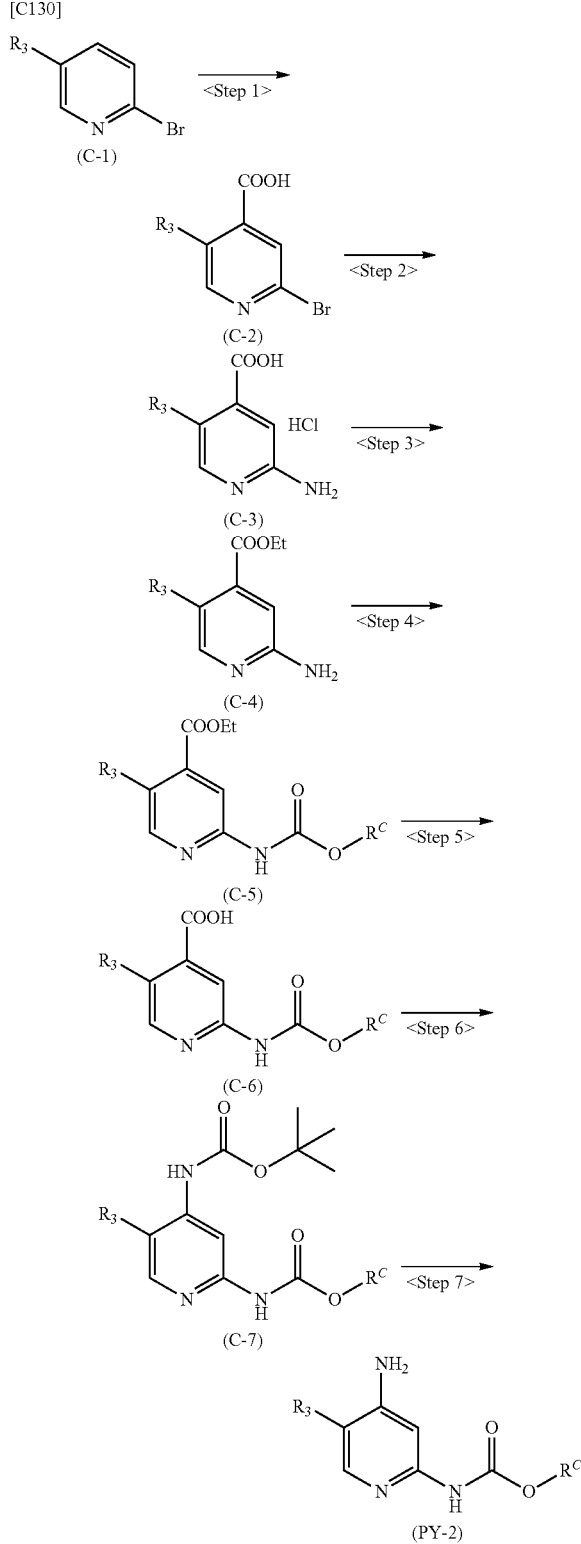

<Step 1>
According to a method known from literature, for example, a method disclosed in WO 2008/126899 (published on 23 Oct. 2008), n-butyl lithium (an n-hexane solution) is added at a temperature of −70° C. to a solvent that is inert in the reaction, such as tetrahydrofuran, diethyl ether or 1,2-dimethoxyethane, or a mixture of these solvents. A compound represented by formula (C-2) can be manufactured by adding a compound represented by formula (C-1) dropwise to a mixed solution of n-butyl lithium at the same temperature, stirring for 2 hours at this temperature, adding an excess of dry ice, and carrying out a reaction at a temperature between −70° C. and 0° C.

<Step 2>
A compound represented by formula (C-3) can be manufactured according to a method known from literature, for example, a method disclosed in WO 1998/024782 (published on 11 Jun. 1998) by subjecting the compound represented by formula (C-2), which was obtained in <Step 1> in <Manufacturing Method C>, to a sealed tube reaction at a temperature between 0° C. and 150° C. in the presence of a copper catalyst such as copper iodide using 28% aqueous ammonia and, following the reaction, adding concentrated hydrochloric acid to the reaction solution at a temperature below freezing point.

<Step 3>
A compound represented by formula (C-4) can be manufactured according to a method known from literature, for example, a method disclosed in "The Fourth Series of Experimental Chemistry", 22, Organic Synthesis IV, Acids, Amino acids and Peptides, pages 1-82, 1992, Maruzen, by subjecting the compound represented by formula (C-3), which was obtained in <Step 2> in <Manufacturing Method C>, to a reaction in the presence of an acidic reagent such as hydrochloric acid, sulfuric acid, thionyl chloride or acetyl chloride, using ethanol, at a temperature between 0° C. and a temperature at which the solvent refluxes.

In addition, a compound represented by formula (C-4) can be manufactured according to a method known from literature, for example, a method disclosed in "Synthetic Communications", 31(14), pages 2177-2183, 2001, by subjecting the compound represented by formula (C-3), which was obtained in <Step 2> in <Manufacturing Method C>, to a reaction in the presence of ethyl iodide and in the presence of a base such as potassium carbonate, sodium carbonate, potassium hydroxide or sodium hydroxide, using a polar solvent, such as N,N-dimethylformamide or dimethyl sulfoxide, at a temperature between 0° C. and a temperature at which the solvent refluxes.

In addition, a compound represented by formula (C-4) can be manufactured according to a method known from literature, for example, a method disclosed in "The Fourth Series of Experimental Chemistry", 22, Organic Synthesis IV, Acids, Amino acids and Peptides, pages 191-309, 1992, Maruzen, by subjecting the compound represented by formula (C-3), which was obtained in <Step 2> in <Manufacturing Method C>, and ethanol to a reaction in the presence of a condensing agent, such as 1,3-dicyclohexylcarbodiimide (DCC), 1-ethyl-3-(3'-dimethylaminopropyl)carbodiimide hydrochloride (WSC-HCl), 1-hydroxybenzotriazole (Hobt), benzotriazol-1-yloxy-tris(dimethylamino)phosphonium hexafluorophosphate (a BOP reagent), bis(2-oxo-3-oxazolidinyl)phosphinic chloride (BOP-Cl), 2-chloro-1,3-dimethylimidazolinium hexafluorophosphate (CIP), 4-(4,6-dimethoxy-1,3,5-triazin-2-yl)-4-methylmorpholinium chloride (DMTMM), polyphosphoric acid (PPA) or 2-(1H-7-azabenzotriazol-1-yl)-1,1,3,3-tetramethyluronium hexafluorophosphate methanaminium (HATU), in a solvent which does not take part in the reaction, for example a halogen-based solvent such as dichloromethane or chloroform, an ether-based solvent such as diethyl ether or tetrahydrofuran, aromatic hydrocarbon-based solvent such as toluene or benzene, or a polar solvent such as N,N-dimethylformamide, at a temperature between 0° C. and a temperature at which the solvent refluxes, in the presence or absence of a base such as triethylamine or pyridine.

In addition, a compound represented by formula (C-4) can be similarly manufactured according to a method known from literature, for example, a method disclosed in "The Journal of the American Chemical Society", 109(24), pages 7488-7494, 1987, by subjecting the compound represented by formula (C-3) to a reaction in the presence or absence of a base such as triethylamine, N,N-diisopropylethylamine or N,N-dimethylaminopyridine, using a halogenating agent, such as thionyl chloride, oxalyl chloride, phosphoryl chloride, sulfuryl chloride, phosphorus trichloride, phosphorus pentachloride or phosphorus tribromide, and a solvent that is inert in the reaction, such as 1,4-dioxane, tetrahydrofuran, benzene, toluene, dichloromethane, 1,2-dichloroethane or chloroform, or a mixture of these solvents, at a temperature between 0° C. and a temperature at which the solvent refluxes, so as to convert into an acid halide, and then, according to a method known from literature, for example, a method disclosed in "The Fourth Series of Experimental Chemistry", 22, Organic Synthesis IV, Acids, Amino acids and Peptides, pages 144-146, 1992, Maruzen, carrying out a reaction using ethanol in the presence of a base such as triethylamine, N,N-diisopropylethylamine, pyridine or 4-dimethylaminopyridine, using a solvent which does not take part in the reaction, for example, a halogen-based solvent such as dichloromethane, chloroform or 1,2-dichloro ethane, an ether-based solvent such as diethyl ether, tetrahydrofuran or 1,4-dioxane, an aromatic hydrocarbon-based solvent such as toluene or benzene or a polar solvent such as N,N-dimethylformamide, at a temperature between 0° C. and a temperature at which the solvent refluxes.

<Step 4>

Using the compound represented by formula (C-4), which was obtained in <Step 3> in <Manufacturing Method C>, a compound represented by formula (C-5) can be manufactured according to a method known from literature, for example, a method disclosed in "Protective Groups in Organic Synthesis", 4th Edition, 2007 (John Wiley & Sons), Greene et al., by subjecting a variety of reagents (for example, methyl chloroformate or the like in cases where $R^C$ is a methyl group; ethyl chloroformate or the like in cases where $R^C$ is an ethyl group; di-tert-butyl dicarbonate, 2-(2-tert-butoxycarbonyloxyimino)-2-phenylacetonitrile, or the like in cases where $R^C$ is a tert-butyl group; benzyl chloroformate or the like in cases where $R^C$ is a benzyl group) to a reaction using a method that depends on the type of protecting group ($R^C OC(=O)-$).

<Step 5>

A compound represented by formula (C-6) can be manufactured by subjecting the compound represented by formula (C-5), which was obtained in <Step 4> in <Manufacturing Method C>, to a reaction according to <Step 1> in <Manufacturing Method D>, which is described below.

<Step 6>

Using the compound represented by formula (C-6), which was obtained in <Step 5> in <Manufacturing Method C>, a compound represented by formula (C-7) can be manufactured according to a method known from literature, for example, a method disclosed in "Strategic Applications of Named Reactions in Organic Synthesis", Elsevier Academic Press, 2005, pages 116, 117, Curtius Rearrangement, by subjecting diphenylphosphoryl azide (DPPA) to a reaction in the presence of a base such as triethylamine, using a solvent that is inert in the reaction, such as toluene or benzene, or a mixture of these solvents, at a temperature between 0° C. and a temperature at which the solvent refluxes, and then reacting with tert-butyl alcohol.

<Step 7>

Using the compound represented by formula (C-7), which was obtained in <Step 6> in <Manufacturing Method C>, a compound represented by formula (PY-2) can be manufactured according to a method known from literature, for example, a method disclosed in "Protective Groups in Organic Synthesis", 4th Edition, 2007 (John Wiley & Sons), Greene et al., by deprotecting the protecting group ($^tBuOC(=O)-$).

<Manufacturing Method D>

Method for Manufacturing Amide Derivative Represented by Formula (AD-1):

[C131]

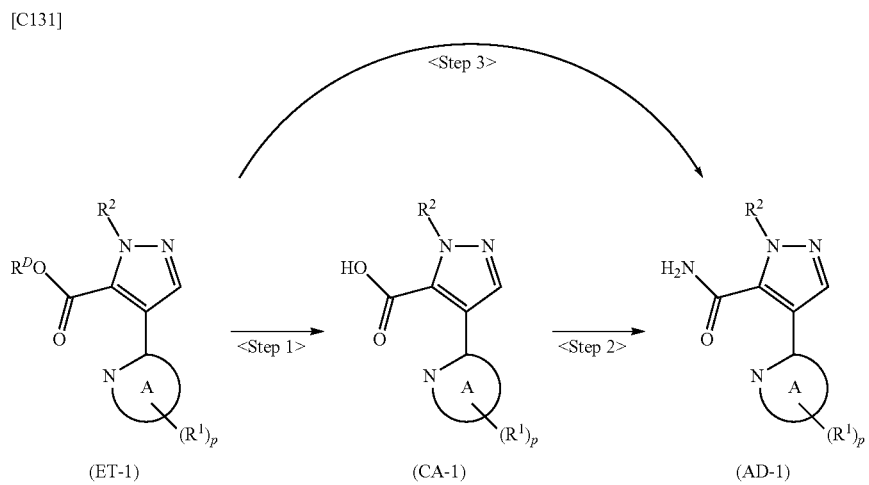

<Step 1>

<$R^D=C_{1-6}$ Alkyl Group (for Example, Methyl Group, Ethyl Group, or the Like)>

A compound represented by formula (CA-1) can be manufactured according to a method known from literature, for example, a method disclosed in "The Fourth Series of Experimental Chemistry", 22, Organic Synthesis IV, Acids, Amino acids and Peptides, pages 1-43, 1992, Maruzen, by subjecting the compound represented by formula (ET-1), which was obtained in <Step 2> in <Manufacturing Method A>, to a reaction in the presence of a base, such as lithium hydroxide, sodium hydroxide, potassium hydroxide, lithium carbonate, sodium carbonate or potassium carbonate, using water and a solvent that is inert in the reaction, such as methanol, ethanol, 2-propanol, N,N-dimethylformamide, 1,4-dioxane or tetrahydrofuran, or a mixture of these solvents, at a temperature between 0° C. and a temperature at which the solvent refluxes.

<$R^D$=tert-butyl Group>

A compound represented by formula (CA-1) can be manufactured using a method known from literature, for example, according to a deprotection method disclosed in "Protective Groups in Organic Synthesis", 4th Edition, 2007 (John Wiley & Sons), Greene et al., by subjecting the compound represented by formula (ET-1), which was obtained in <Step 2> in <Manufacturing Method A>, to a reaction using an acid, such as hydrochloric acid, sulfuric acid, acetic acid or trifluoroacetic acid, at a temperature between 0° C. and a temperature at which the solvent refluxes.

<$R^D$=Benzyl Group>

A compound represented by formula (CA-1) can be manufactured according to a method known from literature, for example, a method disclosed in "The Fourth Series of Experimental Chemistry", 26, Organic Synthesis VIII, Asymmetric Synthesis, Chemical Reduction, Sugar and Labeled Compounds, pages 159-266, 1992, Maruzen", by subjecting the compound represented by formula (ET-1), which was obtained in <Step 2> in <Manufacturing Method A>, to a reaction in the presence of a catalyst, such as palladium-carbon (Pd—C), Raney-nickel (Raney-Ni), platinum oxide ($PtO_2$) or dichlorotri(triphenylphosphine) ruthenium, in a hydrogen gas atmosphere, using a solvent which does not take part in the reaction, for example, an alcoholic solvent such as methanol, ethanol or 2-propanol, an ether-based solvent such as diethyl ether, tetrahydrofuran, 1,2-dimethoxyethane or 1,4-dioxane or a polar solvent such as ethyl acetate or methyl acetate, or a mixture of these solvents, at a temperature between 0° C. and a temperature at which the solvent refluxes.

<Step 2>

Using the compound represented by formula (CA-1), which was obtained in <Step 1> in <Manufacturing Method D>, an active ester is formed according to a method known from literature, for example, a method disclosed in "Synthesis", (12), pages 954, 955, 1979, by subjecting a compound represented by ClCOOR$^A$ or di-tert-butyl dicarbonate ($Boc_2O$) to a reaction in the presence of a base, such as N,N-diisopropylethylamine, triethylamine or pyridine, using a solvent which does not take part in the reaction, such as tetrahydrofuran, diethyl ether or 1,2-dimethoxyethane, or a mixture of these solvents, at a temperature between 0° C. and a temperature at which the solvent refluxes. Without isolating the active ester, a compound represented by formula (AD-1) can then be manufactured according to a method known from literature, for example, a method disclosed in "The Journal of the American Chemical Society", 75, pages 637-640, 1953, by adding a base, such as N,N-diisopropylethylamine, triethylamine or pyridine, and ammonium carbonate to the reaction solution above and carrying out a reaction at a temperature between 0° C. and a temperature at which the solvent refluxes.

<Step 3>

A compound represented by formula (AD-1) can be manufactured according to a method known from literature, for example, a method disclosed in Example 43 on page 120 of WO 2006/043145 (published 27 Apr. 2006), by subjecting the compound represented by formula (ET-1) to a reaction using an aqueous ammonia solution at a temperature between 0° C. and a temperature at which the solvent refluxes.

WORKING EXAMPLES

Working examples and reference examples will now be given in order to explain the present invention in greater detail, but the present invention is not limited to these examples.

Nuclear magnetic resonance (NMR) spectra measurements involved the use of a JEOL JNM-ECX400 FT-NMR (manufactured by JEOL Ltd.) and a (JEOL JNM-ECX300) FT-NMR (manufactured by JEOL Ltd.). LC-Mass measurements were carried out using any of the methods below. A Waters Fraction Lynx MS system (manufactured by Waters) was used, the column was a SunFire column (4.6 mm×5 cm, 5 μm) manufactured by Waters, and the mobile phase was a methanol:0.05% acetic acid aqueous solution at a gradient of 10:90 (0 min)-100:0 (2 min)-100:0 (3 min).

In the physical property data in the working examples, LC-MS means LC-Mass, and in LC-MS measurements, M denotes molecular weight, RT denotes retention time, and $[M+H]^+$, $[M+3H]^{3+}$ and $[M+Na]^+$ denote molecular ion peaks. In $^1$H-NMR data, s denotes singlet, d denotes doublet, t denotes triplet, q denotes quartet and m denotes multiplet in NMR signal patterns.

Working Example 1

Synthesis of 4-(2,5-dimethylpyrimidin-4-yl)-1-methyl-1H-pyrazole-5-carboxylic acid ethyl ester
(Alternative Name: ethyl 4-(2,5-dimethylpyrimidin-4-yl)-1-methyl-1H-pyrazole-5-carboxylate)

[C132]

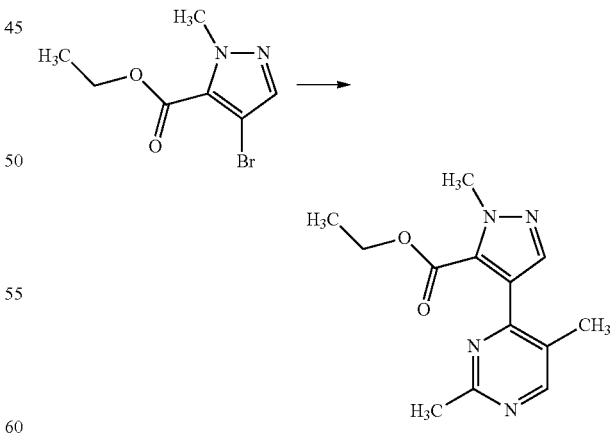

4-bromo-1-methyl-1H-pyrazole-5-carboxylic acid ethyl ester (CAS No.: 1328640-39-6, 5 g, 21 mmol), dipalladium (0) tri(dibenzylideneacetone) ($Pd_2(dba)_3$) (0.39 g, 0.43 mmol), 2-dicyclohexylphosphino-2',6'-dimethoxy-1,1'-biphenyl (0.35 g, 0.86 mmol) and triethylamine (9.0 mL, 64 mmol) were mixed in toluene (25 mL), and 4,4,5,5-tetramethyl-1,3,2-dioxaborolane (3.1 mL, 21 mmol) was added at room temperature. The obtained mixture was stirred for 45 minutes at 90° C., 4,4,5,5-tetramethyl-1,3,2-dioxaborolane (1.5 mL, 10.5 mmol) was added, and a reaction was carried out at the same temperature for 45 minutes. Potassium carbonate (8.9 g, 64 mmol) was dissolved in water (10 mL) and added slowly to the reaction mixture, after which 4-chloro-2,5-dimethylpyrimidine (3.1 g, 21 mmol) and ethanol (20 mL) were added. The obtained mixture was refluxed for 2 hours, cooled to room temperature, filtered with celite, and washed with ethyl acetate and water. The filtrate was extracted with 3N hydrochloric acid. The aqueous layer was washed with methyl tert-butyl ether (MTBE), rendered basic by means of potassium carbonate, and extracted using dichloromethane. The organic layer was concentrated under reduced pressure, and crude 4-(2,5-dimethylpyrimidin-4-yl)-1-methyl-1H-pyrazole-5-carboxylic acid ethyl ester (4.1 g, 52% yield, 71% purity) was obtained as a brown oily substance.

(Physical property data) LC-MS: M=260, RT=0.83 (min), [M+H]$^+$=261. $^1$H-NMR (300 MHz, CDCl$_3$, δ ppm): 8.50 (1H, s), 7.56 (1H, s), 4.22 (3H, s), 4.17 (2H, q, J=7 Hz), 2.72 (3H, s), 2.16 (2H, s), 1.05 (3H, t, J=7 Hz).

Working Example 2

Separate Synthesis of 4-(2,5-dimethylpyrimidin-4-yl)-1-methyl-1H-pyrazole-5-carboxamide

[C133]

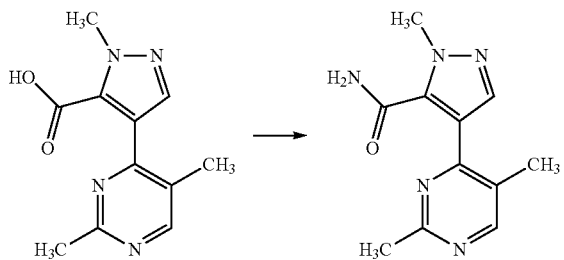

4-(2,5-dimethylpyrimidin-4-yl)-1-methyl-1H-pyrazole-5-carboxylic acid (alternative name: 4-(2,5-dimethylpyrimidin-4-yl)-1-methyl-1H-pyrazole-5-carboxylic acid) (0.5 g, 2.2 mmol), which was synthesized using a method similar to that in <Step 1> in Working Example 5 below, and diisopropylethylamine (0.4 mL, 2.4 mmol) was dissolved in tetrahydrofuran (5 mL), and ethyl chloroformate (0.23 mL, 2.4 mmol) was added dropwise under ice cooling. After stirring for 20 minutes under ice cooling, ammonium carbonate (0.41 g, 4.3 mmol) and diisopropylethylamine (0.75 mL, 4.3 mmol) were added, and the obtained mixture was stirred for 45 minutes at room temperature. A saturated aqueous solution of sodium hydrogen carbonate was added to the reaction mixture, and the reaction mixture was then extracted using ethyl acetate. The organic layer was washed with water, washed with a saturated saline solution, dried using sodium sulfate, and then concentrated under reduced pressure. 4-(2,5-dimethylpyrimidin-4-yl)-1-methyl-1H-pyrazole-5-carboxamide (0.37 g, 73%) was obtained as a white solid. Data for the obtained 4-(2,5-dimethylpyrimidin-4-yl)-1-methyl-1H-pyrazole-5-carboxamide was identical to data for the 4-(2,5-dimethylpyrimidin-4-yl)-1-methyl-1H-pyrazole-5-carboxamide synthesized in <Step 1> in Working Example 6 below.

Working Example 3

Synthesis of 5-fluoro-4-iodopyridine-2-amine

[C134]

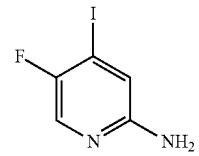

<Step 1> Synthesis of 2,5-difluoro-4-iodopyridine

[C135]

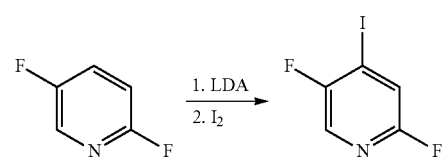

Using 2,5-difluoro-4-pyridine, crude 2,5-difluoro-4-iodopyridine (crude yield 96%) was obtained using a method similar to that disclosed in step (A) in Example 56 on page 116 of WO 2011/073845 (published 23 Jun. 2011). $^1$H NMR data for the obtained 2,5-difluoro-4-iodopyridine was identical to data disclosed in WO 2011/073845.

<Step 2> Synthesis of 5-fluoro-4-iodopyridine-2-amine

[C136]

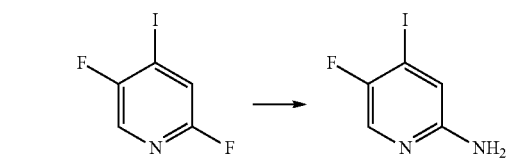

Crude 2,5-difluoro-4-iodopyridine (2.26 g, 9.4 mmol), which was obtained in <Step 1> in Working Example 3, 28% aqueous ammonia (6.8 mL) and 1,4-dioxane (2.3 mL) were added to a sealed reaction vessel and heated for 53 hours using an oil bath at 135° C. Water was added to the reaction mixture, and the reaction mixture was then extracted using methyl tert-butyl ether (MTBE). The obtained organic layer was washed with water and concentrated under reduced pressure. Crude 5-fluoro-4-iodopyridine-2-amine (1.90 g, 85%) was obtained as a moss green-colored solid.

(Physical property data) LC-MS: M=238, RT=0.55 (min), [M+H]$^+$=239. $^1$H NMR (400 MHz, DMSO-d$_6$, δ ppm): 7.82 (1H, s), 6.92 (1H, d, J=4 Hz), 6.00 (2H, s).

Working Example 4

Synthesis of benzyl (4-amino-5-fluoropyridin-2-yl) carbamate hydrochloride

[C137]

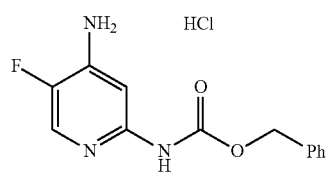

<Step 1> Synthesis of 2-bromo-5-fluoroisonicotinic acid

[C138]

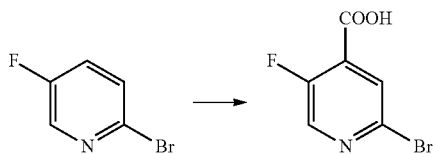

n-butyl lithium (2.6 M hexane solution, 100 mL, 0.26 mol) was added to a tetrahydrofuran solution (630 mL) of diisopropylamine (27 g, 0.26 mol) at a temperature of −60° C. or lower, and the obtained mixture was stirred for 15 minutes at −70° C. A tetrahydrofuran solution (620 mL) of 2-bromo-5-fluoropyridine (42 g, 0.24 mol) was added at a temperature of −60° C. or lower, and the obtained mixture was stirred for 90 minutes at −70° C. An appropriate quantity of dry ice was added at −70° C., after which the temperature of the reaction mixture was allowed to increase to room temperature. The reaction mixture was rendered acidic by adding 2N dilute hydrochloric acid (400 mL), after which tetrahydrofuran was distilled off under reduced pressure. Precipitated crystals were filtered off and washed with water, after which toluene was added, and the obtained mixture was dried by means of azeotropic distillation. 2-bromo-5-fluoroisonicotinic acid (48 g, 92%) was obtained as a white solid.

(Physical property data) LC-MS: M=219, RT=0.74 (min), [M+H]$^+$=220, [M+3H]$^{3+}$=222. $^1$H-NMR (300 MHz, DMSO-d$_6$, δ ppm): 8.63 (1H, d, J=2 Hz), 7.95 (1H, d, J 5 Hz).

<Step 2> Synthesis of 2-amino-5-fluoroisonicotinic acid hydrochloride

[C139]

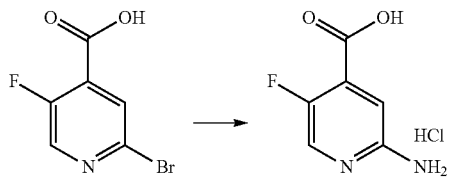

2-bromo-5-fluoroisonicotinic acid (10 g, 45 mmol), which was synthesized using a method similar to that in <Step 1> in Working Example 4, 28% aqueous ammonia (30 mL) and copper iodide (CuI) (0.43 g, 2.3 mmol) were placed in a sealed reaction vessel and heated for 17.5 hours using an oil bath at 120° C. Acetone (30 mL) was added, after which concentrated hydrochloric acid was added under ice cooling so as to obtain a pH of 4. Acetone (60 mL) was again added, and the obtained solid was filtered off, washed with acetone, and dried at 45° C. Crude 2-amino-5-fluoroisonicotinic acid hydrochloride (13 g, 148%, including ammonium salt) was obtained as a beige solid.

(Physical property data) LC-MS: M (free amine)=156, RT=0.17 (min), [M+H]$^+$=157. $^1$H-NMR (400 MHz, DMSO-d$_6$, δ ppm): 8.06 (1H, brs), 6.85 (1H, brs), 6.13 (2H, brs).

<Step 3> Synthesis of 2-amino-5-fluoroisonicotinic acid ethyl ester

[C140]

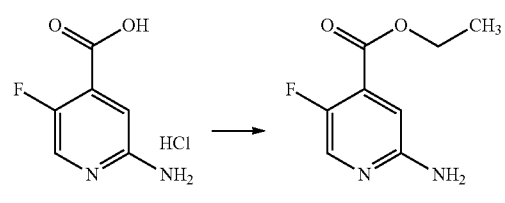

Crude 2-amino-5-fluoroisonicotinic acid hydrochloride (20 g, 104 mmol), which was synthesized using a method similar to that in <Step 2> in Working Example 4, was suspended in ethanol (200 mL), and thionyl chloride (38 mL, 520 mmol and N,N-dimethylformamide (DMF, 0.8 mL, 10 mmol) were added under ice cooling. The obtained mixture was heated for 5.75 hours at 80° C. After cooling the mixture, methyl tert-butyl ether (MTBE) (400 mL) was added, and a precipitated solid was filtered off and washed with methyl tert-butyl ether (MTBE). The obtained solid was dissolved in ethyl acetate and washed with a saturated aqueous solution of sodium hydrogen carbonate. The aqueous layer was extracted using ethyl acetate, and the obtained organic layer was combined with the organic layer mentioned above and washed with dilute aqueous ammonia, water and a saturated saline solution in that order. The organic layer was dried using sodium sulfate and concentrated under reduced pressure. The obtained solid was suspended in heptadecane, filtered off and dried. 2-amino-5-fluoroisonicotinic acid ethyl ester (19 g, 98%) was obtained as a beige solid.

(Physical property data) LC-MS: M=184, RT=0.68 (min), [M+H]$^+$=185. $^1$H-NMR (300 MHz, DMSO-d$_6$, δ ppm): 8.01 (1H, d, J=3 Hz), 6.82 (1H, d, J=6 Hz), 6.18 (2H, s), 4.31 (2H, q, J=7 Hz), 1.29 (3H, t, J=7 Hz).

\<Step 4\> Synthesis of 2-(((benzyloxy)carbonyl)amino)-5-fluoroisonicotinic acid ethyl ester

[C141]

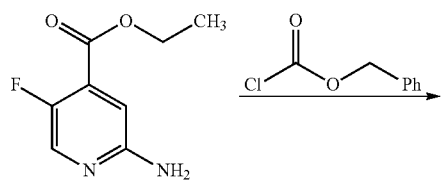

Benzyl chlorocarbonate (5.0 mL, 35 mmol) was added under ice cooling to a pyridine solution (40 mL) of 2-amino-5-fluoroisonicotinic acid ethyl ester (5.0 g, 27 mmol), which was synthesized in \<Step 3\> in Working Example 4. The obtained mixture was stirred for 4 hours at 25° C., after which benzyl chlorocarbonate (3.1 mL) was added. Water was added to the reaction mixture, and a precipitated solid was filtered off and washed with water. The obtained solid was suspended in a mixed solvent (1:1) of methyl tert-butyl ether (MTBE) and heptane, filtered off and dried. 2-(((benzyloxy)carbonyl)amino)-5-fluoroisonicotinic acid ethyl ester (7.6 g, 88%) was obtained as a white solid.

(Physical property data) LC-MS: M=318, RT=1.12 (min), [M+Na]$^+$=341. $^1$H-NMR (300 MHz, DMSO-$d_6$, δ ppm): 10.6 (1H, s), 8.46 (1H, d, J=3 Hz), 8.26 (1H, d, J=6 Hz), 7.45-7.31 (5H, m), 5.19 (2H, s), 4.36 (2H, q, J=7 Hz), 1.32 (3H, t, J=7 Hz).

\<Step 5\> Synthesis of 2-(((benzyloxy)carbonyl)amino)-5-fluoroisonicotinic acid

[C142]

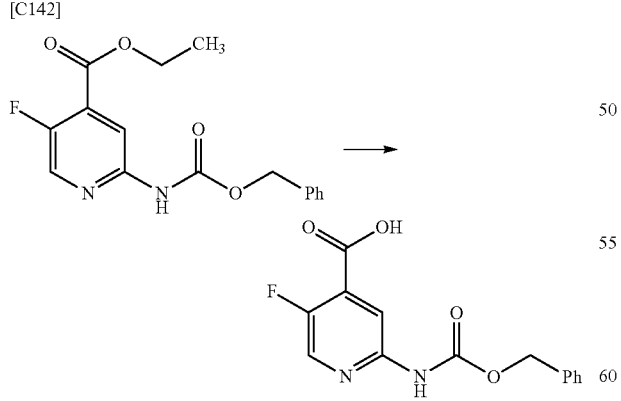

A 1N aqueous solution of sodium hydroxide (26 mL) was added under ice cooling to an ethanol suspension of 2-(((benzyloxy)carbonyl)amino)-5-fluoroisonicotinic acid ethyl ester (7.5 g, 23 mmol), which was synthesized in \<Step 4\> in Working Example 4. The obtained suspension was stirred for 4 hours at room temperature. Water was added, after which the pH was adjusted to 4 to 5 by means of concentrated hydrochloric acid. The obtained solid was filtered off, washed with water and dried. 2-(((benzyloxy)carbonyl)amino)-5-fluoroisonicotinic acid (6.4 g, 93%) was obtained as a white solid.

(Physical property data) LC-MS: M=290, RT=0.98 (min), [M+H]$^+$=291, [M+Na]$^+$=313. $^1$H-NMR (400 MHz, DMSO-$d_6$, δ ppm): 10.6 (1H, s), 8.42 (1H, d, J=4 Hz), 8.24 (1H, d, J=8 Hz), 7.44-7.31 (5H, m), 5.19 (2H, s).

\<Step 6\> Synthesis of benzyl tert-butyl(5-fluoropyridin-2, 4-diyl)dicarbamate

[C143]

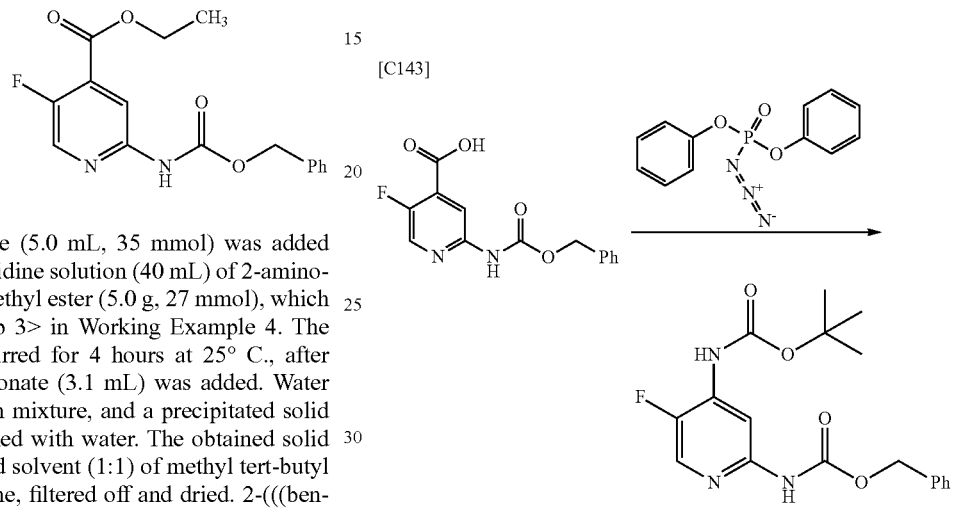

2-(((benzyloxy)carbonyl)amino)-5-fluoroisonicotinic acid (0.19 g, 0.65 mmol), which was synthesized in \<Step 5\> in Working Example 4, was suspended in tert-butanol (2.85 mL), and triethylamine (0.27 mL, 2.0 mmol) was then added. The obtained mixture was heated, and diphenylphosphoryl azide (0.16 mL, 0.72 mmol) was added dropwise at 80° C. After heating for 4 hours at 80° C., diphenylphosphoryl azide (0.03 mL) was added. Heptane (2 mL) was added, and the obtained solid was filtered off, washed with heptane and then dried. Benzyl tert-butyl(5-fluoropyridin-2,4-diyl)dicarbamate (0.21 g, 87%) was obtained as a white solid.

(Physical property data) LC-MS: M=361, RT=1.1 (min), [M+Na]$^+$=384. $^1$H-NMR (400 MHz, DMSO-$d_6$, δ ppm): 10.2 (1H, s), 9.57 (1H, s), 8.49 (1H, d, J=8 Hz), 8.11 (1H, d, J=3 Hz), 7.43-7.31 (5H, m), 5.16 (2H, s), 1.49 (9H, s).

\<Step 7\> Synthesis of benzyl (4-amino-5-fluoropyridin-2-yl) carbamate hydrochloride

[C144]

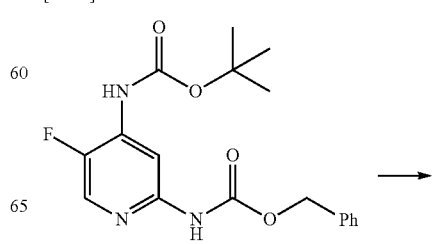

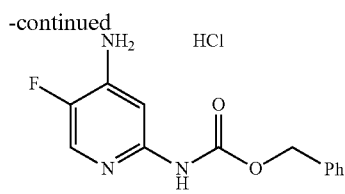

Benzyl tert-butyl(5-fluoropyridin-2,4-diyl)dicarbamate (0.19 g, 0.53 mmol), which was synthesized in <Step 6> in Working Example 4, was suspended in 1,4-dioxane (1.9 mL), and a 4N hydrochloric acid solution (1,4-dioxane solution: 0.39 mL) was added. The obtained mixture was stirred at room temperature and then stirred for 3.5 hours at 60° C., and a 4N hydrochloric acid solution (1,4-dioxane solution: 0.39 mL) was then added. Methyl tert-butyl ether (MTBE) (5 mL) was added, the obtained solid was filtered off, washed with methyl tert-butyl ether (MTBE) and dried, and benzyl (4-amino-5-fluoropyridin-2-yl)carbamate hydrochloride (0.15 g, 93%) was obtained as a white solid.

(Physical property data) LC-MS: M=261, RT=0.76 (min), [M+Na]$^+$=284. $^1$H-NMR (400 MHz, DMSO-d$_6$, δ ppm): 11.4 (1H, s), 8.10 (1H, d, J=4 Hz), 8.07 (2H, brs), 7.46-7.35 (5H, m), 6.79 (1H, d, J=8 Hz), 5.24 (2H, s).

Working Example 5

Synthesis of N-(2-amino-5-fluoropyridin-4-yl)-4-(2,5-dimethylpyrimidin-4-yl)-1-methyl-1H-pyrazole-5-carboxamide

[C145]

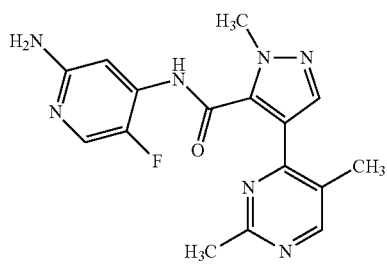

<Step 1> Synthesis of 4-(2,5-dimethylpyrimidin-4-yl)-1-methyl-1H-pyrazole-5-carboxylic acid (Alternative Name: 4-(2,5-dimethylpyrimidin-4-yl)-1-methyl-1H-pyrazole-5-carboxylic acid)

[C146]

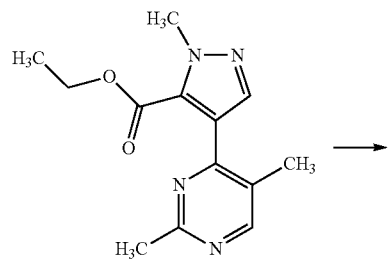

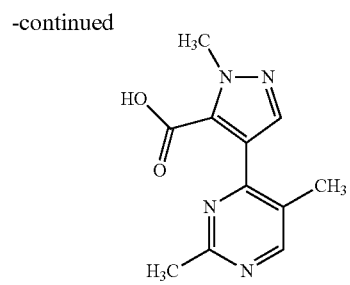

A 1N aqueous solution of sodium hydroxide (19 mL, 19 mmol) and toluene (20 mL) were added to crude 4-(2,5-dimethylpyrimidin-4-yl)-1-methyl-1H-pyrazole-5-carboxylic acid ethyl ester (4.0 g, 16 mmol), which was synthesized in Working Example 1, and the obtained mixture was stirred for 5 hours at room temperature. The aqueous layer was separated and adjusted to a pH of 1 by adding concentrated hydrochloric acid. A precipitated solid was filtered off, washed with water and dried, and 4-(2,5-dimethylpyrimidin-4-yl)-1-methyl-1H-pyrazole-5-carboxylic acid (2.4 g, 65%) was obtained as a pale yellow solid.

(Physical property data) LC-MS: M=232, RT=0.65 (min), [M+H]$^+$=233. $^1$H-NMR (400 MHz, DMSO-d$_6$, δ ppm): 8.49 (1H, s), 7.61 (1H, s), 4.07 (3H, s), 2.55 (3H, s), 2.15 (3H, s).

<Step 2> Synthesis of benzyl (4-(4-(2,5-dimethylpyrimidin-4-yl)-1-methyl-1H-pyrazole-5-carboxamide)-5-fluoropyridin-2-yl)carbamate

[C147]

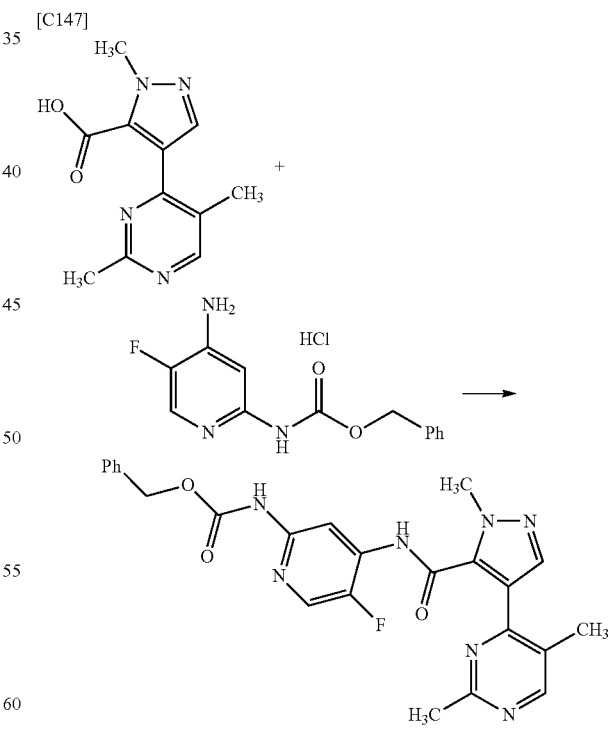

Benzyl (4-amino-5-fluoropyridin-2-yl)carbamate hydrochloride (50 mg, 0.17 mmol), which was synthesized using a method similar to that in Working Example 4, was dissolved in N-methylpyrrolidone (NMP) (0.4 mL) and 2,6-lutidine (0.06 mL), and 4-(2,5-dimethylpyrimidin-4-yl)-1- methyl-1H-pyrazole-5-carboxylic acid (47 mg, 0.2 mmol), which was synthesized using a method similar to that in <Step 1> in Working Example 5, and O-(7-aza-1H-benzotriazol-1-yl)-N,N,N',N'-tetramethyl uronium hexafluorophosphate (HATU, CAS No.: 148893-10-1) (89 mg, 0.24 mmol) were added. The obtained mixture was stirred for 54 hours at 60° C., and lutidine 2,6-lutidine (0.11 mL) and HATU (0.18 g) were then added. Water (1 mL) was added, and the obtained mixture was stirred for 2 hours at room temperature. The obtained solid was filtered off, washed with water, suspended again in ethanol, filtered off, washed with ethanol and dried, and benzyl (4-(4-(2,5-dimethylpyrimidin-4-yl)-1-methyl-1H-pyrazole-5-carboxamide)-5-fluoropyridin-2-yl)carbamate (64 mg, 80%) was obtained as a beige solid.

(Physical property data) LC-MS: M=475, RT=1.1 (min), [M+H]$^+$=476, [M+Na]$^+$=498. $^1$H-NMR (400 MHz, DMSO-d$_6$, δ ppm): 10.9 (1H, s), 10.3 (1H, s), 8.67 (1H, brs), 8.55 (1H, s), 8.25 (1H, d, J=4 Hz), 8.00 (1H, s), 7.43-7.31 (5H, m), 5.17 (2H, s), 4.01 (3H, s), 2.38 (3H, s), 2.37 (3H, s).

<Step 3> Synthesis of N-(2-amino-5-fluoropyridin-4-yl)-4-(2,5-dimethylpyrimidin-4-yl)-1-methyl-1H-pyrazole-5-carboxamide

[C148]

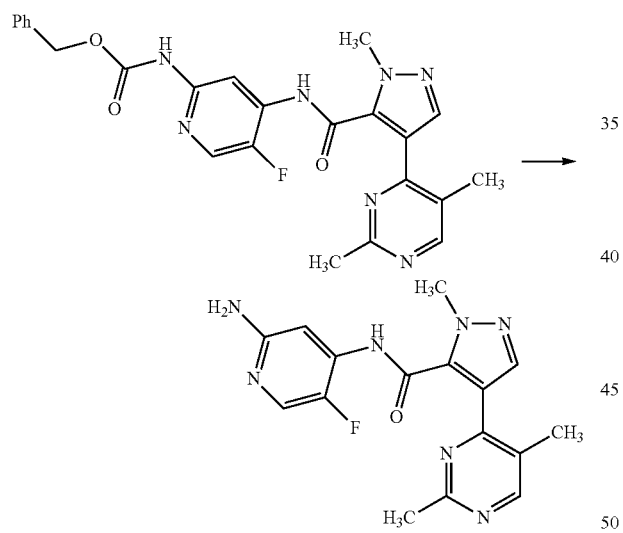

Benzyl (4-(4-(2,5-dimethylpyrimidin-4-yl)-1-methyl-1H-pyrazole-5-carboxamide)-5-fluoropyridin-2-yl)carbamate (50 mg, 0.11 mmol), Which was synthesized using a method similar to that in <Step 2> in Working Example 5, was dissolved in dichloromethane (0.75 mL) and methanol (0.25 mL), palladium-carbon (5 mg) was added, and the obtained mixture was stirred for 6.5 hours at room temperature in a hydrogen gas atmosphere. The palladium-carbon was removed by filtration, the obtained liquid was concentrated under reduced pressure, and N-(2-amino-5-fluoropyridin-4-yl)-4-(2,5-dimethylpyrimidin-4-yl)-1-methyl-1H-pyrazole-5-carboxamide (33 mg, 92%) was obtained as a pale yellow solid.

(Physical property data) LC-MS: M=341, RT=0.67 (min), [M+H]$^+$=342. $^1$H-NMR (400 MHz, DMSO-d$_6$, δ ppm): 10.7 (1H, s), 8.56 (1H, s), 7.98 (1H, s), 7.84 (1H, d, J=3 Hz), 7.29 (1H, brs), 5.95 (2H, s), 4.00 (3H, s), 2.43 (3H, s), 2.36 (3H, s).

Working Example 6

Synthesis of 4-(2,5-dimethylpyrimidin-4-yl)-N-(6-fluoro-2-phenyl-[1,2,4]triazolo[1,5-a]pyridin-7-yl)-1-methyl-1H-pyrazole-5-carboxamide

[C149]

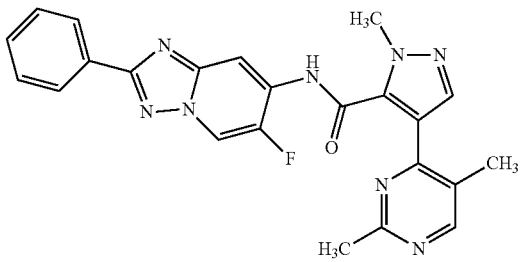

<Step 1> Synthesis of 4-(2,5-dimethylpyrimidin-4-yl)-1-methyl-1H-pyrazole-5-carboxamide

[C150]

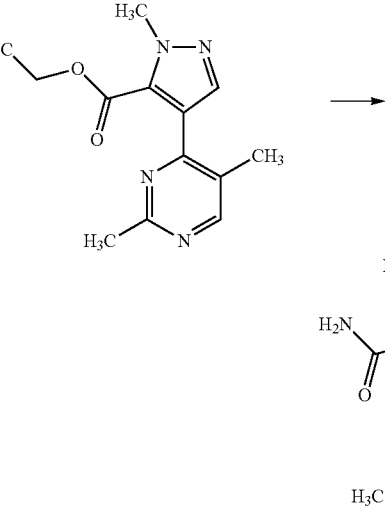

A mixture of crude 4-(2,5-dimethylpyrimidin-4-yl)-1-methyl-1H-pyrazole-5-carboxylic acid ethyl ester (0.50 g, 1.9 mmol), which was synthesized using a method similar to that in Working Example 1, and 25% aqueous ammonia (5 mL) was stirred for 20 hours at room temperature. A saturated aqueous solution of sodium hydrogen carbonate was added to the reaction mixture, and the reaction mixture was then extracted using ethyl acetate. The obtained organic layer was washed with a saturated saline solution, dried using sodium sulfate, and then concentrated under reduced pressure. 4-(2,5-dimethylpyrimidin-4-yl)-1-methyl-1H-pyrazole-5-carboxamide (0.13 g, 30%) was obtained as a pale yellow solid.

(Physical property data) LC-MS: M=231, RT=0.54 (min), [M+H]$^+$=232. $^1$H-NMR (300 MHz, DMSO-d$_6$, δ ppm): 8.57

(1H, s), 8.28 (1H, brs), 7.84 (1H, s), 7.79 (1H, brs), 3.98 (3H, s), 2.56 (3H, s), 2.30 (2H, s).

<Step 2> Synthesis of N-(2-amino-5-fluoropyridin-4-yl)-4-(2,5-dimethylpyrimidin-4-yl)-1-methyl-1H-pyrazole-5-carboxamide

[C151]

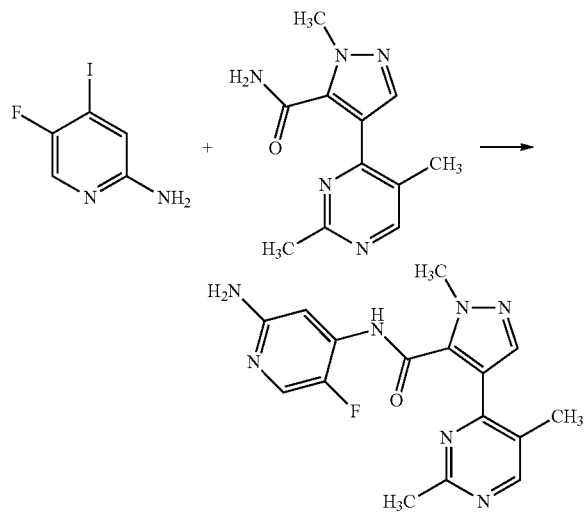

Crude 5-fluoro-4-iodopyridine-2-amine (104 mg, 0.44 mmol), which was synthesized in Working Example 3, 4-(2,5-dimethylpyrimidin-4-yl)-1-methyl-1H-pyrazole-5-carboxamide (92 mg, 0.4 mmol), which was synthesized in Working Example 2, N,N'-dimethyl-1,2-ethanediamine (4.1 mg, 0.05 mmol), copper iodide (CuI) (9.1 mg, 0.05 mmol) and potassium carbonate (110 mg, 0.8 mmol) were mixed in 1,4-dioxane (1 mL), and heated for 20 hours using an oil bath at 100° C. Crude 5-fluoro-4-iodopyridine-2-amine (16 mg, 0.07 mmol), N,N'-dimethyl-1,2-ethanediamine (2 mg, 0.02 mmol) and copper iodide (CuI) (4 mg, 0.02 mmol) were added, the obtained mixture was heated for 6 hours using an oil bath at 100° C., after which crude 5-fluoro-4-iodopyridine-2-amine (16 mg, 0.07 mmol) was added, and the obtained mixture was heated and stirred for 15 hours. Water and dichloromethane were added to the reaction mixture, insoluble substances were removed by filtration, and the organic layer was then separated. The obtained organic layer was washed with water and concentrated under reduced pressure. The obtained solid was washed with methyl tert-butyl ether (MTBE) in order to remove excess 5-fluoro-4-iodopyridine-2-amine, and N-(2-amino-5-fluoropyridin-4-yl)-4-(2,5-dimethylpyrimidin-4-yl)-1-methyl-1H-pyrazole-5-carboxamide (82 mg, 60%) was obtained as a brown solid. Data for the obtained N-(2-amino-5-fluoropyridin-4-yl)-4-(2,5-dimethylpyrimidin-4-yl)-1-methyl-1H-pyrazole-5-carboxamide was identical to the data for the N-(2-amino-5-fluoropyridin-4-yl)-4-(2,5-dimethylpyrimidin-4-yl)-1-methyl-1H-pyrazole-5-carboxamide synthesized in <Step 3> in Working Example 5.

<Step 3> Synthesis of N-(2-benzimidamido-5-fluoropyridin-4-yl)-4-(2,5-dimethylpyrimidin-4-yl)-1-methyl-1H-pyrazole-5-carboxamide

[C152]

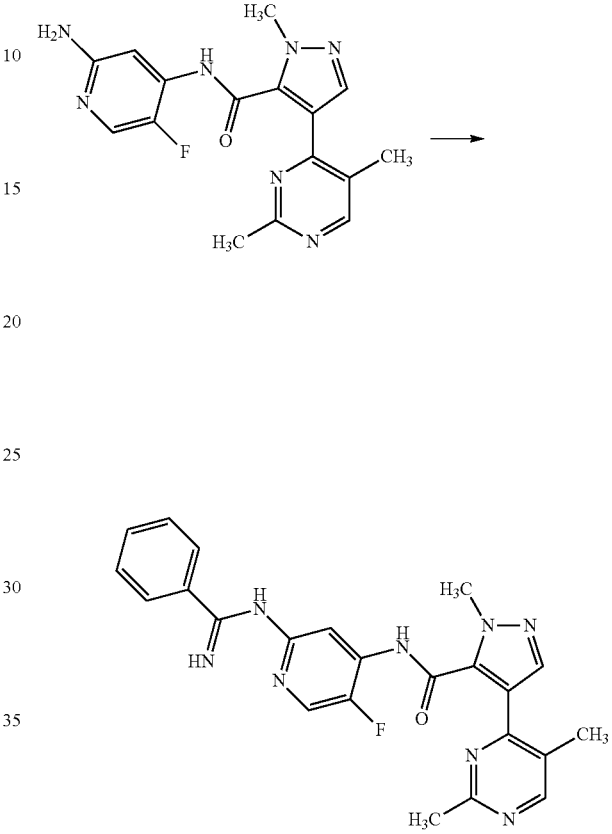

Pyridine (0.5 mL) and dimethyl sulfoxide (0.25 mL) were added to a mixture of N-(2-amino-5-fluoropyridin-4-yl)-4-(2,5-dimethylpyrimidin-4-yl)-1-methyl-1H-pyrazole-5-carboxamide (100 mg, 0.29 mmol), which was synthesized using a method similar to that in <Step 3> in Working Example 5 or <Step 2> in Working Example 6, and methylbenzimidothioate hydroiodide (106 mg, 0.38 mmol). The obtained solution was stirred for 7 hours in an oil bath at 80° C. Acetone (0.5 mL), a saturated aqueous solution of sodium hydrogen carbonate (0.5 mL) and water (2 mL) were added to the reaction mixture and stirred for 1 hour at room temperature. The obtained solid was filtered off, washed with water and dried, and N-(2-benzimidamido-5-fluoropyridin-4-yl)-4-(2,5-dimethylpyrimidin-4-yl)-1-methyl-1H-pyrazole-5-carboxamide (112 mg, 86%) was obtained as a white-yellow solid.

(Physical property data) LC-MS: M=444, RT=0.81 (min), [M+H]$^+$=445. $^1$H-NMR (400 MHz, DMSO-d$_5$, δ ppm): 10.9 (1H, s), 9.86 (1H, brs), 8.57 (1H, s), 8.31 (1H, d, J=2 Hz), 8.03-8.01 (3H, m), 7.92 (1H, brs), 7.67-7.47 (3H, m), 4.02 (3H, s), 2.41 (3H, s), 2.37 (3H, s).

\<Step 4\> Synthesis of 4-(2,5-dimethylpyrimidin-4-yl)-N-(6-fluoro-2-phenyl-[1,2,4]triazolo[1,5-a]pyridin-7-yl)-1-methyl-1H-pyrazole-5-carboxamide

[C153]

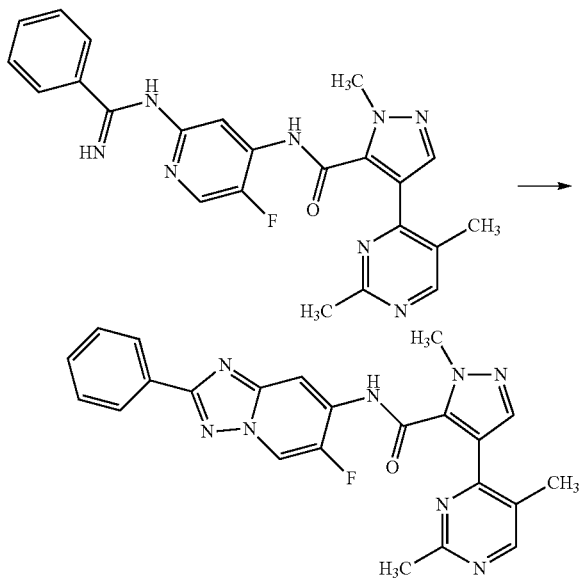

N-(2-benzimidamido-5-fluoropyridin-4-yl)-4-(2,5-dimethylpyrimidin-4-yl)-1-methyl-1H-pyrazole-5-carboxamide (200 mg, 0.45 mmol), which was synthesized using a method similar to that in \<Step 3\> in Working Example 6, and a copper chloride (CuCl) catalyst (4.5 mg, 0.04 mmol) were mixed in pyridine (0.8 mL), and the obtained mixture was stirred in air for 2.5 hours using an oil bath at 100° C. 28% aqueous ammonia (0.2 mL) and water were added, and the obtained suspension was stirred for 10 minutes under ice cooling. The generated solid was filtered off, washed with water and dried, and 4-(2,5-dimethylpyrimidin-4-yl)-N-(6-fluoro-2-phenyl-[1,2,4]triazolo[1,5-a]pyridin-7-yl)-1-methyl-1H-pyrazole-5-carboxamide (159 mg, 80%) was obtained as an off-white solid.

(Physical property data) LC-MS: M=442, RT=1.13 (min), [M+H]$^+$=443. $^1$H-NMR (400 MHz, CDCl$_3$, δ ppm): 11.72 (1H, s), 8.78 (1H, d, J=8 Hz), 8.63 (1H, s), 8.59 (1H, d, J=8 Hz), 8.27-8.24 (2H, m), 7.70 (1H, s), 7.51-7.49 (3H, m), 4.31 (3H, s), 2.78 (3H, s), 2.42 (3H, s).

Working Example 7

Synthesis of methyl 1-methyl-4-(2-methylpyrimidin-4-yl)-1H-pyrazole-5-carboxylate

[C154]

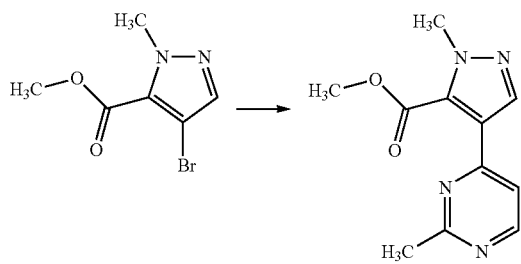

Using 4-bromo-1-methyl-1H-pyrazole-5-carboxylic acid methyl ester (CAS No.: 514816-42-3, 2.0 g, 9.1 mmol) and 4-chloro-2-methylpyrimidine (0.94 g), methyl 1-methyl-4-(2-methylpyrimidin-4-yl)-1H-pyrazole-5-carboxylate (1.26 g) was obtained as a yellow oily substance using a method similar to that in \<Step 1\> in Working Example 1 or a method based on this method.

(Physical property data) LC-MS: M=232, RT=0.75 (min), [M+H]$^+$=233. $^1$H-NMR (300 MHz, CDCl$_3$, δ ppm): 8.62 (1H, d, J=5 Hz), 7.85 (1H, s), 7.29 (1H, d, J=5 Hz), 4.15 (3H, s), 3.87 (3H, s), 2.74 (3H, s).

Working Example 8

Synthesis of 1-methyl-4-(2-methylpyrimidin-4-yl)-1H-pyrazole-5-carboxylic acid

[C155]

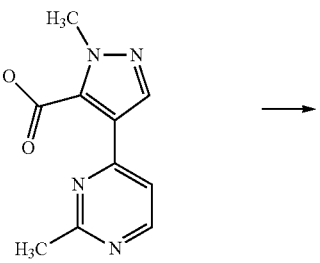

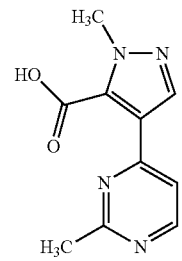

Using methyl 1-methyl-4-(2-methylpyrimidin-4-yl)-1H-pyrazole-5-carboxylate (1.26 g), which was obtained in Working Example 7, the title compound (682 mg) was obtained as a colorless solid using a method similar to that in \<Step 1\> in Working Example 5 or a method based on this method.

(Physical property data) LC-MS: M=218, RT=0.67 (min), [M+H]$^+$=219. $^1$H-NMR (300 MHz, CDCl$_3$, δ ppm): 8.79 (1H, d, J=6 Hz), 8.09 (1H, s), 7.56 (1H, d, J=6 Hz), 4.36 (3H, s), 2.81 (3H, s).

Working Example 9

Synthesis of 1-methyl-4-(2-methylpyrimidin-4-yl)-1H-pyrazole-5-carboxamide

[C156]

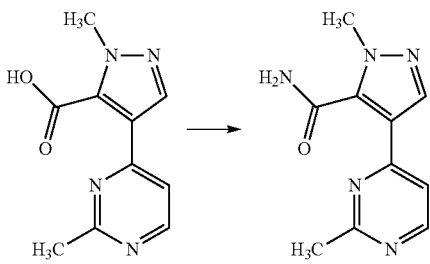

1-methyl-4-(2-methylpyrimidin-4-yl)-1H-pyrazole-5-carboxylic acid (2.0 g, 9.2 mmol), which was synthesized using a method similar to that in Working Example 8, and diisopropylethylamine (1.8 mL, 10 mmol) were suspended in tetrahydrofuran (20 mL), and benzyl chloroformate (1.7 mL, 10 mmol) was added dropwise under ice cooling. After stirring for 30 minutes under ice cooling, ammonium carbonate (1.8 g, 18 mmol) and diisopropylethylamine (3.2 mL, 18 mmol) were added, and the obtained mixture was stirred for 1.25 hours at room temperature. An aqueous solution of sodium hydrogen carbonate was added to the reaction mixture, and the reaction mixture was extracted using ethyl acetate. The solid in the aqueous layer was filtered off, and the obtained aqueous layer was extracted using ethyl acetate. The organic layer was added, washed with water, washed with a saturated saline solution, dried using sodium sulfate, and then concentrated under reduced pressure. The obtained solid residue and the solid obtained from the aqueous layer were combined, the obtained mixture was triturated with methyl tert-butyl ether (MTBE), filtered off, washed with MTBE and dried, and 1-methyl-4-(2-methylpyrimidin-4-yl)-1H-pyrazole-5-carboxamide (1.2 g, 59%) was obtained as a white solid.

(Physical property data) LC-MS: M=217, RT=0.57 (min), [M+H]$^+$=218. $^1$H-NMR (400 MHz, DMSO-d$_6$, δ ppm): 9.17 (1H, s), 8.66 (1H, d, J=6 Hz), 8.12 (1H, s), 8.03 (1H, s), 7.54 (1H, d, J=6 Hz), 3.96 (3H, s), 2.60 (3H, s).

Working Example 10

Synthesis of N-(6-fluoro-2-phenyl-[1,2,4]triazolo[1,5-a]pyridin-7-yl)-1-methyl-4-(2-methylpyrimidin-4-yl)-1H-pyrazole-5-carboxamide

[C157]

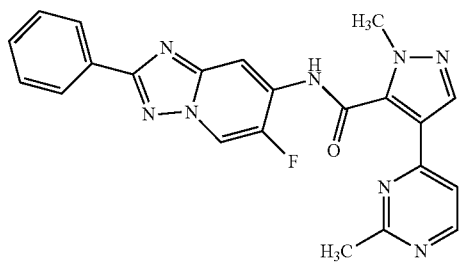

<Step 1> Synthesis of N-(2-amino-5-fluoropyridin-4-yl)-1-methyl-4-(2-methylpyrimidin-4-yl)-1H-pyrazole-5-carboxamide

[C158]

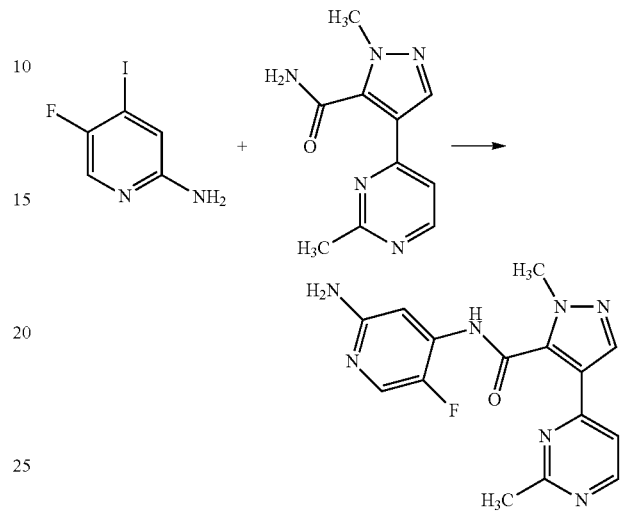

5-fluoro-4-iodopyridine-2-amine (482 mg, 2.0 mmol), which was synthesized using a method similar to that in Working Example 3, and 1-methyl-4-(2-methylpyrimidin-4-yl)-1H-pyrazole-5-carboxamide (400 mg, 1.8 mmol), which was synthesized in Working Example 9, were subjected to a reaction using a method based on <Step 2> in Working Example 6, after which a 28% aqueous solution of ammonia (0.8 mL) was added, and the obtained mixture was stirred at room temperature, and then diluted with water. The precipitated solid was filtered off, washed with water and dried, the obtained crude product was triturated in ethyl acetate/ethanol/MTBE (1:2:10), and N-(2-amino-5-fluoropyridin-4-yl)-1-methyl-4-(2-methylpyrimidin-4-yl)-1H-pyrazole-5-carboxamide (299 mg, 50%) was obtained as a white solid.

(Physical property data) LC-MS: M=327, RT=0.69 (min), [M+H]$^+$=328. $^1$H-NMR (400 MHz, DMSO-d$_6$, δ ppm): 11.6 (1H, s), 8.68 (1H, d, J=5 Hz), 8.22 (1H, s), 7.87 (1H, d, J=2 Hz), 7.66 (1H, d, J=5 Hz), 7.30 (1H, s), 5.90 (2H, s), 4.00 (3H, s), 2.49 (3H, s).

<Step 2> Synthesis of N-(2-benzimidamido-5-fluoropyridin-4-yl)-1-methyl-4-(2-methylpyrimidin-4-yl)-1H-pyrazole-5-carboxamide

[C159]

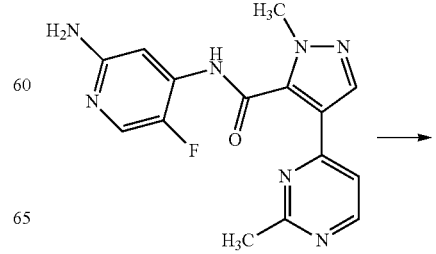

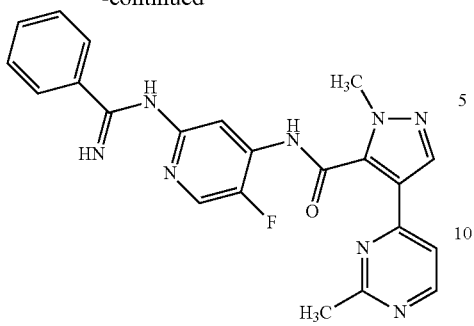

Using N-(2-amino-5-fluoropyridin-4-yl)-1-methyl-4-(2-methylpyrimidin-4-yl)-1H-pyrazole-5-carboxamide (290 mg, 0.89 mmol), which was synthesized using a method similar to that in <Step 1> in Working Example 10, and methylbenzimidothioate hydroiodide (322 mg, 1.2 mmol; 74 mg, 0.27 mmol; or 49 mg, 0.18 mmol), N-(2-benzimidamido-5-fluoropyridin-4-yl)-1-methyl-4-(2-methylpyrimidin-4-yl)-1H-pyrazole-5-carboxamide (368 mg, 97%) was obtained as a gray solid using a method similar to that in <Step 3> in Working Example 6.

(Physical property data) LC-MS: M=430, RT=0.84 (min), [M+H]⁺=431. ¹H-NMR (400 MHz, DMSO-d₆, δ ppm): 11.8 (1H, s), 9.80 (1H, s), 8.70 (1H, d, J=6 Hz), 8.35 (1H, d, J=1 Hz), 8.27 (1H, s), 8.04 (2H, d, J=7 Hz), 7.91 (1H, d, J=5 Hz), 7.68 (1H, d, J=5 Hz), 7.53-7.46 (3H, m), 4.03 (3H, s), 2.49 (3H, s).

<Step 3> Synthesis of N-(6-fluoro-2-phenyl-[1,2,4]triazolo[1,5-a]pyridin-7-yl)-1-methyl-4-(2-methylpyrimidin-4-yl)-1H-pyrazole-5-carboxamide

[C160]

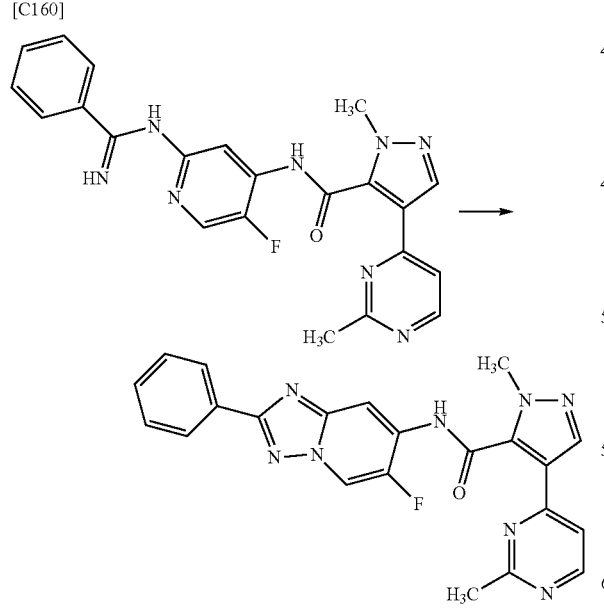

Using N-(2-benzimidamido-5-fluoropyridin-4-yl)-1-methyl-4-(2-methylpyrimidin-4-yl)-1H-pyrazole-5-carboxamide (320 mg, 0.74 mmol), which was synthesized in <Step 2> in Working Example 10, N-(6-fluoro-2-phenyl-[1,2,4]triazolo[1,5-a]pyridin-7-yl)-1-methyl-4-(2-methylpyrimidin-4-yl)-1H-pyrazole-5-carboxamide (263 mg, 83%) was obtained as a beige solid using a method similar to that in <Step 4> in Working Example 6.

(Physical property data) LC-MS: M=428, RT=1.16 (min), [M+H]⁺=429. ¹H-NMR (400 MHz, CDCl₃, δ ppm): 13.39 (1H, s), 8.75-8.64 (3H, m), 8.28-8.26 (2H, m), 7.96 (1H, s), 7.52-7.47 (4H, m), 4.36 (3H, s), 2.79 (3H, s).

Working Example 11

Synthesis of methyl 4-(5-fluoro-2-methoxypyrimidin-4-yl)-1-methyl-1H-pyrazole-5-carboxylate

[C161]

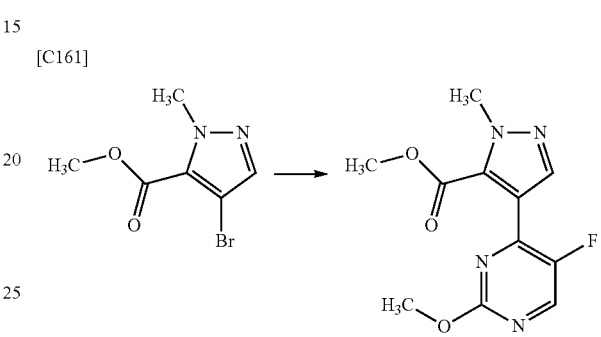

Using 4-bromo-1-methyl-1H-pyrazole-5-carboxylic acid methyl ester (CAS No.: 514816-42-3, 2.52 g, 11.5 mmol) and 4-chloro-5-fluoro-2-methoxypyrimidine (1.5 g), methyl 4-(5-fluoro-2-methoxypyrimidin-4-yl)-1-methyl-1H-pyrazole-5-carboxylate (1.6 g) was obtained as a pale yellow liquid using a method similar to that in <Step 1> in Working Example 1 or a method based on this method.

(Physical property data) LC-MS: M=266, RT=0.91 (min), [M+H]⁺=267. ¹H-NMR (300 MHz, CDCl₃, δ ppm): 8.35 (1H, d, J=2 Hz), 7.86 (1H, d, J=1 Hz), 4.15 (3H, s), 4.00 (3H, s), 3.86 (3H, s).

Working Example 12

Synthesis of 4-(5-fluoro-2-methoxypyrimidin-4-yl)-1-methyl-1H-pyrazole-5-carboxylic acid

[C162]

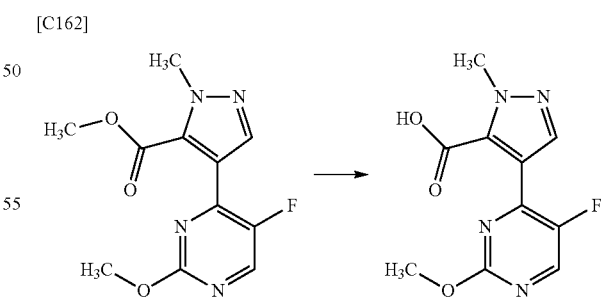

Using methyl 4-(5-fluoro-2-methoxypyrimidin-4-yl)-1-methyl-1H-pyrazole-5-carboxylate (1.6 g), which was obtained in Working Example 11, 4-(5-fluoro-2-methoxypyrimidin-4-yl)-1-methyl-1H-pyrazole-5-carboxylic acid (0.65 g) was obtained as a colorless solid using a method similar to that in <Step 1> in Working Example 5 or a method based on this method.

Working Example 13

Synthesis of 4-(5-fluoro-2-methoxypyrimidin-4-yl)-1-methyl-1H-pyrazole-5-carboxamide

[C163]

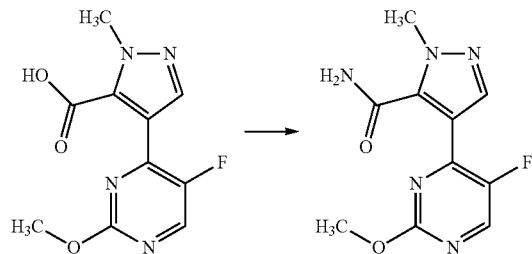

Using 4-(5-fluoro-2-methoxypyrimidin-4-yl)-1-methyl-1H-pyrazole-5-carboxylic acid (0.50 g, 2.0 mmol), which was synthesized using a method similar to that in Working Example 12, and ethyl chloroformate (0.21 mL, 2.2 mmol), 4-(5-fluoro-2-methoxypyrimidin-4-yl)-1-methyl-1H-pyrazole-5-carboxamide (0.40 g, 80%) was obtained as a white solid using a method similar to that in Working Example 9.

(Physical property data) LC-MS: M=251, RT=0.67 (min), [M+H]$^+$=252. $^1$H-NMR (400 MHz, DMSO-d$_6$, δ ppm): 8.64 (1H, d, J=3 Hz), 8.18 (1H, s), 7.97 (1H, s), 7.95 (1H, d, J=3 Hz), 3.90 (3H, s), 3.89 (3H, s).

Working Example 14

Synthesis of 4-(5-fluoro-2-methoxypyrimidin-4-yl)-N-(6-fluoro-2-phenyl-[1,2,4]triazolo[1,5-a]pyridin-7-yl)-1-methyl-1H-pyrazole-5-carboxamide

[C164]

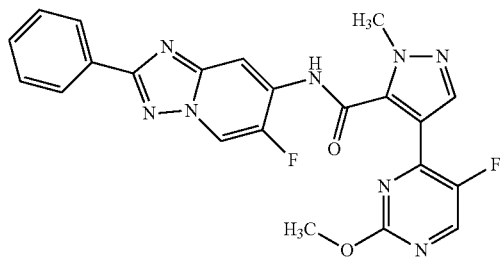

<Step 1> Synthesis of N-(2-amino-5-fluoropyridin-4-yl)-4-(5-fluoro-2-methoxypyrimidin-4-yl)-1-methyl-1H-pyrazole-5-carboxamide

[C165]

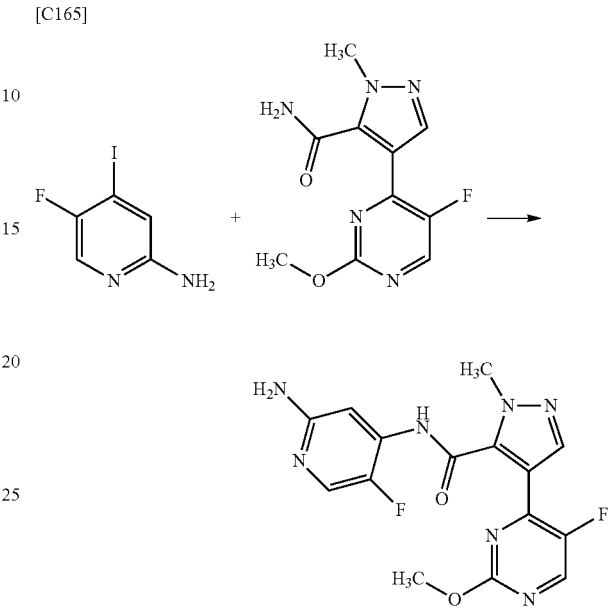

5-fluoro-4-iodopyridine-2-amine (104 mg, 0.44 mmol), which was synthesized using a method similar to that in Working Example 3, 4-(5-fluoro-2-methoxypyrimidin-4-yl)-1-methyl-1H-pyrazole-5-carboxamide (100 mg, 0.4 mmol), which was synthesized in Working Example 13, trans-N,N'-dimethylcyclohexane-1,2-diamine (34 mg, 0.24 mmol), copper iodide (CuI) (23 mg, 0.12 mmol) and potassium phosphate (169 mg, 0.8 mmol) were mixed in dimethyl sulfoxide (1 mL), and heated for 3.7 hours at 60° C. A 28% aqueous solution of ammonia (0.2 mL) was added, and the obtained mixture was stirred at room temperature and then diluted with water. The reaction mixture was extracted using methylene chloride, and the obtained organic layer was washed with water and a saline solution, dried using sodium sulfate, and concentrated. The obtained solid residue was triturated with methyl tert-butyl ether (MTBE), filtered off, washed with methyl tert-butyl ether, and dried, and N-(2-amino-5-fluoropyridin-4-yl)-4-(5-fluoro-2-methoxypyrimidin-4-yl)-1-methyl-1H-pyrazole-5-carboxamide (99 mg, 69%) was obtained as a gray solid.

(Physical property data) LC-MS: M=361, RT=0.71 (min), [M+H]$^+$=362.

$^1$H-NMR (400 MHz, DMSO-d$_6$, δ ppm): 10.8 (1H, s), 8.65 (1H, d, J=3 Hz), 8.02 (1H, d, J=3 Hz), 7.84 (1H, s), 7.37 (1H, d, J=5 Hz), 5.91 (2H, s), 3.92 (3H, s), 3.68 (3H, s).

---

(Physical property data) LC-MS: M=252, RT=0.81 (min), [M+Na]$^+$=275. $^1$H-NMR (300 MHz, CDCl$_3$, δ ppm): 8.54 (1H, d, J=3 Hz), 8.28 (1H, d, J=4 Hz), 4.36 (3H, s), 4.09 (3H, s).

115

<Step 2> Synthesis of N-(2-benzimidamido-5-fluoropyridin-4-yl)-4-(5-fluoro-2-methoxypyrimidin-4-yl)-1-methyl-1H-pyrazole-5-carboxamide

[C166]

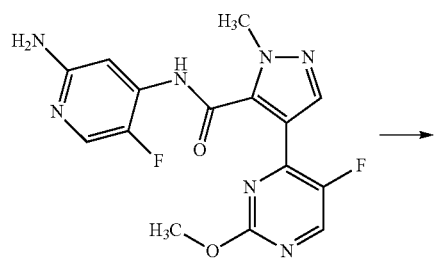

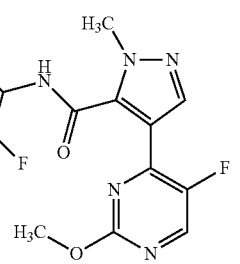

Pyridine (0.4 mL) and dimethyl sulfoxide (0.2 mL) were added to a mixture of N-(2-amino-5-fluoropyridin-4-yl)-4-(5-fluoro-2-methoxypyrimidin-4-yl)-1-methyl-1H-pyrazole-5-carboxamide (80 mg, 0.22 mmol), which was synthesized in <Step 1> in Working Example 14, and methylbenzimidothioate hydroiodide (80 mg, 0.29 mmol). The obtained solution was stirred for 35 minutes at 80° C., and methylbenzimidothioate hydroiodide (12 mg, 0.04 mmol) was added and stirred for a further 40 minutes. Acetone (0.4 mL) and a saturated aqueous solution of sodium hydrogen carbonate (0.4 mL) were added to the reaction mixture, the reaction mixture was stirred for 30 minutes at room temperature, after which water (1.6 mL) was added, and the reaction mixture was stirred for a further 1 hour. The obtained solid was filtered off, washed with water and dried, and N-(2-benzimidamido-5-fluoropyridin-4-yl)-4-(5-fluoro-2-methoxypyrimidin-4-yl)-1-methyl-1H-pyrazole-5-carboxamide (86 mg, 84%) was obtained as a gray solid.

(Physical property data) LC-MS: M=464, RT=0.82 (min), [M+H]$^+$=465. $^1$H-NMR (400 MHz, DMSO-d$_6$, δ ppm): 11.1 (1H, s), 8.67 (1H, d, J=3 Hz), 8.30 (1H, s), 8.07-8.01 (3H, m), 7.99-7.90 (1H, m), 7.54-7.45 (3H, m), 3.97 (3H, s), 3.68 (3H, s).

116

<Step 3> Synthesis of 4-(5-fluoro-2-methoxypyrimidin-4-yl)-N-(6-fluoro-2-phenyl-[1,2,4]triazolo[1,5-a]pyridin-7-yl)-1-methyl-1H-pyrazole-5-carboxamide

[C167]

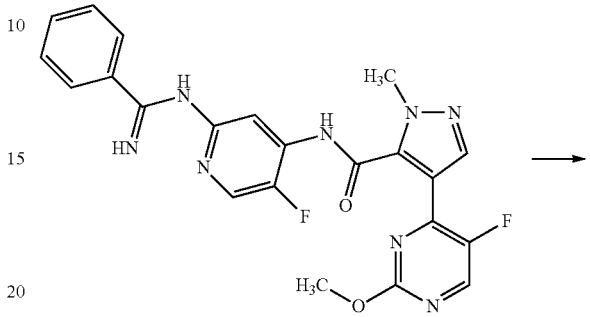

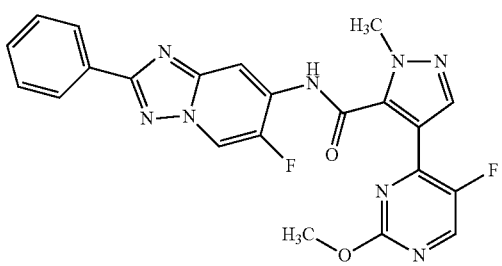

N-(2-benzimidamido-5-fluoropyridin-4-yl)-4-(5-fluoro-2-methoxypyrimidin-4-yl)-1-methyl-1H-pyrazole-5-carboxamide (70 mg, 0.15 mmol), which was synthesized in <Step 2> in Working Example 14, and a copper chloride (CuCl) catalyst (1.5 mg, 0.02 mmol) were mixed in pyridine (0.28 mL), and the obtained mixture was stirred in air for 3.5 hours at 100° C. 28% aqueous ammonia (0.07 mL) and water were added, and the obtained suspension was stirred for 45 minutes at room temperature. The generated solid was filtered off, washed with water and dried, and 4-(5-fluoro-2-methoxypyrimidin-4-yl)-N-(6-fluoro-2-phenyl-[1,2,4]triazolo[1,5-a]pyridin-7-yl)-1-methyl-1H-pyrazole-5-carboxamide (56 mg, 80%) was obtained as a beige solid.

(Physical property data) LC-MS: M=462, RT=1.10 (min), [M+H]$^+$=463.

$^1$H-NMR (400 MHz, DMSO-d$_6$, δ ppm): 11.3 (1H, s), 9.45 (1H, d, J=6 Hz), 8.69 (1H, d, J=3 Hz), 8.57 (1H, d, J=7 Hz), 8.20-8.17 (2H, m), 8.08 (1H, d, J=3 Hz), 7.57-7.49 (3H, m), 4.00 (3H, s), 3.67 (3H, s).

Working Example 15

Synthesis of methyl 1-methyl-4-(4-(trifluoromethyl)thiazol-2-yl)-1H-pyrazole-5-carboxylate <Step 1> Synthesis of methyl-4-(5,5-dimethyl-1,3,2-dioxaborinan)-2-yl)-1-methyl-1H-pyrazole-5-carboxylate

[C168]

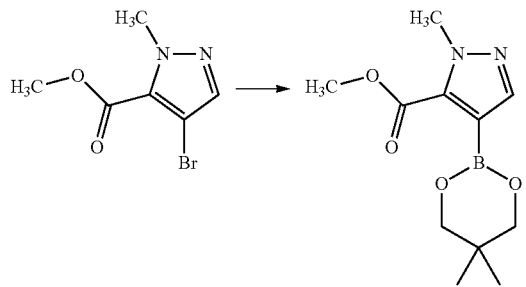

A 1,1'-bis(diphenylphosphino)ferrocene-palladium (II) dichloride dichloromethane complex (0.37 g, 0.46 mmol) and potassium acetate (3.6 g, 37 mmol) were added to a dimethyl sulfoxide solution (10 mL) of 4-bromo-1-methyl-1H-pyrazole-5-carboxylic acid methyl ester (CAS No.: 514816-42-3, 2.0 g, 9.1 mmol) and 5,5,5',5'-tetramethyl-2,2'-bi(1,3,2-dioxaborinane) (4.1 g, 18 mmol), and stirred for 4 hours at 100° C. in a nitrogen atmosphere. The reaction solution was cooled, water (50 mL) was added, and the reaction solution was extracted twice using ethyl acetate (100 mL). An organic layer was combined, and the obtained mixture was washed with water and a saturated saline solution in that order, and then dried with anhydrous sodium sulfate. A residue obtained by distilling of the solvent under reduced pressure was purified by means of silica gel column chromatography (silica gel: eluate; heptane:ethyl acetate 90:10 to 40:60), and the title compound (1.0 g) was obtained as a brown solid.

(Physical property data) LC-MS: M=252, RT=0.67 (min), [M+H]$^+$ of corresponding boronic acid=185.

$^1$H-NMR (300 MHz, CDCl$_3$, δ ppm): 7.58 (1H, s), 4.11 (3H, s), 3.88 (3H, s), 3.74 (4H, s), 1.05 (6H, s).

<Step 2> Synthesis of methyl 1-methyl-4-(4-(trifluoromethyl)thiazol-2-yl)-1H-pyrazole-5-carboxylate

[C169]

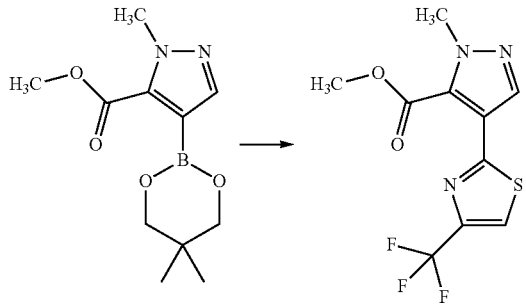

Using methyl-4-(5,5-dimethyl-1,3,2-dioxaborinan)-2-yl)-1-methyl-1H-pyrazole-5-carboxylate (300 mg, 1.19 mmol), which was synthesized in <Step 1> in Working Example 15, and 2-bromo-4-(trifluoromethyl)thiazole (291 mg), methyl 1-methyl-4-(4-(trifluoromethyl)thiazol-2-yl)-1H-pyrazole-5-carboxylate (259 mg) was obtained as a light brown solid using a method similar to that in <Step 1> in Working Example 1 or a method based on this method.

(Physical property data) LC-MS: M=291, RT=1.05 (min), [M+H]$^+$=292. $^1$H-NMR (400 MHz, CDCl$_3$, δ ppm): 8.11 (1H, s), 7.77-7.76 (1H, m), 4.21 (3H, s), 3.98 (3H, s).

Working Example 16

Synthesis of 1-methyl-4-(4-(trifluoromethyl)thiazol-2-yl)-1H-pyrazole-5-carboxylic acid

[C170]

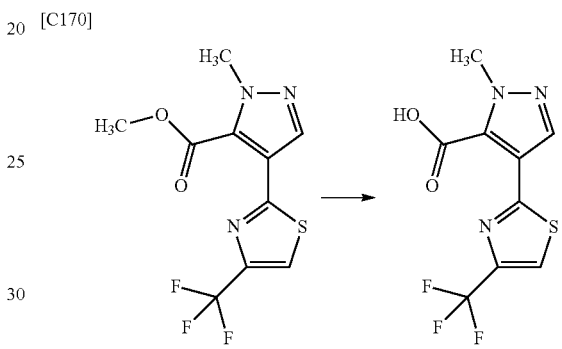

Using methyl 1-methyl-4-(4-(trifluoromethyl)thiazol-2-yl)-1H-pyrazole-5-carboxylate (210 mg), which was obtained in Working Example 15, 1-methyl-4-(4-(trifluoromethyl)thiazol-2-yl)-1H-pyrazole-5-carboxylic acid (173 mg) was obtained as a brown-white solid using a method similar to that in <Step 1> in Working Example 5 or a method based on this method.

(Physical property data) LC-MS: M=277, RT=4.98 (min), [M+H]$^+$=278. $^1$H-NMR (400 MHz, CDCl$_3$, δ ppm): 8.48-8.46 (1H, m), 8.08 (1H, s), 4.12 (3H, s).

Working Example 17

Synthesis of 1-methyl-4-(4-(trifluoromethyl)thiazol-2-yl)-1H-pyrazole-5-carboxamide

[C171]

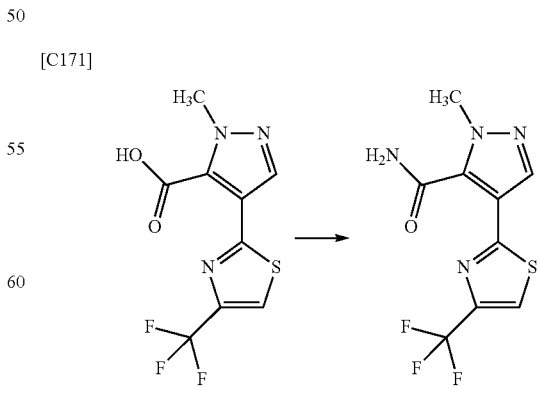

Using 1-methyl-4-(4-(trifluoromethyl)thiazol-2-yl)-1H-pyrazole-5-carboxylic acid (0.15 g, 0.54 mmol), which was synthesized using a method similar to that in Working Example 16, and ethyl chloroformate (0.057 mL, 0.6 mmol), 1-methyl-4-(4-(trifluoromethyl)thiazol-2-yl)-1H-pyrazole-5-carboxamide (66 mg, 44%) was obtained as a white solid using a method similar to that in Working Example 9.

(Physical property data) LC-MS: M=276, RT=0.90 (min), [M+H]$^+$=277. $^1$H-NMR (400 MHz, DMSO-d$_6$, δ ppm): 8.65 (1H, s), 8.44 (1H, q, J=1 Hz), 8.12 (1H, s), 8.02 (1H, s), 3.96 (3H, s).

Working Example 18

Synthesis of N-(6-fluoro-2-phenyl-[1,2,4]triazolo[1,5-a]pyridin-7-yl)-1-methyl-4-(4-(trifluoromethyl)thiazol-2-yl)-1H-pyrazole-5-carboxamide

[C172]

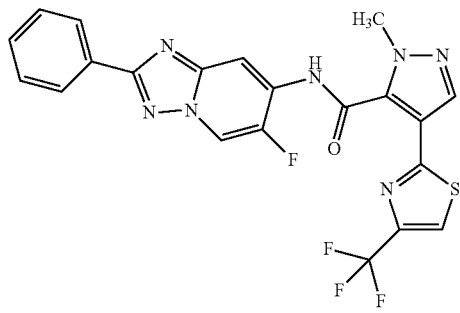

<Step 1> Synthesis of N-(2-amino-5-fluoropyridin-4-yl)-1-methyl-4-(4-(trifluoromethyl)thiazol-2-yl)-1H-pyrazole-5-carboxamide

[C173]

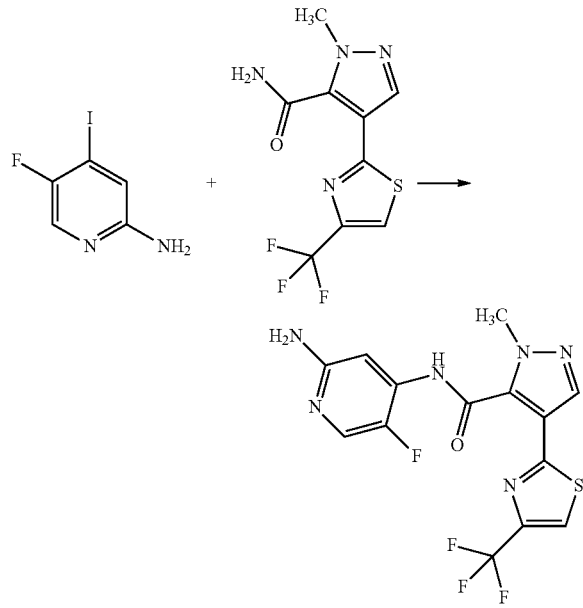

5-fluoro-4-iodopyridine-2-amine (38 mg, 0.16 mmol), which was synthesized using a method similar to that in Working Example 3, and 1-methyl-4-(4-(trifluoromethyl)thiazol-2-yl)-1H-pyrazole-5-carboxamide (40 mg, 0.14 mmol), which was synthesized in Working Example 17, were subjected to a reaction using a method based on <Step 2> in Working Example 6, after which a 28% aqueous solution of ammonia (0.08 mL) was added, stirred at room temperature, diluted with water, and extracted using methylene chloride. The obtained organic layer was washed with water and a saline solution, dried with sodium sulfate, and then concentrated. The obtained solid residue was triturated in MTBE, and N-(2-amino-5-fluoropyridin-4-yl)-1-methyl-4-(4-(trifluoromethyl)thiazol-2-yl)-1H-pyrazole-5-carboxamide (33 mg, 59%) was obtained as a beige solid.

(Physical property data) LC-MS: M=386, RT=0.86 (min), [M+H]$^+$=387. $^1$H-NMR (400 MHz, DMSO-d$_6$, δ ppm): 11.2 (1H, s), 8.46 (1H, s), 8.13 (1H, s), 7.87 (1H, s), 7.32 (1H, d, J=4 Hz), 5.94 (2H, s), 4.02 (3H, s).

<Step 2> Synthesis of N-(2-benzimidamido-5-fluoropyridin-4-yl)-1-methyl-4-(4-(trifluoromethyl)thiazol-2-yl)-1H-pyrazole-5-carboxamide

[C174]

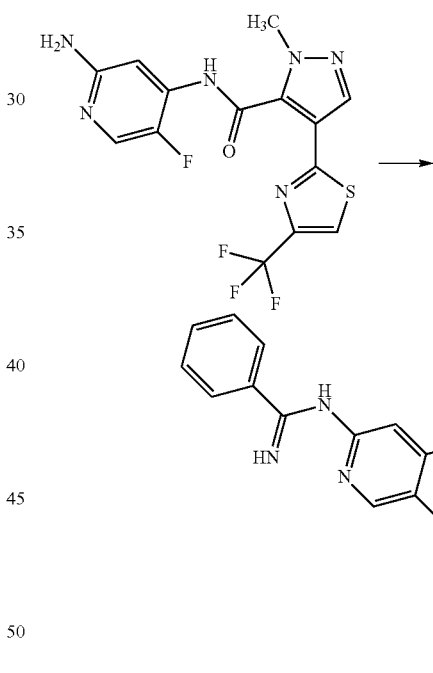

Using N-(2-amino-5-fluoropyridin-4-yl)-1-methyl-4-(4-(trifluoromethyl)thiazol-2-yl)-1H-pyrazole-5-carboxamide (25 mg, 0.06 mmol), which was synthesized in <Step 1> in Working Example 18, and methylbenzimidothioate hydroiodide (23 mg, 0.08 mmol; or 3.6 mg, 0.01 mmol), N-(2-benzimidamido-5-fluoropyridin-4-yl)-1-methyl-4-(4-(trifluoromethyl)thiazol-2-yl)-1H-pyrazole-5-carboxamide (27 mg, 85%) was obtained as a beige solid using a method similar to that in <Step 3> in Working Example 6.

(Physical property data) LC-MS: M=489, RT=0.95 (min), [M+H]$^+$=490. $^1$H-NMR (400 MHz, DMSO-d$_6$, δ ppm): 11.4 (1H, s), 9.82 (1H, s), 8.46 (1H, s), 8.33 (1H, s), 8.16 (1H, s), 8.04 (2H, d, J=6 Hz), 7.89 (1H, s), 7.53-7.45 (3H, m), 4.06 (3H, s).

<Step 3> Synthesis of N-(6-fluoro-2-phenyl-[1,2,4]triazolo[1,5-a]pyridin-7-yl)-1-methyl-4-(4-(trifluoromethyl)thiazol-2-yl)-1H-pyrazole-5-carboxamide

[C175]

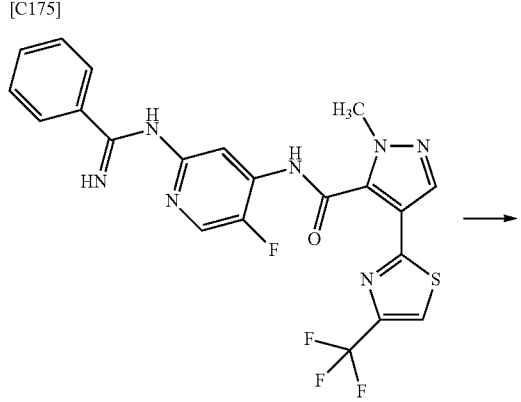

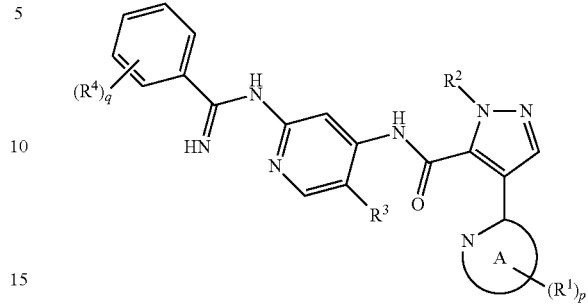

in formula (AD-3), p denotes an integer between 0 and 3; q denotes an integer between 0 and 2; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C206]

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group, the manufacturing method comprising stages in which a compound represented by formula (AD-1):

[C207]

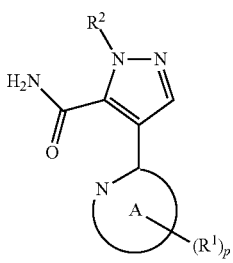

Using N-(2-benzimidamido-5-fluoropyridin-4-yl)-1-methyl-4-(4-(trifluoromethyl)thiazol-2-yl)-1H-pyrazole-5-carboxamide (20 mg, 0.04 mmol), which was synthesized in <Step 2> in Working Example 18, N-(6-fluoro-2-phenyl-[1,2,4]triazolo[1,5-a]pyridin-7-yl)-1-methyl-4-(4-(trifluoromethyl)thiazol-2-yl)-1H-pyrazole-5-carboxamide (15 mg, 75%) was obtained as a beige solid using a method similar to that in <Step 4> in Working Example 6.

(Physical property data) LC-MS: M=487, RT=1.25 (min), [M+H]⁺=488. ¹H-NMR (400 MHz, CDCl₃, δ ppm): 12.32 (1H, s), 8.86-8.80 (1H, m), 8.65-8.60 (1H, m), 8.30-8.22 (2H, m), 7.96-7.90 (1H, m), 7.85-7.80 (1H, m), 7.54-7.43 (3H, m), 4.37 (3H, s).

INDUSTRIAL APPLICABILITY

Provided by the present invention is a method for manufacturing a compound represented by formula (I), which has a short process and is suitable for industrial manufacturing. Also provided by the present invention is a synthesis intermediate that is useful for this manufacturing method.

The invention claimed is:

1. A method for manufacturing a compound represented by formula (AD-3) below:

in formula (AD-1), p, $R^1$, $R^2$ and ring A group represented by formula (II) are defined in the same way as for formula (AD-3) and a 2-amino-4-iodopyridine derivative represented by formula (PY-1):

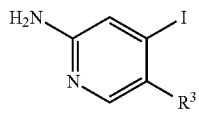

(PY-1)

in formula (PY-1), $R^3$ denotes a group arbitrarily selected from among a hydrogen atom and a fluorine atom are reacted with each other using a solvent which does not take part in the reaction and which is selected from the group consisting of 1,4-dioxane, tetrahydrofuran and 1,2-dimethoxyethane at a temperature between 0° C. and a temperature at which the solvent refluxes in the presence of N,N-dimethyl-1,2-ethanediamine, copper iodide and an inorganic base selected from the group consisting of potassium carbonate and potassium phosphate, thereby obtaining a compound represented by formula (AD-2):

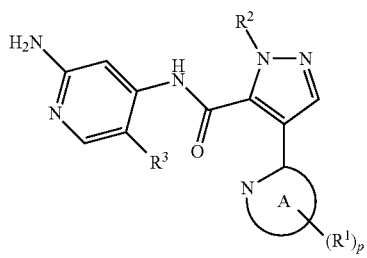

(AD-2)

in formula (AD-2), p, $R^1$, $R^2$, $R^3$ and ring A group represented by formula (II) are defined in the same way as for formula (AD-3), and the compound represented by formula (AD-2) and a compound represented by formula (IM-1):

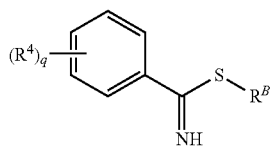

(IM-1)

in formula (IM-1), q and $R^4$ are defined in the same way as for formula (AD-3); and $R^B$ denotes a $C_{1-6}$ alkyl group or a salt thereof are reacted with each other using a solvent which does not take part in the reaction and which is selected from among dimethyl sulfoxide and pyridine at a temperature between 0° C. and a temperature at which the solvent refluxes, thereby obtaining the compound represented by formula (AD-3).

2. A compound represented by formula (AD-3) below:

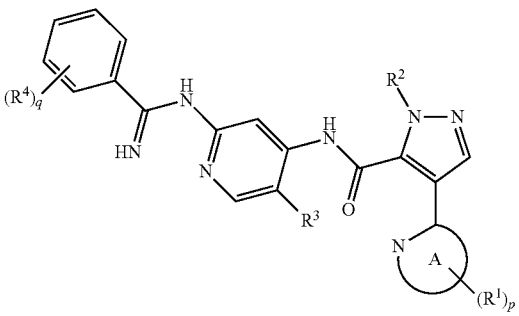

(AD-3)

in formula (AD-3), p denotes an integer between 0 and 3; q denotes an integer between 0 and 2; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

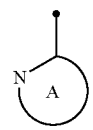

(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group, or a salt of the compound, or a solvate of the compound or salt.

3. The compound of claim 2, wherein the compound is any one of intermediate compounds below, or a salt of the intermediate compound, or a solvate of the intermediate compound or salt:

N-(2-benzimidamido-5-fluoropyridin-4-yl)-4-(2,5-dimethylpyrimidin-4-yl)-1-methyl-1H-pyrazole-5-carboxamide;

N-(2-benzimidamido-5-fluoropyridin-4-yl)-4-(2-methylpyrimidin-4-yl)-1-methyl-1H-pyrazole-5-carboxamide;

N-(2-benzimidamido-5-fluoropyridin-4-yl)-4-(5-fluoro-2-methoxypyrimidin-4-yl)-1-methyl-1H-pyrazole-5-carboxamide; and N-(2-benzimidamido-5-fluoropyridin-4-yl)-4-(4-(trifluoromethypthiazol-2-yl)-1-methyl-1H-pyrazole-5-carboxamide.

4. A method for manufacturing a compound represented by formula (AD-3) below:

[C217]

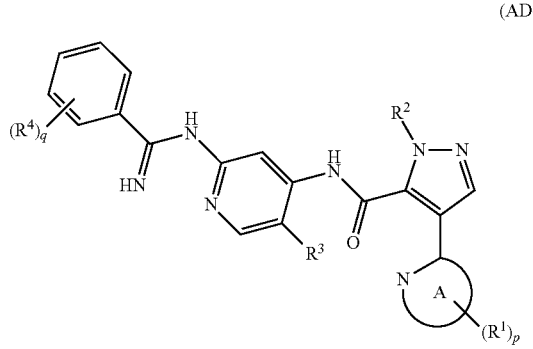

(AD-3)

in formula (AD-3), p denotes an integer between 0 and 3; q denotes an integer between 0 and 2; $R^1$ groups each independently denote a group arbitrarily selected from among a halogen atom, a cyano group, a $C_{1-6}$ alkyl group, a $C_{3-8}$ cycloalkyl group, a halogenated $C_{1-6}$ alkyl group, a $C_{2-6}$ alkenyl group, a $C_{1-6}$ alkoxy group, a $C_{1-6}$ alkoxy-$C_{1-6}$ alkyl group, a hydroxy-$C_{1-6}$ alkyl group and a $C_{2-7}$ alkanoyl group; $R^2$ denotes a $C_{1-6}$ alkyl group; $R^3$ denotes a group arbitrarily selected from among a hydrogen atom and a fluorine atom; $R^4$ groups each independently denote a group arbitrarily selected from among a halogen atom, a $C_{1-6}$ alkyl group and a $C_{1-6}$ alkoxy group; and ring A group represented by formula (II):

[C218]

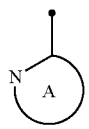

(II)

denotes a monocyclic 5- to 6-membered heteroaryl group arbitrarily selected from among a thiazol-2-yl group, a thiazol-4-yl group, a 1-methyl-1H-imidazol-4-yl group, a 1,3,4-thiadiazol-2-yl group, a 1,2,4-thiadiazol-5-yl group, a pyridin-2-yl group, a pyridazin-3-yl group, a pyrimidin-2-yl group, a pyrimidin-4-yl group and a pyrazin-2-yl group, the manufacturing method comprising a stage in which a compound represented by formula (AD-2):

[C219]

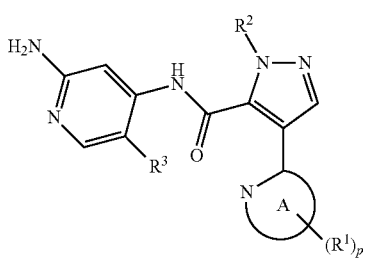

(AD-2)

in formula (AD-2), p, $R^1$, $R^2$, $R^3$ and ring A group represented by formula (II) are defined in the same way as for formula (AD-3) and a compound represented by formula (IM-1):

[C220]

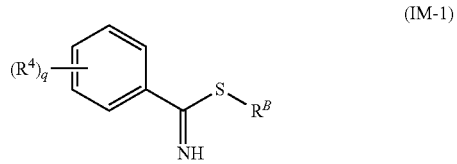

(IM-1)

in formula (IM-1), q and $R^4$ are defined in the same way as for formula (I); and $R^B$ denotes a $C_{1-6}$ alkyl group or a salt thereof are reacted with each other using a solvent which does not take part in the reaction and which is selected from among dimethyl sulfoxide and pyridine at a temperature between 0° C. and a temperature at which the solvent refluxes, thereby obtaining the compound represented by formula (AD-3).

* * * * *